US008299084B2

(12) United States Patent
Rao et al.

(10) Patent No.: US 8,299,084 B2
(45) Date of Patent: Oct. 30, 2012

(54) PIPERIDINE INHIBITORS OF JANUS KINASE 3

(75) Inventors: Tadimeti Rao, San Diego, CA (US); Chengzhi Zhang, San Diego, CA (US)

(73) Assignee: Auspex Pharmaceuticals, Inc., La Jolla, CA (US)

( * ) Notice: Subject to any disclaimer, the term of this patent is extended or adjusted under 35 U.S.C. 154(b) by 140 days.

(21) Appl. No.: 12/763,858

(22) Filed: Apr. 20, 2010

(65) Prior Publication Data

US 2010/0291026 A1    Nov. 18, 2010

Related U.S. Application Data

(60) Provisional application No. 61/170,858, filed on Apr. 20, 2009, provisional application No. 61/300,887, filed on Feb. 3, 2010.

(51) Int. Cl.
*A01N 43/90* (2006.01)
*A61K 31/519* (2006.01)
*C07D 487/00* (2006.01)

(52) U.S. Cl. .................. 514/265.1; 544/280

(58) Field of Classification Search .............. None
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan et al. | |
| 6,603,008 B1 | 8/2003 | Ando et al. | |
| 6,610,847 B2 | 8/2003 | Blumenkopf | |
| 6,627,754 B2 | 9/2003 | Blumenkopf | |
| 6,635,762 B1 | 10/2003 | Blumenkopf | |
| 6,696,567 B2 | 2/2004 | Blumenkopf | |
| 6,890,929 B2 | 5/2005 | Blumenkopf | |
| 6,956,041 B2 | 10/2005 | Blumenkopf | |
| 6,962,993 B2 | 11/2005 | Blumenkopf | |
| 6,965,027 B2 | 11/2005 | Flanagan | |
| 7,084,277 B2 | 8/2006 | Ripin | |
| 7,091,208 B2 | 8/2006 | Blumenkopf | |
| 7,192,963 B2 | 3/2007 | Blumenkopf | |
| 7,250,420 B2 | 7/2007 | Changelian | |
| 7,265,221 B2 | 9/2007 | Blumenkopf | |
| 7,301,023 B2 | 11/2007 | Flanagan | |
| 7,432,370 B2 | 10/2008 | Wilcox | |
| 7,517,990 B2 | 4/2009 | Ito et al. | |
| 7,569,569 B2 | 8/2009 | Blumenkopf | |
| 7,601,727 B2 | 10/2009 | Blumenkopf | |
| 7,687,507 B2 | 3/2010 | Blumenkopf | |
| RE41,783 E | 9/2010 | Blumenkopf et al. | |
| 2001/0053782 A1 | 12/2001 | Blumenkopf | |
| 2002/0013372 A1 | 1/2002 | Ekins | |
| 2002/0019526 A1 | 2/2002 | Changelian | |
| 2002/0068746 A1 | 6/2002 | Blumenkopf | |
| 2003/0073719 A1 | 4/2003 | Wilcox | |
| 2003/0130292 A1 | 7/2003 | Flanagan | |
| 2003/0212273 A1 | 11/2003 | Blumenkopf | |
| 2003/0220353 A1 | 11/2003 | Blumenkopf | |
| 2004/0053947 A1 | 3/2004 | Blumenkopf | |
| 2004/0058922 A1 | 3/2004 | Blumenkopf | |
| 2004/0102627 A1 | 5/2004 | Ripin | |
| 2004/0116449 A1 | 6/2004 | Changelian | |
| 2004/0229923 A1 | 11/2004 | Wilcox | |
| 2005/0113395 A1 | 5/2005 | Changelian | |
| 2005/0137679 A1 | 6/2005 | Changelian | |
| 2005/0137684 A1 | 6/2005 | Changelian | |
| 2005/0159433 A1 | 7/2005 | Changelian | |
| 2005/0159434 A1 | 7/2005 | Flanagan | |
| 2005/0171128 A1 | 8/2005 | Blumenkopf | |
| 2005/0197349 A1 | 9/2005 | Blumenkopf | |
| 2005/0288313 A1 | 12/2005 | Blumenkopf | |
| 2006/0241131 A1 | 10/2006 | Blumenkopf | |
| 2007/0161666 A1 | 7/2007 | Blumenkopf | |
| 2007/0197695 A1 | 8/2007 | Potyen et al. | |

(Continued)

FOREIGN PATENT DOCUMENTS

WO        9526325  A2      10/1995

(Continued)

OTHER PUBLICATIONS

Jian-kang Jiang et al.; Examining the Chirality, Conformation and Selective Kinase, Inhibition of 3-((3R,4R)-4-methyl-3-(methyl(7H-pyrrolo[2,3-d]pyrimidin-4-yl)amino)piperidin-1-yl)-3-oxopropanenitrile (CP-690,550), J. Med. Chem., 2008, 51(24), 8012-18.

Kushner, D. J et al.; Pharmacological uses and perspectives of heavy water and deuterated compounds, Can. J. Physiol. Pharmacol., 1999, 77, 79-88.

Bauer, L. et al.; Influence of long-term infusions on lidocaine kinetics, Clin. Pharmacol. Ther., 1982, 31(4), 433-7.

Borgstrom, L et al.; Comparative Pharmacokinetics of Unlabeled and Deuterium-Labeled Terbutaline: Demonstration of a Small Isotope Effect, J Pharm Sci, 77(11) 952-4 (1988).

Browne et al.; TR; Chapter 2. Isotope Effect: Implications for pharmaceutical investigations, Stable isotopes in pharmaceutical research; Elsevier; Amsterdam, 1997.

Browne et al., TR;et al.; Pharmacokinetic equivalence of stable-isotope-labeled and unlabeled drugs. Phenobarbital in man, J Clin Pharmacol, 1982, 22, 309-15.

(Continued)

*Primary Examiner* — Jeffrey Murray

(74) *Attorney, Agent, or Firm* — Dennis A. Bennett; Mike Sertic

(57) ABSTRACT

The present invention relates to new piperidine inhibitors of Janus kinase 3 activity, pharmaceutical compositions thereof, and methods of use thereof.

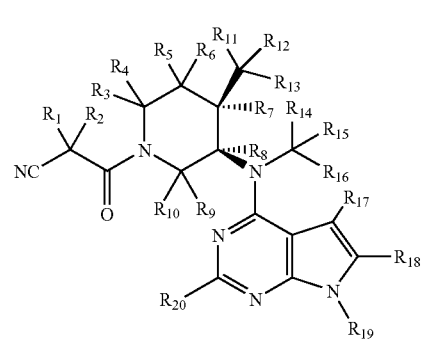

Formula I

5 Claims, No Drawings

U.S. PATENT DOCUMENTS

| | | | |
|---|---|---|---|
| 2007/0292430 A1 | 12/2007 | Blumenkopf | |
| 2008/0033011 A1 | 2/2008 | Tung | |
| 2008/0207594 A1 | 8/2008 | Mussmann | |
| 2008/0254029 A1 | 10/2008 | Yanni | |
| 2008/0287423 A1 | 11/2008 | Mussmann | |
| 2009/0062301 A1 | 3/2009 | Maibucher | |
| 2009/0156602 A1 | 6/2009 | Cooke | |
| 2009/0163523 A1 | 6/2009 | Lake | |
| 2009/0182035 A1 | 7/2009 | Yanni | |
| 2009/0312338 A1 | 12/2009 | Wishart et al. | |
| 2010/0035903 A1 | 2/2010 | Blumenkopf | |

FOREIGN PATENT DOCUMENTS

| | | | |
|---|---|---|---|
| WO | 9610562 A1 | 4/1996 | |
| WO | 9965908 A1 | 12/1999 | |
| WO | 9965909 A1 | 12/1999 | |
| WO | 0142246 A2 | 6/2001 | |
| WO | 0200661 A1 | 1/2002 | |
| WO | 02096909 A1 | 12/2002 | |
| WO | WO02/096909 | * 12/2002 | |
| WO | 03048162 A1 | 6/2003 | |
| WO | 2004046112 A2 | 6/2004 | |
| WO | 2004047843 A1 | 6/2004 | |
| WO | 2005051393 A1 | 6/2005 | |
| WO | 2005060972 A2 | 7/2005 | |
| WO | 2005063251 A1 | 7/2005 | |
| WO | 2005063318 A1 | 7/2005 | |
| WO | 2005105146 A1 | 11/2005 | |
| WO | 2006013114 A1 | 2/2006 | |
| WO | 2006056399 A2 | 6/2006 | |
| WO | 2006117212 A2 | 11/2006 | |
| WO | 2006117221 A1 | 11/2006 | |
| WO | 2006136374 A2 | 12/2006 | |
| WO | 2007012953 A2 | 2/2007 | |
| WO | 2007107318 A1 | 9/2007 | |
| WO | 2008029237 A2 | 3/2008 | |
| WO | 2008127975 A2 | 10/2008 | |
| WO | 2009007839 A1 | 1/2009 | |
| WO | 2009126682 A1 | 10/2009 | |
| WO | 2009140128 A2 | 11/2009 | |
| WO | 2009152133 A1 | 12/2009 | |
| WO | 2010123919 A2 | 10/2010 | |
| WO | 2010123919 A3 | 10/2010 | |

OTHER PUBLICATIONS

Burm, AGL et al.; Pharmacokinetics of Lidocaine and Bupivacaine and stbel isotope labelled analogues: a study in healthy volunteers, Biopharma & Drug Disp, 1988, 9, 85-95.

Elison, C et al.; Effect of deuteration of N-CH3 Group on Potency and enzymatic N-demethylation of morphin, Science, 1961,134(3485), 1078-9.

Farmer et al., Synthesis, metabolism, and antitumor activity of deuterated analogues of 1-(2-chloroethyl)-3-cyclohexyl-1-nitrosourea, J Med Chem, 1978, 21(6), 514-520.

Fisher et al., The complexities inherent in attempts to decrease drug clearance by blocking sites of CYP-mediated metabolism, Curr Opin in Drug Disc & Develop, 2006, 9(1), 101-9.

Foster et al.; Deuterium isotope effects in studies of drug metabolism, Trends in Pharma Sci, 1984, 524-7.

Helfenbein et al.; Isotopic Effect Study of Propofol Deuteration on the Metabolism, Activity, and Toxicity of the Anesthetic, J Med Chem, 2002, 45, 5806-8.

Lee et al.; Deuterium magic angle spinning studies of substrates bound to cytochrome P450, Biochem., 1999, 38, 10808-13.

Mamada et al.; Pharmacokinetic equivalence of deuterium-labeled and unlabeled phenytoin, Drug Metab Disp., 1986, 14(4) 509-11.

Nelson et al.; The use of deuterium isotope effects to probe the active site properties, mechanism, of cytochrome P450-catalyzed reactions, and mechanisms of metabolically dependent toxicity, Drug Metab Disp., 2003, 31(12), 1481-98.

Nelson et al.; Primary and B-Secondary Deuterium Isotope Effects in N-Deethylation reactions, J Med Chem., 1975, 18(11) 1062-5.

Pohl et al., Determination of Toxic Pathways of Metabolism by Deuterium Substitution, Drug Metab Rev., 1984, 15(7), 1335-51.

Rampe et al., Deuterated analogs of verapamil and nifedipine. Synthesis and biological activity, Eur J Med Chem., 1993, 28, 259-63.

Baillie, Thomas; The Use of Stable Isotopes in Pharmaceutical Researc, Pharmacological Reviews, 1981, 33(2), 81-132.

Browne, Thomas; Stable Isotope Techniques in Early Drug Development: An Economic Evaluation, J. Clin. Pharmacol., 1998, 38, 213-220.

Cherrah et al.; Study of Deuterium Isotope Effects on Protein Binding by Gas Chromatography/Mass Spectrometry. Caffeine and Deuterated Isomers, Biomedical and Environmental Mass Spectrometry, 1987, 14, 653-657, J. Neurochem., 1986, 46(2), 399-404.

Gouyette, Alain; Use of Deuterium-Labelled Elliptinium and Its Use in Metabolic Studies, Biomedical and Environmental Mass Spectrometry, 1988, 15, 243-247.

Haskins, N. J.; The Application of Stable Isotopes in Biomedical Research, Biomedical Mass Spectrometry, 1982, 9(7), 269-277.

Honma et al.; The Metabolism of Roxatidine Acetate Hydrochloride, Drug Metabolism and Disposition, 1987, 15(4), 551-559.

Pieiaszek et al.; Moricizine Bioavailability Via Simultaneous, Dual, Stable Isotope Administration: Bioequivalence Implications, J. Clin. Pharmacol., 1999, 39, 817-825.

Tonn et al.; Simultaneous Analysis of Diphenylhydramine and a Stable Isotope Analog (2H10) Diphenylhydramine Using Capillary Gas Chromatography With Mass Selective Detection in Biological Fluids From Chronically Instrumented Pregnant Ewes, Biomedical Mass Spectrometry, 1993, 22, 633-642.

Wolen et al.; The Application of Stable Isotopes to Studies of Drug Bioavailibility and Bioequivalence, J. Clin. Pharmacol., 1986, 26, 419-424.

Dalvie et al.; Assessment of Three Human in Vitro Systems in the Generation of Major Human Excretory and Circulatory Metabolites, Chem. Res. Toxicol., 2009, 22(2), 357-368.

Van Gurp et al.; Phase 1 Dose-Escalation Study of CP-690550 in Stable Renal Allograft Recipients: Preliminary Findings of Safety, Tolerability, Effects on Lymphocyte Subsets and Pharmacokinetics, Am. J. Transplantation, 2008, 8, 1711-1718.

West, Kevin; CP-690550, A JAK3 Inhibitor as an Immunosuppressant for the Treatment of Rheumatoid Arthritis, Transplant Rejection, Psoriasis and Other Immune-Mediated Disorders, Curr. Opinion Invest. Drugs, 2009, 10(5), 491-504.

Lawendy et al.; Effect of CP-690,550, An Orally Active Janus Kinase Inhibitor, on Renal Function in Healthy Adult Volunteers, J. Clin. Pharmacol., 2009, 49, 423-429.

Williams et al.; Dissecting Specificity in the Janus Kinases: The Structures of JAK-Specific Inhibitors Complexed to the JAK1 and JAK2 Protein Tyrosine Kinase Domains, J. Mol. Biol., 2009, 387, 219-232.

Prakash et al.; Metabolism, Pharmacokinetics and Excretion of a Janus Kinase-3 Inhibitor, CP-690,550, in Healthy Male Volunteers, American Association of Pharmaceutical Scientists Jornal, Abstracts, 2008, 2008-002492.

Krishnaswami et al.; Effect of CYP2C19 Polymorphism on the Pharmacokinetics of CP-690,550, A Janus Kinase Inhibitor, American Association of Pharmaceutical Scientists Jornal, Abstracts, 2009, 2009-000036.

Van Gurp et al.; The Effect of the JAK Inhibitor CP-690,550 on Peripheral Immune Parameters in Stable Kidney Allograft Patients, Transplantation, 2009, 87, 79-86.

Vincenti et al.; What's Next in the Pipeline, Am. J. Transplantation, 2008, 8, 1972-1981.

Price et al.; Mild and Efficient DBU-Catalyzed Amidation of Cyanoacetates, Org. Lett., 2009, 11(9), 2009, 2003-2006.

Dyck et al., Effects of Deuterium Substitution on the Catabolism of Beta-Phenethylamine: An in Vivo Study, J. Neurochem., 1986, 46(2), 399-404.

Foster, A.B., Deuterium Isotope Effects in the Metabolism of Drugs and Xenobiotics: Implications for Drug Design, Adv. In Drug Research, (1985), vol. 14, 1-40.

Supplemental European Search Report, EP2421867, Auspex Pharmaceuticals, Publication date Sep. 6, 2012.

* cited by examiner

PIPERIDINE INHIBITORS OF JANUS KINASE 3

This application claims the benefit of priority of U.S. provisional applications No. 61/170,858, filed Apr. 20, 2009, and No. 61/300,887, filed Feb. 3, 2010, the disclosures of which are hereby incorporated by reference as if written herein in their entireties.

Disclosed herein are new piperidine compounds, pharmaceutical compositions made thereof, and methods to inhibit Janus kinase 3 activity in a subject are also provided for, for the treatment of disorders such as renal transplant rejection, rheumatoid arthritis, psoriasis, inflammatory bowel disease, dry eye syndrome, asthma, transplant rejection, organ transplant, xeno transplation, lupus, multiple sclerosis, Type I diabetes, complications from diabetes, cancer, atopic dermatitis, autoimmune thyroid disorders, ulcerative colitis, Crohn's disease, Alzheimer's disease, and leukemia.

CP-690550 (CAS #477600-75-2, Tasocitinib), 4-methyl-3-(methyl-7H-pyrrolo[2,3-d]pyrimidin-4-ylamino)-beta-oxo-(3R,4R)-1-piperidinepropanenitrile, is a Janus kinase 3 inhibitor. CP-690550 is under investigation for the treatment of renal transplant rejection, rheumatoid arthritis, psoriasis, inflammatory bowel disease, dry eye syndrome, asthma, and transplant rejection (Jiang et al., *J. Med. Chem.* 2008, 51, 8012-8018; U.S. Pat. No. 6,627,754; and WO 2003/048162). CP-690550 has also shown promise in treating organ transplant, xeno transplation, lupus, multiple sclerosis, Type I diabetes, complications from diabetes, cancer, atopic dermatitis, autoimmune thyroid disorders, ulcerative colitis, Crohn's disease, Alzheimer's disease, and leukemia (U.S. Pat. No. 6,627,754; and WO 2003/048162).

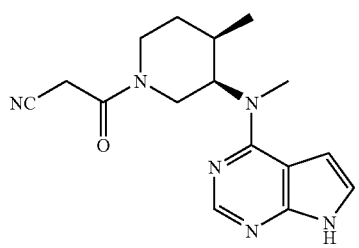

CP-690550

In vitro studies with $^{14}$C labeled CP-690550 in 6 human male volunteers demonstrated rapid uptake of CP-690550 in humans, with total radioactivity peaking at ~1 hour after oral administration (Prakash et al., *AAPS Journal* 2008, 10(S2)). The mean terminal phase half-lives for unchanged CP-690550 and total radioactivity were both approximately 3.2 hours, and more than 65% of the total circulating radioactivity was accounted for by unchanged CP-690550 (Prakash et al., *AAPS Journal* 2008, 10(S2)). The remaining radioactivity in plasma was attributable to eight metabolites each accounting for <5% of the total radioactivity (Prakash et al., *AAPS Journal* 2008, 10(S2)). The major primary metabolic pathways were found to include: oxidation of the pyrrolopyrimidine ring, oxidation of the piperidine ring, and oxidation of the piperidine ring side-chain (Prakash et al., *AAPS Journal* 2008, 10(S2)). The minor metabolic routes were due to N-demethylation and conjugation with glucuronic acid (Prakash et al., *AAPS Journal* 2008, 10(S2)). The clearance pathways of CP-690550 are approximately 70% non-renal (via hepatic metabolism by CYP3A4/5 and CYP2C19) and 30% renal excretion of unchanged drug (Krishnaswami et al., *AAPS Journal* 2009, 11(S2)).

Deuterium Kinetic Isotope Effect

In order to eliminate foreign substances such as therapeutic agents, the animal body expresses various enzymes, such as the cytochrome $P_{450}$ enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) π-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae^{-E_{act}/RT}$. The Arrhenius equation states that, at a given temperature, the rate of a chemical reaction depends exponentially on the activation energy ($E_{act}$).

The transition state in a reaction is a short lived state along the reaction pathway during which the original bonds have stretched to their limit. By definition, the activation energy $E_{act}$ for a reaction is the energy required to reach the transition state of that reaction. Once the transition state is reached, the molecules can either revert to the original reactants, or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^{1}$H), a C—D bond is stronger than the corresponding C-$^{1}$H bond. If a C-$^{1}$H bond is broken during a rate-determining step in a chemical reaction (i.e. the step with the highest transition state energy), then substituting a deuterium for that protium will cause a decrease in the reaction rate. This phenomenon is known as the Deuterium Kinetic Isotope Effect (DKIE). The magnitude of the DKIE can be expressed as the ratio between the rates of a given reaction in which a C-$^{1}$H bond is broken, and the same reaction where deuterium is substituted for protium. The DKIE can range from about 1 (no isotope effect) to very large numbers, such as 50 or more. Substitution of tritium for hydrogen results in yet a stronger bond than deuterium and gives numerically larger isotope effects.

Deuterium ($^{2}$H or D) is a stable and non-radioactive isotope of hydrogen which has approximately twice the mass of protium ($^{1}$H), the most common isotope of hydrogen. Deuterium oxide ($D_2O$ or "heavy water") looks and tastes like $H_2O$, but has different physical properties.

When pure $D_2O$ is given to rodents, it is readily absorbed. The quantity of deuterium required to induce toxicity is extremely high. When about 0-15% of the body water has been replaced by $D_2O$, animals are healthy but are unable to gain weight as fast as the control (untreated) group. When about 15-20% of the body water has been replaced with $D_2O$, the animals become excitable. When about 20-25% of the body water has been replaced with $D_2O$, the animals become so excitable that they go into frequent convulsions when stimulated. Skin lesions, ulcers on the paws and muzzles, and necrosis of the tails appear. The animals also become very aggressive. When about 30% of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$. Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetyl chloride. However, this method may not be applicable to all drug classes. For example, deuterium incorporation can lead to metabolic switching. Metabolic switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

CP-690550 is a Janus kinase 3 inhibitor. The carbon-hydrogen bonds of CP-690550 contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation may produce a detectable Deuterium Kinetic Isotope Effect (DKIE) that could affect the pharmacokinetic, pharmacologic and/or toxicologic profiles of CP-690550 in comparison with CP-690550 having naturally occurring levels of deuterium.

Based on discoveries made in our laboratory, as well as considering the literature, CP-690550 is metabolized in humans at the N-methyl group, the piperidine methyl group, the piperidine ring, and the alpha-carbonyl methyl group. The current approach has the potential to prevent metabolism at these sites. Other sites on the molecule may also undergo transformations leading to metabolites with as-yet-unknown pharmacology/toxicology. Limiting the production of these metabolites has the potential to decrease the danger of the administration of such drugs and may even allow increased dosage and/or increased efficacy. All of these transformations can occur through polymorphically-expressed enzymes, exacerbating interpatient variability. Further, some disorders are best treated when the subject is medicated around the clock or for an extended period of time. For all of the foregoing reasons, a medicine with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has the strong potential to slow the metabolism of CP-690550 and attenuate interpatient variability.

Novel compounds and pharmaceutical compositions, certain of which have been found to inhibit Janus kinase 3 activity have been discovered, together with methods of synthesizing and using the compounds, including methods for the treatment of Janus kinase 3-mediated disorders in a patient by administering the compounds as disclosed herein.

In certain embodiments of the present invention, compounds have structural Formula I:

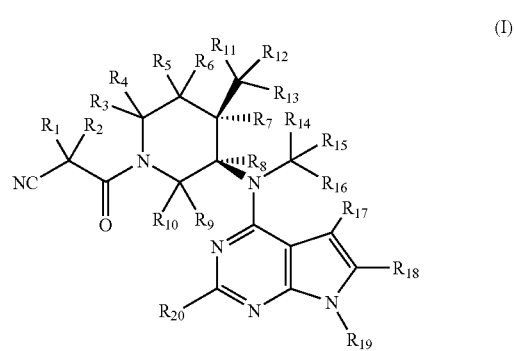

(I)

or a pharmaceutically acceptable salt thereof, wherein:
$R_1$-$R_{20}$ are independently selected from the group consisting of hydrogen and deuterium; and
at least one of $R_1$-$R_{20}$ is deuterium.
In further embodiments, at least one of $R_1$-$R_2$ is deuterium.
In further embodiments, $R_1$-$R_2$ are deuterium.
In further embodiments, at least one of $R_{11}$-$R_{13}$ is deuterium.
In further embodiments, $R_{11}$-$R_{13}$ are deuterium.
In further embodiments, $R_{20}$ is deuterium.
In further embodiments, at least six of $R_3$-$R_{10}$ are deuterium.
In further embodiments, at least seven of $R_3$-$R_{10}$ are deuterium.
In further embodiments, $R_3$-$R_{10}$ are deuterium.
In further embodiments, $R_1$-$R_2$ and $R_{11}$-$R_{13}$ are deuterium.
In further embodiments, $R_1$-$R_2$ and $R_{20}$ are deuterium.
In further embodiments, $R_1$-$R_2$ and at least six of $R_3$-$R_{10}$ are deuterium.
In further embodiments, $R_1$-$R_2$ and $R_3$-$R_{10}$ are deuterium.
In further embodiments, $R_{11}$-$R_{13}$ and $R_{20}$ are deuterium.
In further embodiments, $R_{11}$-$R_{13}$ and at least six of $R_3$-$R_{10}$ are deuterium.
In further embodiments, $R_{11}$-$R_{13}$ and $R_3$-$R_{10}$ are deuterium.
In further embodiments, $R_{20}$ and at least six of $R_3$-$R_{10}$ are deuterium.
In further embodiments, $R_{20}$ and $R_3$-$R_{10}$ are deuterium.
In further embodiments, $R_1$-$R_2$, $R_{20}$, and at least six of $R_3$-$R_{10}$ are deuterium.
In further embodiments, $R_1$-$R_2$, $R_{20}$, and $R_3$-$R_{10}$ are deuterium.
In further embodiments, $R_1$-$R_2$, $R_{11}$-$R_{13}$, and at least six of $R_3$-$R_{10}$ are deuterium.
In further embodiments, $R_1$-$R_2$, $R_{11}$-$R_{13}$, and $R_3$-$R_{10}$ are deuterium.
In further embodiments, $R_1$-$R_2$, $R_{11}$-$R_{13}$, and $R_{20}$ are deuterium.
In further embodiments, $R_1$-$R_2$, $R_{11}$-$R_{13}$, $R_{20}$, and at least six of $R_3$-$R_{10}$ are deuterium.
In further embodiments, $R_1$-$R_2$, $R_{11}$-$R_{13}$, $R_{20}$, and $R_3$-$R_{10}$ are deuterium.

Certain compounds disclosed herein may possess useful Janus kinase 3 inhibiting activity, and may be used in the treatment or prophylaxis of a disorder in which Janus kinase 3 plays an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for inhibiting Janus kinase 3 activity. Other embodiments provide methods for treating a Janus kinase 3-mediated disorder in a patient in need of such treatment, comprising administering to said patient a therapeutically effective amount of a compound or composition according to the present invention. Also provided is the use of certain compounds disclosed herein for use in the manufacture of a medicament for the prevention or treatment of a disorder ameliorated by inhibiting Janus kinase 3 activity.

The compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In certain embodiments, the compound disclosed herein may expose a patient to a maximum of about 0.000005% $D_2O$ or about 0.00001% DHO, assuming that all of the C—D bonds in the compound as disclosed herein are metabolized and released as $D_2O$ or DHO. In certain embodiments, the levels of $D_2O$ shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of $D_2O$ or DHO upon drug metabolism.

In certain embodiments, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

In certain embodiments, compounds have structural Formula II:

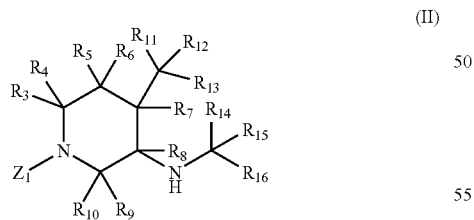

or a salt thereof, wherein:

Z$_1$ is an amino protecting group;

R$_3$-R$_{16}$ are independently selected from the group consisting of hydrogen and deuterium; and at least one of R$_3$-R$_{16}$ is deuterium.

In further embodiments, Z$_1$ is benzyl.

In further embodiments, the compounds of structural Formula II have a structure selected from the group consisting of:

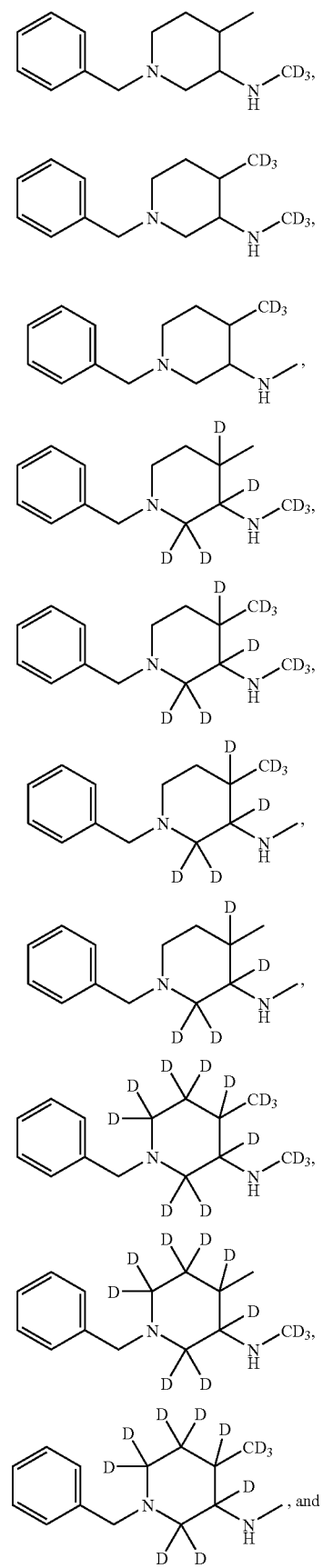

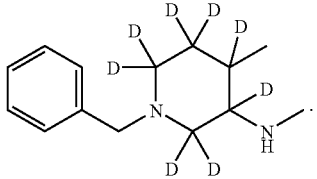

In certain embodiments, disclosed herein is a method of preparing a compound of structural Formula II:

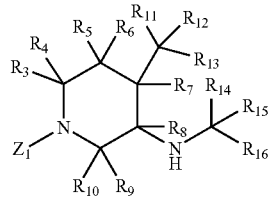

(II)

wherein:

$Z_1$ is selected from the group consisting of hydrogen and an amino protecting group;

$R_3$-$R_{16}$ are independently selected from the group consisting of hydrogen and deuterium;

at least one of $R_3$-$R_{16}$ is deuterium; comprising:

reacting a compound of structural Formula III, wherein $Z_2$ is a carboxyl protecting group, with a compound of structural Formula IV in the presence of an appropriate base, such as sodium hydride, in an appropriate solvent, such as tetrahydrofuran, to give a compound of structural Formula V

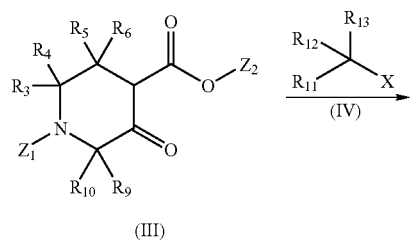 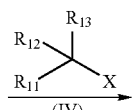

(III) (IV)

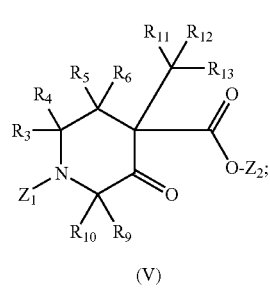

(V)

reacting a compound of structural Formula V with an appropriate acid, such as hydrogen chloride or deuterium chloride, in an appropriate solvent, such as water or deuterium oxide, to give a compound of structural Formula VI

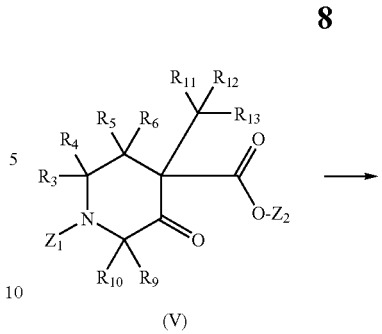

(V)

(VI)

reacting a compound of structural Formula VI with a compound of structural Formula VII in the presence of an appropriate reducing agent, such as sodium triacetoxyborohydride or sodium triacetoxyborodeuteride, in an appropriate solvent, such as tetrahydrofuran, to give a compound of structural Formula VII

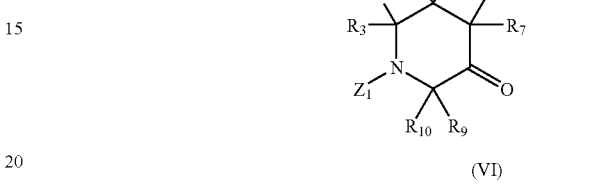

(VI) (VII)

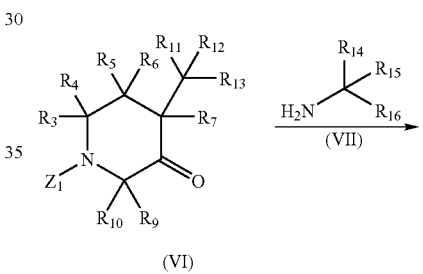

(II)

In certain embodiments, disclosed herein is a method of preparing a compound of structural Formula II:

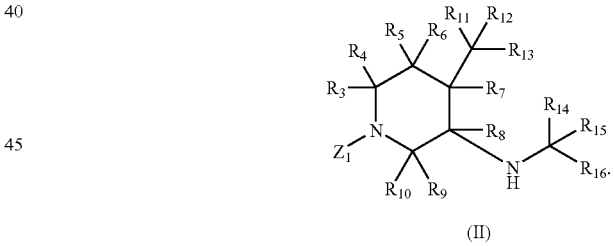

(II)

wherein:

$Z_1$ is selected from the group consisting of hydrogen and an amino protecting group;

$R_3$-$R_{16}$ are independently selected from the group consisting of hydrogen and deuterium;

at least one of $R_3$-$R_{16}$ is deuterium; comprising:

reacting a compound of structural Formula VIII with a compound of structural Formula X, wherein $Z_3$ is $C_1$-$C_2$ alkyl, in the presence of an appropriate acid, such as toluenesulfonic acid, in the presence of an optional dehydrating agent, such as trimethyl orthoformate, in an appropriate solvent, such as methanol, to give a compound of structural Formula IX

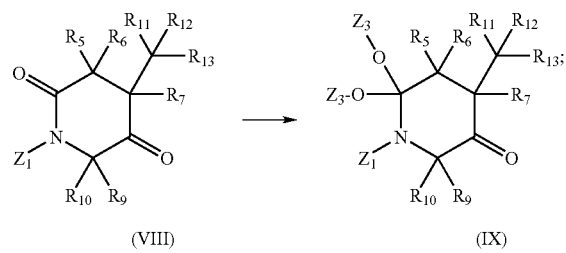

reacting a compound of structural Formula IX with an appropriate base, such as sodium hydroxide or $d_1$-sodium hydroxide or deuterium chloride, in an appropriate solvent, such as a combination of water or deuterium oxide and methanol or $d_4$-methanol, to give a compound of structural Formula IX;

reacting a compound of structural Formula IX with an appropriate acid, such as hydrogen chloride or deuterium chloride, in an appropriate solvent, such as water or deuterium oxide, to give a compound of structural Formula VIII

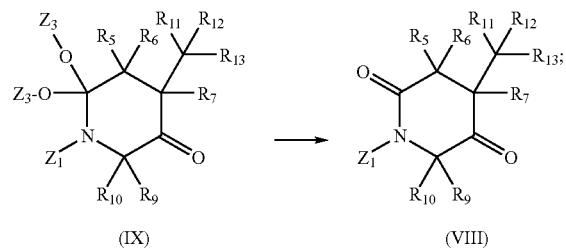

reacting a compound of structural Formula VIII with a compound of structural Formula VII in the presence of an appropriate reducing agent, such as sodium triacetoxyborohydride or sodium triacetoxyborodeuteride, in an appropriate solvent, such as tetrahydrofuran, to give a compound of structural Formula X

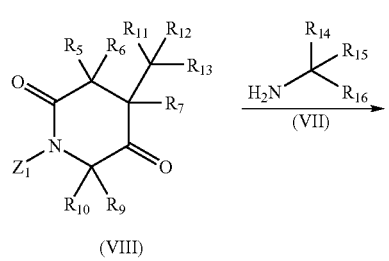

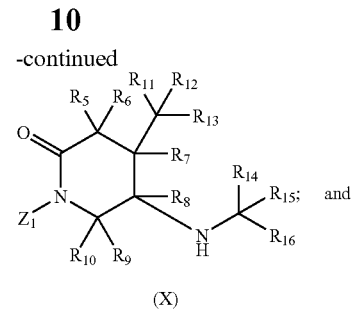

reacting a compound of structural Formula X with an appropriate reducing agent, such as lithium aluminum hydride or lithium aluminum deuteride, in an appropriate solvent, such as tetrahydrofuran, to give a compound of structural Formula X

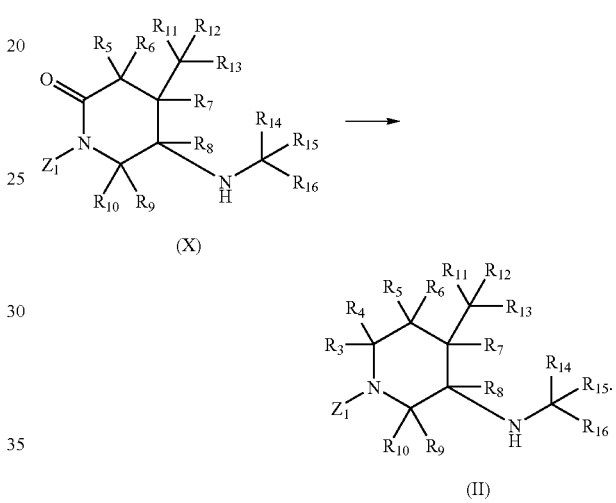

In certain embodiments, disclosed herein is a method of preparing a compound of structural Formula XIII:

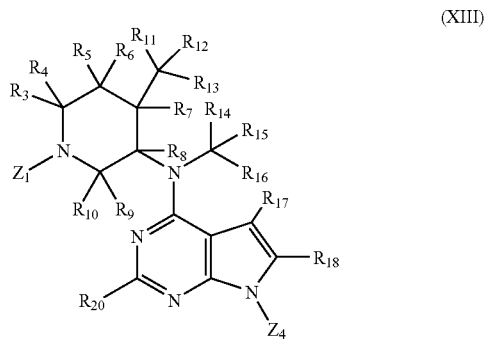

wherein:

$Z_1$ and $Z_4$ are independently selected from the group consisting of hydrogen and an amino protecting group;

$R_3$-$R_{18}$ and $R_{20}$ are independently selected from the group consisting of hydrogen and deuterium;

at least one of $R_3$-$R_{18}$ and $R_{20}$ is deuterium; comprising:

reacting a compound of structural Formula XI with a compound of structural Formula II, in the presence of an appropriate base, such as potassium carbonate, in an appropriate solvent, such as a combination of water and tetrahydrofuran, to give a compound of structural Formula XII

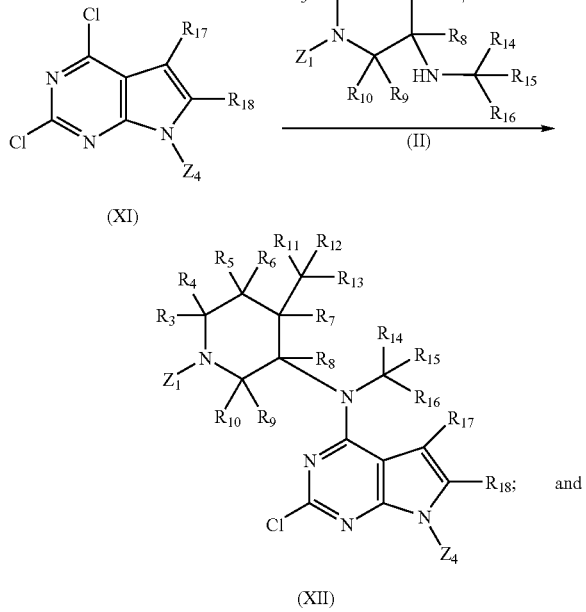

(XI)

(XII)

reacting a compound of structural Formula XII with an appropriate reducing agent, such as hydrogen or deuterium gas and an appropriate catalyst, such as palladium on carbon or palladium hydroxide on carbon, in an appropriate solvent, such as a combination of water or deuterium oxide and methanol or $d_4$-methanol, to give a compound of structural Formula XIII

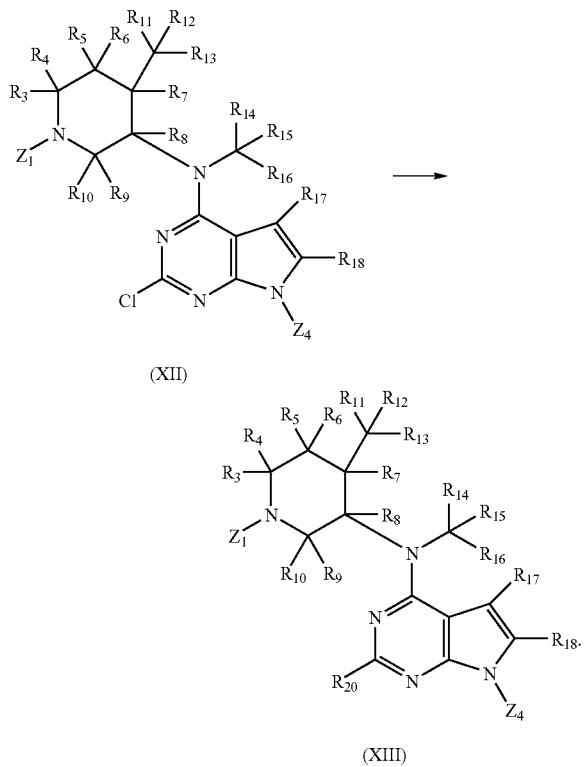

(XII)

(XIII)

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

As used herein, the terms below have the meanings indicated.

The singular forms "a", "an", and "the" may refer to plural articles unless specifically stated otherwise.

The term "about", as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ . . . to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium", when used to describe a given position in a molecule such as $R_1$-$R_{20}$ or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

Asymmetric centers exist in the compounds disclosed herein. These centers are designated by the symbols "R" or "S", depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The definition of "carboxyl protecting group" includes but is not limited to: 2-N-(morpholino)ethyl, choline, methyl, methoxyethyl, 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl. α-methylphenacyl, p-methoxyphenacyl, desyl, carboxamidomethyl, p-azobenzenecarboxamido-methyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(f-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butyl-4-methylphenyl, 2,6-di-tert-butyl-4-methoxyphenyl, p-(methylthio)phenyl, pentafluorophenyl, benzyl, triphenylmethyl, diphenylmethyl, bis(o-nitrophenyl)methyl, 9-anthrylmethyl, 2-(9,10-dioxo)anthrylmethyl. 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-Sulfobenzyl, 4-azidomethoxybenzyl, 4-{N-[1-(4,4-dimethyl-2,6-dioxocyclohexylidene)-3-methylbutyl]amino}benzyl, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl and the like.

The definition of "amino protecting group" includes but is not limited to:

2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 3,5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl. N-2-nitro-4-methoxybenzenesulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzenesulfonyl and the like;

—C(O)OR$_{80}$, where R$_{80}$ is selected from the group consisting of alkyl, substituted alkyl, aryl and more specifically R$_{80}$=methyl, ethyl, 9-fluorenylmethyl, 9-(2-sulfo)fluorenylmethyl. 9-(2,7-dibromo)fluorenylmethyl, 17-tetrabenzo[a,c,g,i]fluorenylmethyl. 2-chloro-3-indenylmethyl, benz[f]inden-3-ylmethyl, 2,7-di-t-butyl-[9-(10,10-dioxo-10,10,10,10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, tert-butyl, 1-adamantyl, 2-adamantyl, Vinyl, allyl, 1-Isopropylallyl, cinnamyl. 4-nitrocinnamyl, 3-(3-pyridyl)prop-2-enyl, 8-quinolyl, N-Hydroxypiperidinyl, alkyldithio, benzyl, p-methoxybenzyl, p-nitrobenzyl, p-bromobenzyl. p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-Iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-4'-pyridylethyl, phenyl, p-(phenylazo)benzyl, 2,4,6-trimethylphenyl, 4-(trimethylammonium)benzyl, 2,4,6-trimethylbenzyl and the like.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and symptoms.

The terms "treat", "treating", and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention. The terms "prevent", "preventing", and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "combination therapy" means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "Janus kinase 3" refers to a member of the Janus family of protein kinases. Although the other members of this family are expressed by essentially all tissues, Janus Kinase 3 expression is limited to hematopoetic cells. This is consistent with its essential role in signaling through the receptors for IL-2, IL-4, IL-7, IL-9, and IL-15 by non-covalent association of Janus Kinase 3 with the gamma chain common to these multichain receptors. XSCID patient populations have been identified with severely reduced levels of Janus Kinase 3 protein or with genetic defects to the common gamma chain, suggesting that immunosuppression should result from blocking signaling through the Janus Kinase 3 pathway. Animal studies have suggested that Janus Kinase 3 not only plays a critical role in B and T lymphocyte maturation, but that Janus Kinase 3 is constitutively required to maintain T cell function. Modulation of immune activity through this novel mechanism can prove useful in the treatment of T cell proliferative disorders such as transplant rejection and autoimmune diseases.

The term "Janus kinase 3-mediated disorder", refers to a disorder that is characterized by abnormal Janus Kinase 3 activity, or normal Janus Kinase 3 activity that when modulated ameliorates other abnormal biochemical processes. A Janus kinase 3-mediated disorder may be completely or partially mediated by modulating Janus kinase 3 activity. In particular, a Janus kinase 3-mediated disorder is one in which inhibiting Janus kinase 3 activity results in some effect on the underlying disorder e.g., administration of a Janus kinase 3 inhibitor results in some improvement in at least some of the patients being treated.

The term "Janus kinase 3 inhibitor", refers to the ability of a compound disclosed herein to alter the function of Janus kinase 3. An inhibitor may block or reduce the activity of Janus kinase 3 by forming a reversible or irreversible covalent bond between the inhibitor and Janus kinase 3 or through formation of a noncovalently bound complex. Such inhibition may be manifest only in particular cell types or may be contingent on a particular biological event. The term "Janus kinase 3 inhibitor", also refers to altering the function of Janus kinase 3 by decreasing the probability that a complex forms between Janus kinase 3 and a natural substrate. In some embodiments, inhibiting Janus kinase 3 activity may be assessed using the methods described in Jiang et al., *J. Med. Chem.* 2008, 51, 8012-8018; U.S. Pat. No. 6,627,754; and WO 2003/048162.

The term "inhibiting Janus kinase 3 activity" or "inhibition of Janus kinase 3 activity", refers to altering the function of Janus kinase 3 by administering a Janus kinase 3 inhibitor.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenecity, are commensurate with a reasonable benefit/risk ratio, and are effective for their intended use.

The term "pharmaceutically acceptable carrier", "pharmaceutically acceptable excipient", "physiologically acceptable carrier", or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. See, *Remington: The Science and Practice of Pharmacy*, 21st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

The terms "active ingredient", "active compound", and "active substance" refer to a compound, which is administered, alone or in combination with one or more pharmaceutically acceptable excipients or carriers, to a subject for treating, preventing, or ameliorating one or more symptoms of a disorder.

The terms "drug", "therapeutic agent", and "chemotherapeutic agent" refer to a compound, or a pharmaceutical composition thereof, which is administered to a subject for treating, preventing, or ameliorating one or more symptoms of a disorder.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, Controlled Drug Delivery 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

The compounds disclosed herein can exist as therapeutically acceptable salts. The term "pharmaceutically acceptable salt", as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts. For a more complete discussion of the preparation and selection of salts, refer to "Handbook of Pharmaceutical Salts, Properties, and Use," Stah and Wermuth, Ed., (Wiley-VCH and VHCA, Zurich, 2002) and Berge et al., *J. Pharm. Sci.* 1977, 66, 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy,* supra; *Modified-Release Drug Deliver Technology,* Rathbone et al., Eds., Drugs and the Pharmaceutical Science, Marcel Dekker, Inc., New York, N.Y., 2002, Vol. 126).

The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Disclosed herein are methods of treating a Janus kinase 3-mediated disorder comprising administering to a subject having or suspected of having such a disorder, a therapeutically effective amount of a compound as disclosed herein or a pharmaceutically acceptable salt, solvate, or prodrug thereof.

Janus kinase 3-mediated disorders, include, but are not limited to, renal transplant rejection, rheumatoid arthritis, psoriasis, inflammatory bowel disease, dry eye syndrome, asthma, transplant rejection, organ transplant, xeno transplation, lupus, multiple sclerosis, Type I diabetes, complications from diabetes, cancer, atopic dermatitis, autoimmune thyroid disorders, ulcerative colitis, Crohn's disease, Alzheimer's disease, leukemia, and/or any disorder which can lessened, alleviated, or prevented by administering a Janus kinase 3 inhibitor.

In certain embodiments, a method of treating a Janus kinase 3-mediated disorder comprises administering to the subject a therapeutically effective amount of a compound as disclosed herein, or a pharmaceutically acceptable salt, solvate, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome $P_{450}$ or monoamine oxidase isoform in the subject; (4) decreased metabolism via at least one polymorphically-expressed cytochrome $P_{450}$ isoform in the subject; (5) at least one statistically-significantly improved disorder-control and/ or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome $P_{450}$ or monoamine oxidase isoform by a compound as disclosed herein is decreased; or metabolism of the compound as disclosed herein by at least one polymorphically-expressed cytochrome $P_{450}$ isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using the methods described by Li et al. *Rapid Communications in Mass Spectrometry* 2005, 19, 1943-1950; Paniagua et al., *Therapeutic Drug Monitoring* 2005, 27(5), 608-616; Lawendy et al., *J Clin Pharmacol* 2009, 49, 423-429; and any references cited therein and any modifications made thereof.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

The inhibition of the cytochrome $P_{450}$ isoform is measured by the method of Ko et al., *British Journal of Clinical Pharmacology* 2000, 49, 343-351. The inhibition of the $MAO_A$ isoform is measured by the method of Weyler et al., *J. Biol. Chem.* 1985, 260, 13199-13207. The inhibition of the $MAO_B$ isoform is measured by the method of Uebelhack et al., *Pharmacopsychiatry*, 1998, 31, 187-192.

Examples of polymorphically-expressed cytochrome $P_{450}$ isoforms in a mammalian subject include, but are not limited to, CYP2C8, CYP2C9, CYP2C19, and CYP2D6.

The metabolic activities of liver microsomes, cytochrome $P_{450}$ isoforms, and monoamine oxidase isoforms are measured by the methods described herein.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", $4^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds disclosed herein may also be combined or used in combination with other agents useful in the treatment of Janus kinase 3-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined with one or more H+, K+ ATPase inhibitors, alimentary motility modulator, non-steroidal anti-inflammatory agents, anilide analgesics, anti-rheumatic agents, glucocorticoids, and immunosuppressants.

In certain embodiments, the compounds disclosed herein can be combined with one or more H+, K+ ATPase inhibitors, including, but not limited to, esomeprazole, lansoprazole, omeprazole, pantoprazole, rabeprazole, and tenatoprazole.

In certain embodiments, the compounds disclosed herein can be combined with one or more alimentary motility modulators, including, but not limited to, solabegron, tegaserod, alosetron, cilansetron, domperidone, metoclopramide, itopride, cisapride, renzapride, zacopride, octreotide, naloxone, erythromycin, and bethanechol.

In certain embodiments, the compounds disclosed herein can be combined with one or more non-steroidal anti-inflammatory agents, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoracoxib, faislamine, fenbuten, fenoprofen, flurbiprofen, ibuprofen, indometacin, ketoprofen, ketorolac, lornoxicam, loxoprofen, lumiracoxib, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinprazone, suprofen, tenoxicam, tiaprofenic acid, and tolmetin.

In certain embodiments, the compounds disclosed herein can be combined with one or more anilide analgesics, including, but not limited to, acetaminophen and phenacetin.

In certain embodiments, the compounds disclosed herein can be combined with one or more disease-modifying anti-rheumatic agents, including, but not limited to, azathioprine, cyclosporine A, D-penicillamine, gold salts, hydroxychloroquine, leflunomide, methotrexate, minocycline, sulfasalazine, cyclophosphamide, etanercept, infliximab, adalimumab, anakinra, rituximab, and abatacept.

In certain embodiments, the compounds disclosed herein can be combined with one or more glucocorticoids, including, but not limited to, beclometasone, budesonide, flunisolide, betamethasone, fluticasone, triamcinolone, mometasone, ciclesonide, hydrocortisone, cortisone acetate, prednisone, prednisolone, methylprednisolone, and dexamethasone.

In certain embodiments, the compounds disclosed herein can be combined with one or more immunosuppressants, including, but not limited to, fingolimod, cyclosporine A, Azathioprine, dexamethasone, tacrolimus, sirolimus, pimecrolimus, mycophenolate salts, everolimus, basiliximab, daclizumab, anti-thymocyte globulin, anti-lymphocyte globulin, and CTLA4IgG.

The compounds disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiazolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as estrogens/antiestrogens, androgens/antiandrogens, progestins, and luteinizing hormone-releasing hormone anatagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; topoisomerase inhibitors; prenyl-protein transferase inhibitors; cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating Janus kinase 3-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of Janus kinase 3-mediated disorders.

General Synthetic Methods for Preparing Compounds

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds as disclosed herein can be prepared by methods known to one of skill in the art and routine modifications thereof, and/or following procedures similar to those described in the Example section herein and routine modifications thereof, and/or procedures found in Jiang et al., *J. Med. Chem.* 2008, 51, 8012-8018; U.S. Pat. No. 6,627,754; WO 2003/048162; WO 2007/012953, which are hereby incorporated in their entirety, and references cited therein and routine modifications thereof. Compounds as disclosed herein can also be prepared as shown in any of the following schemes and routine modifications thereof.

The following schemes can be used to practice the present invention. Any position shown as hydrogen may optionally be replaced with deuterium.

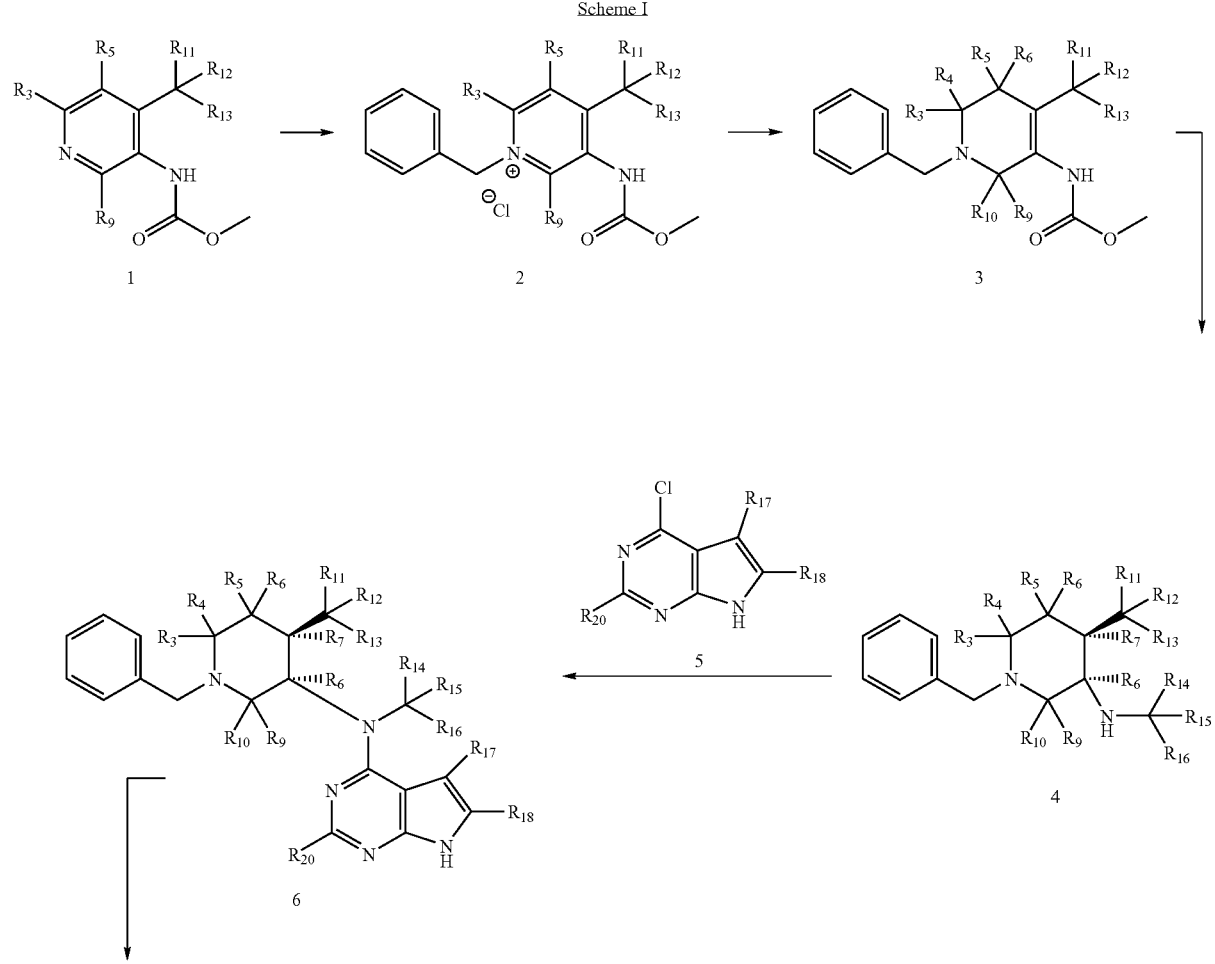

Scheme I

-continued

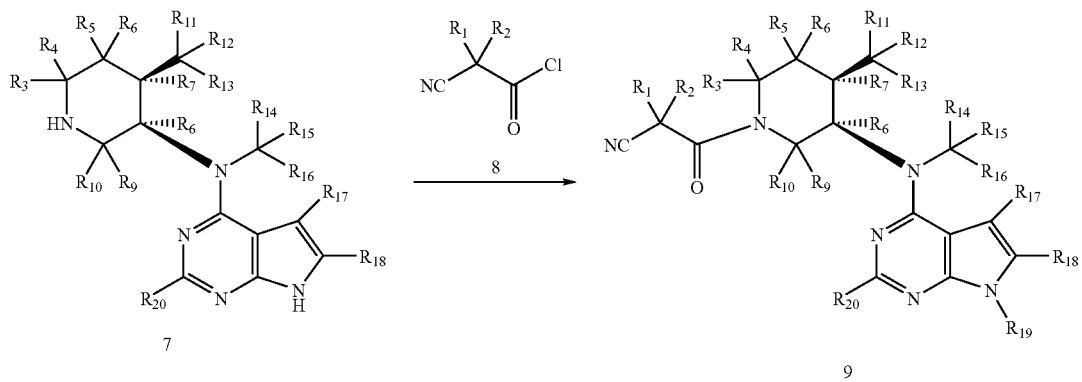

7

8

9

Compound 1 is reacted with benzyl chloride in an appropriate solvent, such as toluene, to give compound 2. Compound 2 is reacted with an appropriate reducing reagent, such as sodium borohydride, in an appropriate solvent, such as ethanol, to give compound 3. Compound 3 is reacted with an appropriate reducing agent, such as hydrogen gas, in the presence of appropriate chiral rhodium catalyst, such as a combination of bis(1,5-cyclooctadiene)rhodium (I) trifluoromethanesulfonate and (R)-(−)-1-[(S)-2-(diphenylphosphino)ferrocenyl]ethyl-di-t-butylphosphine, in an appropriate solvent, such as ethanol, to give compound 4. Compound 4 can be optionally crystallized with an appropriate chiral acid, such as L-di-p-toluoyl tartaric acid, to give increased enantiomeric purity. Compound 4 is reacted with compound 5 in the presence of an appropriate base, such as potassium carbonate, in an appropriate solvent, such as water, to give compound 6. Compound 6 is reacted with an appropriate reducing agent, such as hydrogen gas, in the presence of an appropriate catalyst, such as palladium hydroxide on carbon, in an appropriate solvent, such as water, to give compound 7. Compound 7 is reacted with compound 8, in the presence of an appropriate base, such as triethylamine, in an appropriate solvent, such as dichloromethane, to give a compound 9 of Formula I.

Deuterium can be incorporated to different positions synthetically, according to the synthetic procedures as shown in Scheme I, by using appropriate deuterated intermediates. For example, to introduce deuterium at one or more positions of $R_3$, $R_5$, $R_9$, and $R_{11}$-$R_{13}$, compound 1 with the corresponding deuterium substitutions can be used. To introduce deuterium at $R_4$, $R_6$, and $R_{10}$, sodium borodeuteride and $d_5$-ethanol can be used. To introduce deuterium at one or more positions of $R_7$-$R_8$ and $R_{14}$-$R_{16}$, deuterium gas can be used. To introduce deuterium at one or more positions of $R_{17}$-$R_{18}$ and $R_{20}$, compound 5 with the corresponding deuterium substitutions can be used. To introduce deuterium at one or more positions of $R_1$-$R_2$, compound 8 with the corresponding deuterium substitutions can be used.

Deuterium can be incorporated to various positions having an exchangeable proton, such as the heterocyclic N—H, via proton-deuterium equilibrium exchange. For example, to introduce deuterium at $R_{19}$, this proton may be replaced with deuterium selectively or non-selectively through a proton-deuterium exchange method known in the art.

Scheme II

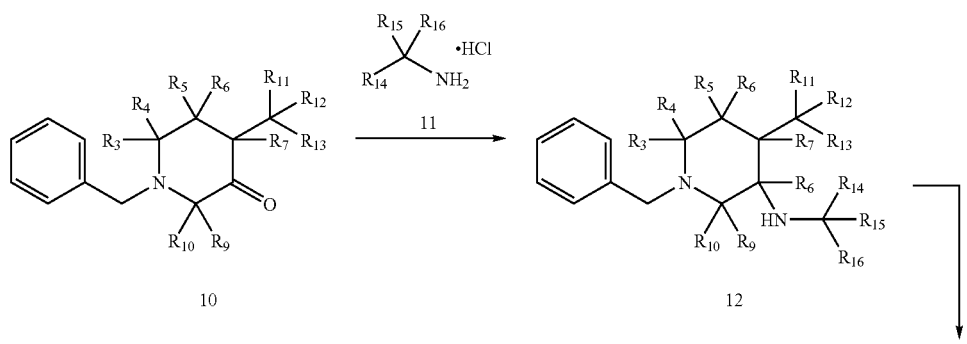

10

11

12

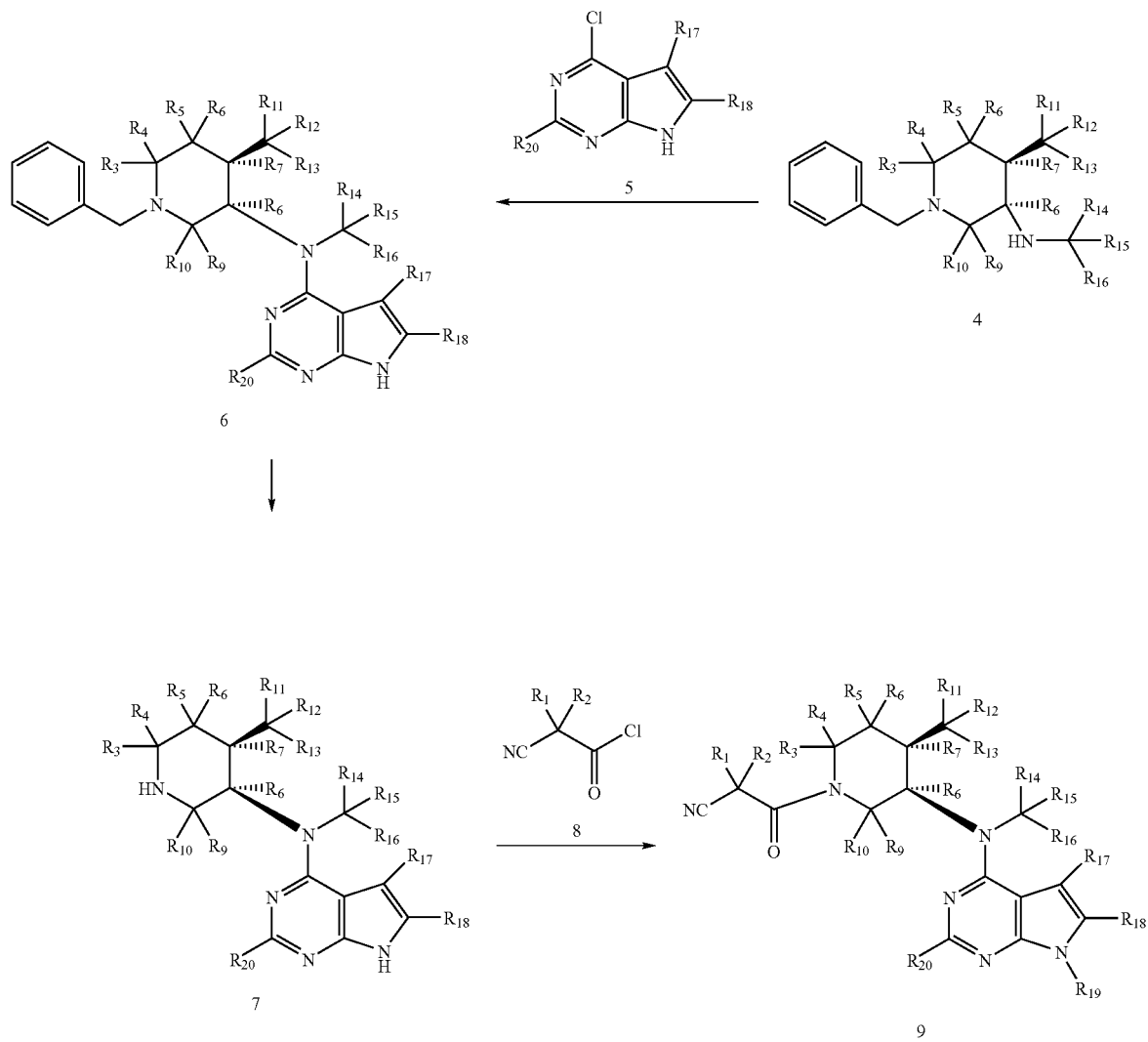

Compound 10 is reacted with compound 11, in the presence of an appropriate reducing agent, such as sodium triacetoxyborohydride, in an appropriate solvent, such as tetrahydrofuran, to give compound 12. Compound 12 is crystallized with an appropriate chiral acid, such as L-di-p-toluoyltartaric acid, to give compound 4. Compound 4 is reacted with compound 5, in the presence of an appropriate base, such as potassium carbonate, in an appropriate solvent, such as water, to give compound 6. Compound 6 is reacted with an appropriate reducing agent, such as hydrogen gas, in the presence of an appropriate catalyst, such as palladium hydroxide on carbon, in an appropriate solvent, such as water, to give compound 7. Compound 7 is reacted with compound 8, in the presence of an appropriate base, such as triethylamine, in an appropriate solvent, such as dichloromethane, to give a compound 9 of Formula I.

Deuterium can be incorporated to different positions synthetically, according to the synthetic procedures as shown in Scheme II, by using appropriate deuterated intermediates. For example, to introduce deuterium at one or more positions of $R_3$-$R_7$ and $R_9$-$R_{13}$, compound 10 with the corresponding deuterium substitutions can be used. To introduce deuterium at $R_8$, sodium triacetoxyborodeuteride can be used. To introduce deuterium at one or more positions of $R_{17}$-$R_{18}$ and $R_{20}$, compound 5 with the corresponding deuterium substitutions can be used. To introduce deuterium at one or more positions of $R_1$-$R_2$, compound 8 with the corresponding deuterium substitutions can be used.

Deuterium can be incorporated to various positions having an exchangeable proton, such as the heterocyclic N—H, via proton-deuterium equilibrium exchange. For example, to introduce deuterium at $R_{19}$, this proton may be replaced with deuterium selectively or non-selectively through a proton-deuterium exchange method known in the art.

Scheme III

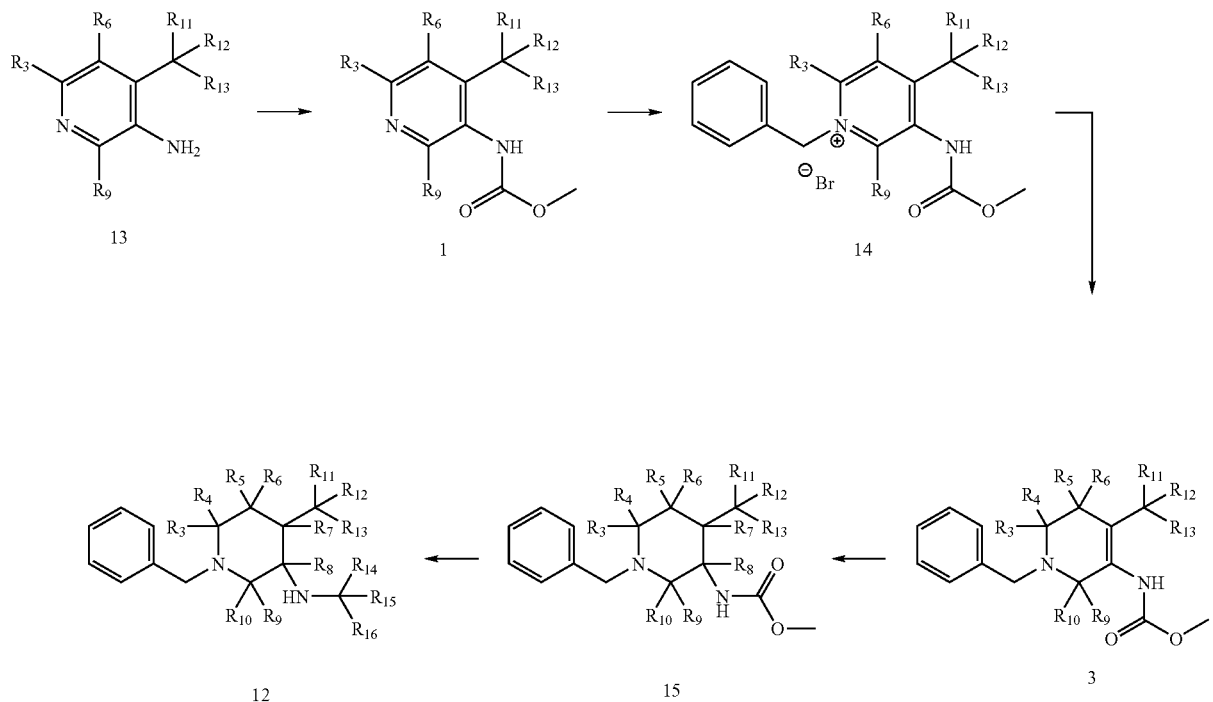

Compound 13 is reacted with an appropriate amine protecting reagent, such as dimethyl carbonate, in the presence of an appropriate base, such as sodium hexamethyldisilazide, in an appropriate solvent, such as tetrahydrofuran, to give compound 1. Compound 1 is reacted with benzyl bromide in an appropriate solvent, such as toluene, at elevated temperature, to give compound 14. Compound 14 is reacted with an appropriate reducing agent, such as sodium borohydride, in an appropriate solvent, such as ethanol, to give compound 3. Compound 3 is reacted with an appropriate reducing agent, such as hydrogen gas, in the presence of an appropriate catalyst, such as platinum oxide, in an appropriate solvent, such as methanol, to give compound 15. Compound 15 is reacted with an appropriate reducing agent, such as lithium aluminum hydride, in an appropriate solvent, such as tetrahydrofuran, to give compound 12.

Deuterium can be incorporated to different positions synthetically, according to the synthetic procedures as shown in Scheme III, by using appropriate deuterated intermediates. For example, to introduce deuterium at one or more positions of $R_3$, $R_6$, $R_9$, and $R_{11}$-$R_{13}$, compound 13 with the corresponding deuterium substitutions can be used. To introduce deuterium at $R_4$-$R_5$ and $R_{10}$, sodium borodeuteride can be used. To introduce deuterium at one or more positions of $R_7$-$R_8$, deuterium gas and/or $d_4$-methanol can be used.

Scheme IV

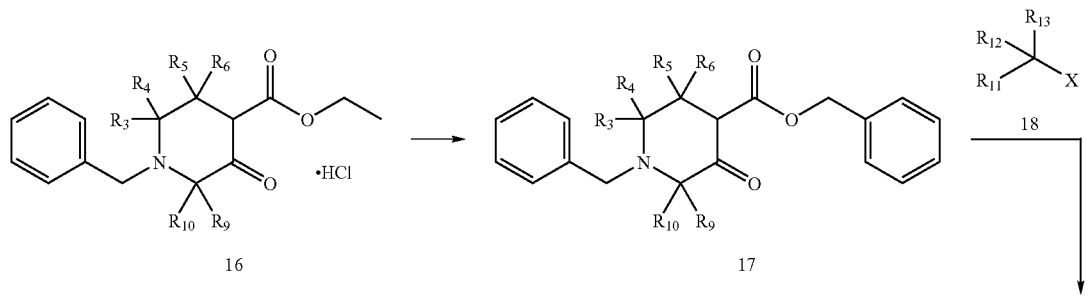

-continued

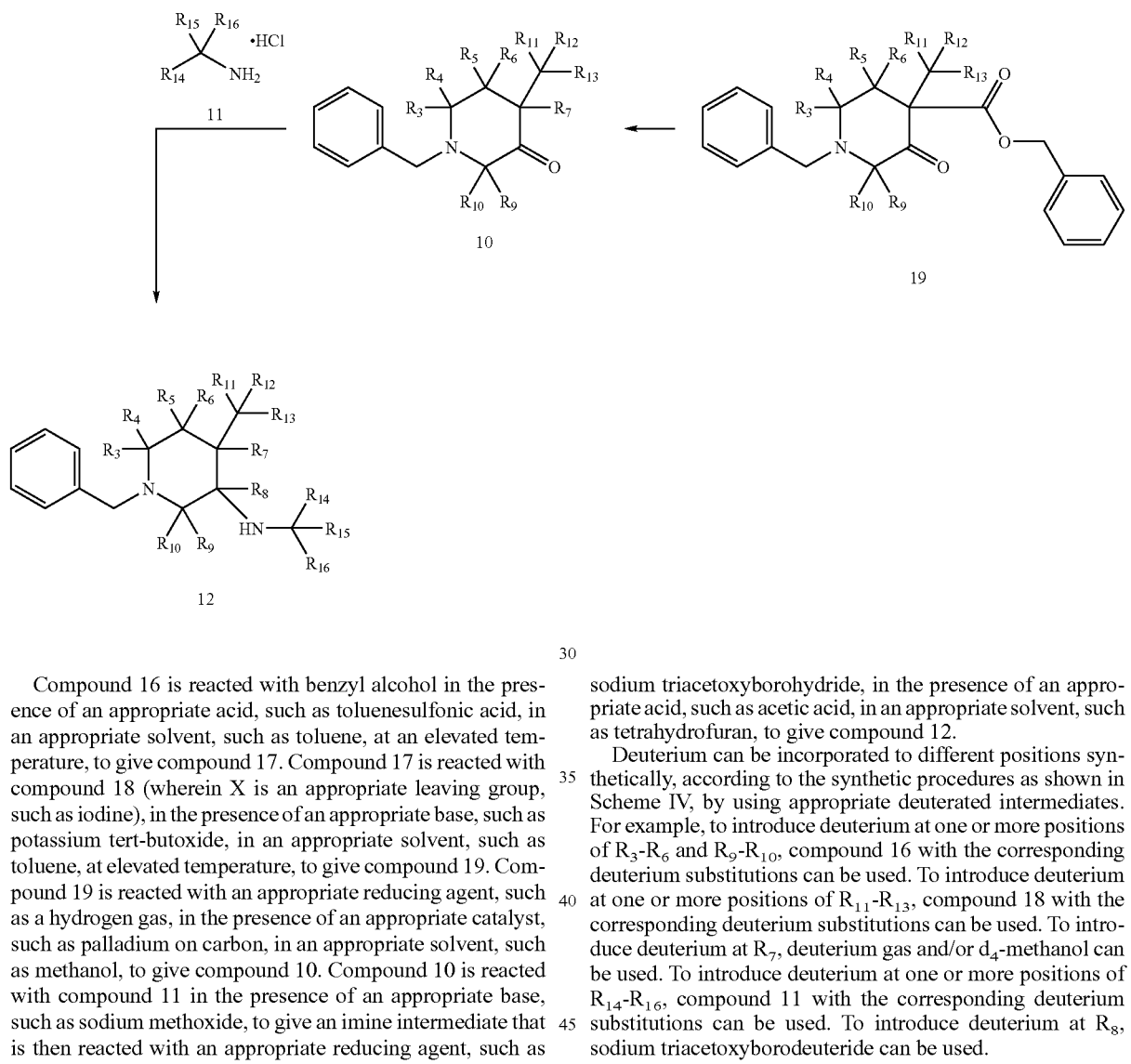

Compound 16 is reacted with benzyl alcohol in the presence of an appropriate acid, such as toluenesulfonic acid, in an appropriate solvent, such as toluene, at an elevated temperature, to give compound 17. Compound 17 is reacted with compound 18 (wherein X is an appropriate leaving group, such as iodine), in the presence of an appropriate base, such as potassium tert-butoxide, in an appropriate solvent, such as toluene, at elevated temperature, to give compound 19. Compound 19 is reacted with an appropriate reducing agent, such as a hydrogen gas, in the presence of an appropriate catalyst, such as palladium on carbon, in an appropriate solvent, such as methanol, to give compound 10. Compound 10 is reacted with compound 11 in the presence of an appropriate base, such as sodium methoxide, to give an imine intermediate that is then reacted with an appropriate reducing agent, such as sodium triacetoxyborohydride, in the presence of an appropriate acid, such as acetic acid, in an appropriate solvent, such as tetrahydrofuran, to give compound 12.

Deuterium can be incorporated to different positions synthetically, according to the synthetic procedures as shown in Scheme IV, by using appropriate deuterated intermediates. For example, to introduce deuterium at one or more positions of $R_3$-$R_6$ and $R_9$-$R_{10}$, compound 16 with the corresponding deuterium substitutions can be used. To introduce deuterium at one or more positions of $R_{11}$-$R_{13}$, compound 18 with the corresponding deuterium substitutions can be used. To introduce deuterium at $R_7$, deuterium gas and/or $d_4$-methanol can be used. To introduce deuterium at one or more positions of $R_{14}$-$R_{16}$, compound 11 with the corresponding deuterium substitutions can be used. To introduce deuterium at $R_8$, sodium triacetoxyborodeuteride can be used.

Scheme V

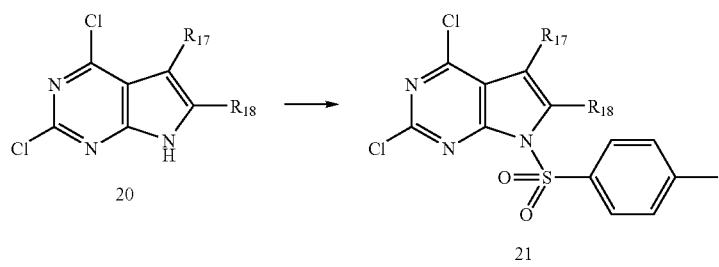

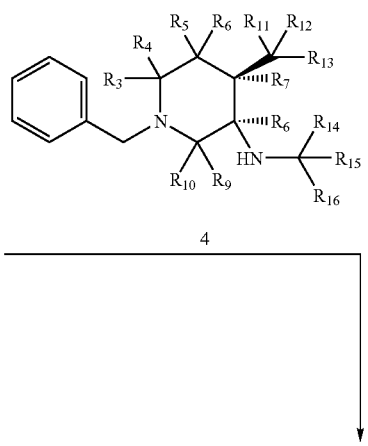

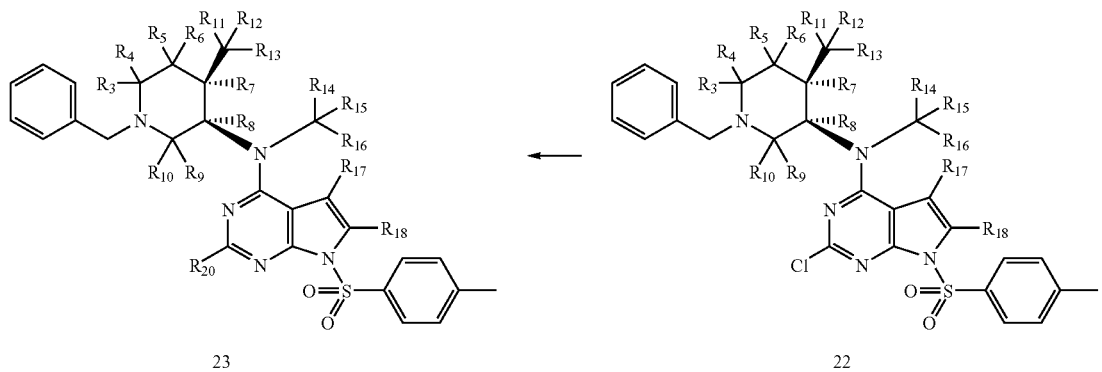

Compound 20 is reacted with toluenesulfonyl chloride in the presence of an appropriate base, such as sodium hydroxide, in an appropriate solvent, such as an appropriate mixture of acetone and water, to give compound 21. Compound 21 is reacted with compound 4 in the presence of an appropriate base, such as potassium carbonate, in an appropriate solvent, such as an appropriate mixture of tetrahydrofuran and water, to give compound 22. Compound 22 is reacted with an appropriate reducing agent, such as hydrogen gas, in the presence of an appropriate catalyst, such as palladium on carbon, in the presence of an appropriate base, such as magnesium oxide, in an appropriate solvent, such as water, to give compound 23.

Deuterium can be incorporated to different positions synthetically, according to the synthetic procedures as shown in Scheme V, by using appropriate deuterated intermediates. For example, to introduce deuterium at one or more positions of $R_{17}$-$R_{18}$, compound 20 with the corresponding deuterium substitutions can be used. To introduce deuterium at one or more positions of $R_3$-$R_{16}$, compound 4 with the corresponding deuterium substitutions can be used. To introduce deuterium at $R_{20}$ deuterium gas and/or deuterium oxide can be used.

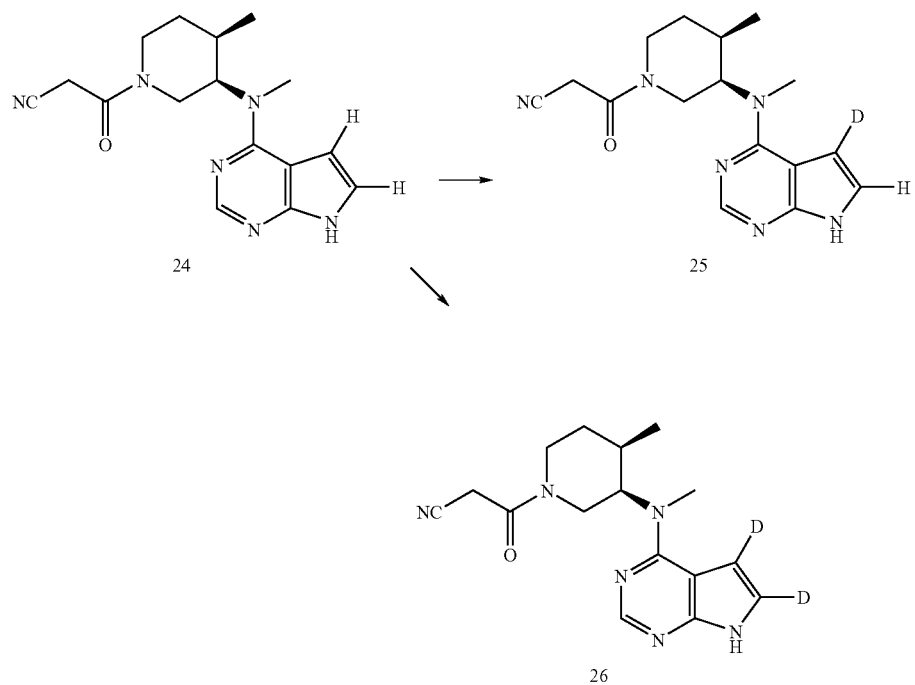

Compound 24 is reacted with $d_4$-methanol and $d_3$-sodium methoxide at about 120° C. for about 16 hours to give compound 25. Compound 24 is reacted with $d_4$-methanol and $d_3$-sodium methoxide at about 160° C. for about 16 hours to give compound 26.
Scheme VII
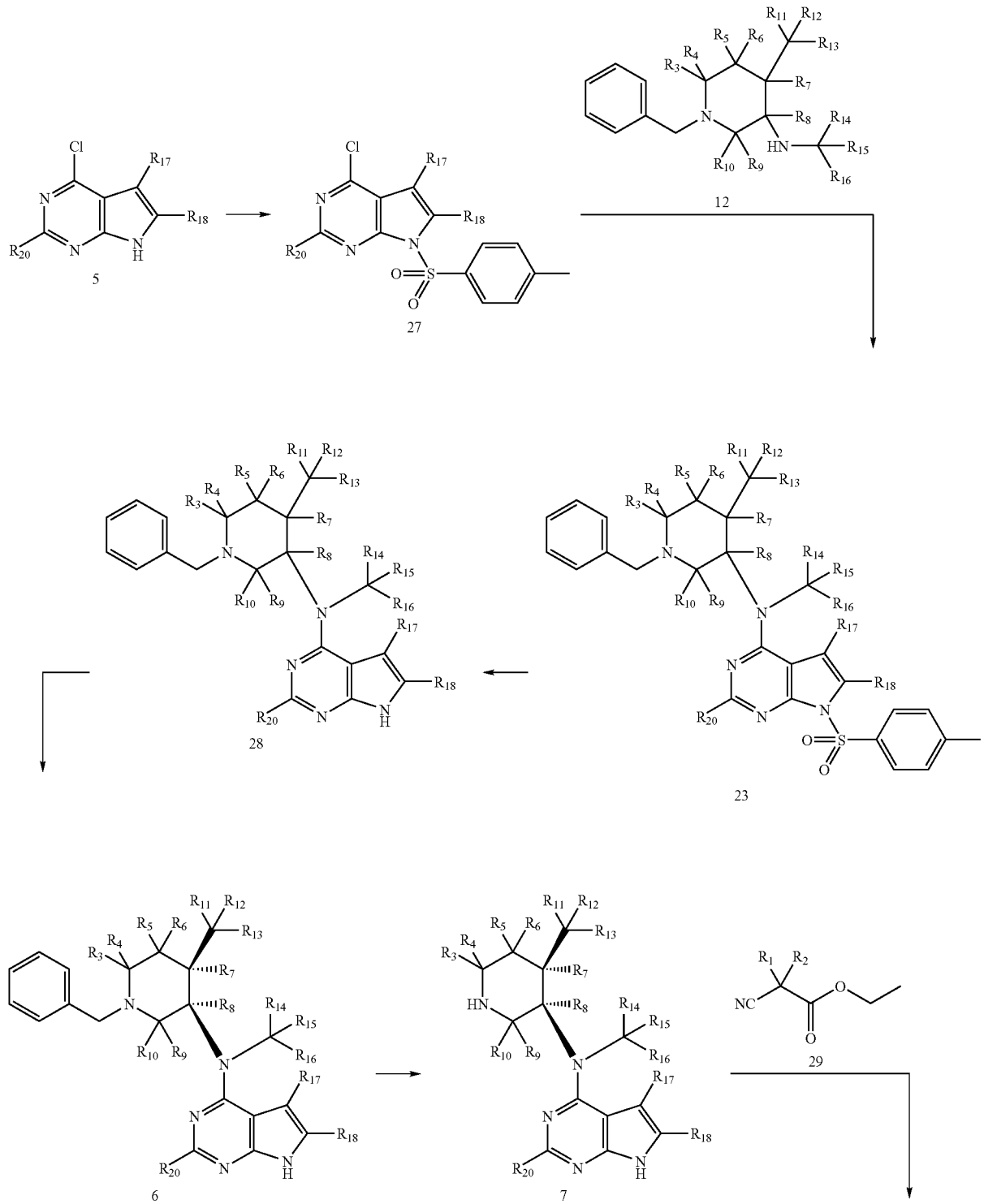

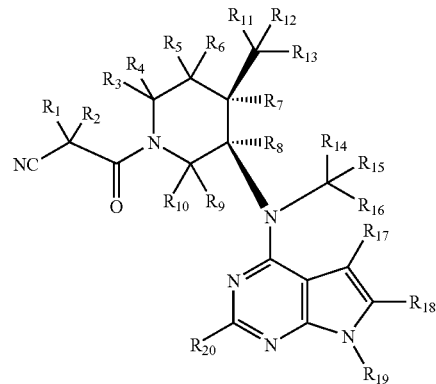

9

Compound 5 is reacted with toluenesulfonyl chloride in the presence of an appropriate base, such as sodium hydroxide, in an appropriate solvent, such as an appropriate mixture of acetone and water, to give compound 27. Compound 27 is reacted with compound 12 in the presence of an appropriate base, such as potassium carbonate, in an appropriate solvent, such as an appropriate mixture of tetrahydrofuran and water, to give compound 23. Compound 23 is reacted with an appropriate base, such as sodium hydroxide, in an appropriate solvent, such as water, to give compound 28. Compound 28 is resolved using chiral chromatography, with an appropriate column, such as Chiralpak IA, using an appropriate eluent, such as hexane (containing 0.1% triethylamine)/isopropanol, to give compound 6. Compound 6 is reacted with an appropriate reducing agent, such as hydrogen gas, in the presence of an appropriate catalyst, such as palladium on carbon, in the presence of an appropriate acid, such as acetic acid, in an appropriate solvent, such as a combination of isopropanol and water, to give compound 7. Compound 7 is reacted with compound 29 in the presence of an appropriate base, such as triethylamine, in an appropriate solvent, such as toluene, to give compound 9.

Deuterium can be incorporated to different positions synthetically, according to the synthetic procedures as shown in Scheme VII, by using appropriate deuterated intermediates. For example, to introduce deuterium at one or more positions of $R_{17}$-$R_{18}$ and $R_{20}$, compound 5 with the corresponding deuterium substitutions can be used. To introduce deuterium at one or more positions of $R_3$-$R_{16}$, compound 12 with the corresponding deuterium substitutions can be used. To introduce deuterium at $R_1$-$R_2$, compound 29 with the corresponding deuterium substitutions can be used.

Deuterium can be incorporated to various positions having an exchangeable proton, such as the heterocyclic N—H, via proton-deuterium equilibrium exchange. For example, to introduce deuterium at $R_{19}$, this proton may be replaced with deuterium selectively or non-selectively through a proton-deuterium exchange method known in the art.

Scheme VIII

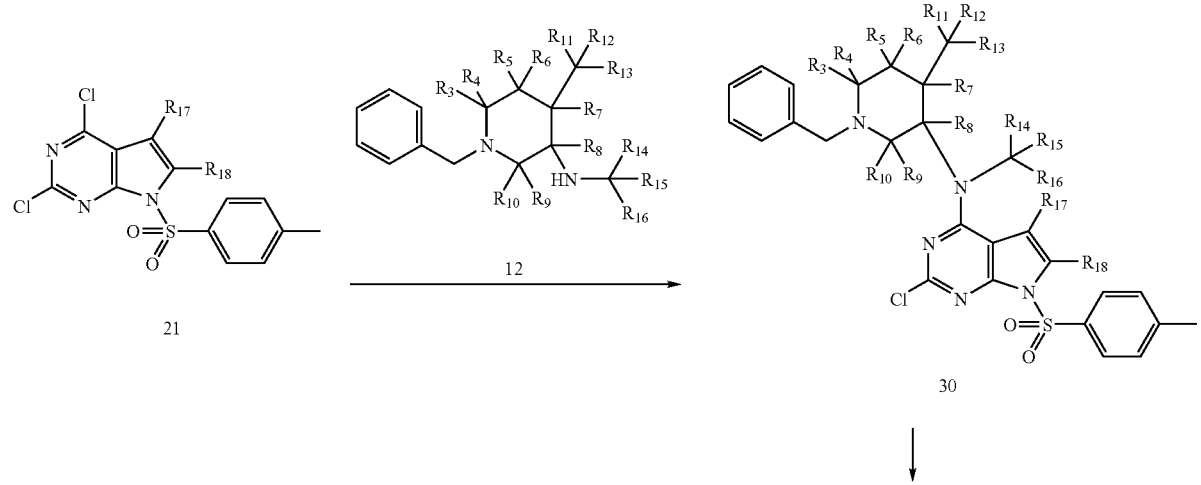

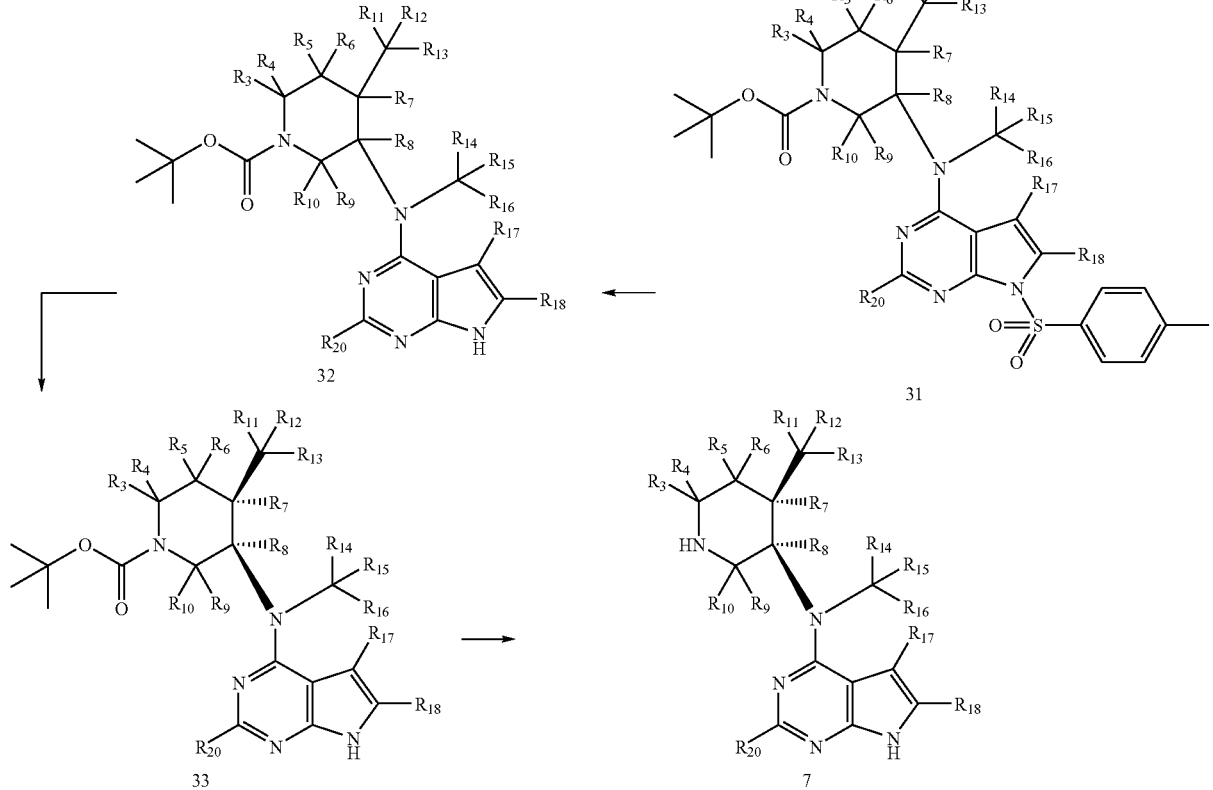

Compound 21 is reacted with compound 12 in the presence of an appropriate base, such as potassium carbonate, in an appropriate solvent, such as an appropriate mixture of tetrahydrofuran and water, to give compound 30. Compound 30 is reacted with an appropriate reducing agent, such as hydrogen gas, in the presence of an appropriate catalyst, such as palladium hydroxide on carbon, in the presence of an appropriate protecting agent, such as di-tert-butyl dicarbonate, in an appropriate solvent, such as a combination of methanol and water, to give compound 31. Compound 31 is reacted with an appropriate base, such as sodium hydroxide, in an appropriate solvent, such as water, to give compound 32. Compound 32 is resolved using chiral chromatography, with an appropriate column, such as Chiralpak IA, using an appropriate eluent, such as hexane (containing 0.1% triethylamine)/isopropanol, to give compound 33. Compound 33 is reacted with an appropriate acid, such as hydrogen chloride, in an appropriate solvent, such as 1,4-dioxane, to give compound 7.

Deuterium can be incorporated to different positions synthetically, according to the synthetic procedures as shown in Scheme VIII, by using appropriate deuterated intermediates. For example, to introduce deuterium at one or more positions of $R_{17}$-$R_{18}$, compound 21 with the corresponding deuterium substitutions can be used. To introduce deuterium at one or more positions of $R_3$-$R_{16}$, compound 12 with the corresponding deuterium substitutions can be used. To introduce deuterium at $R_{20}$, deuterium gas and/or $d_4$-methanol can be used.

Scheme IX

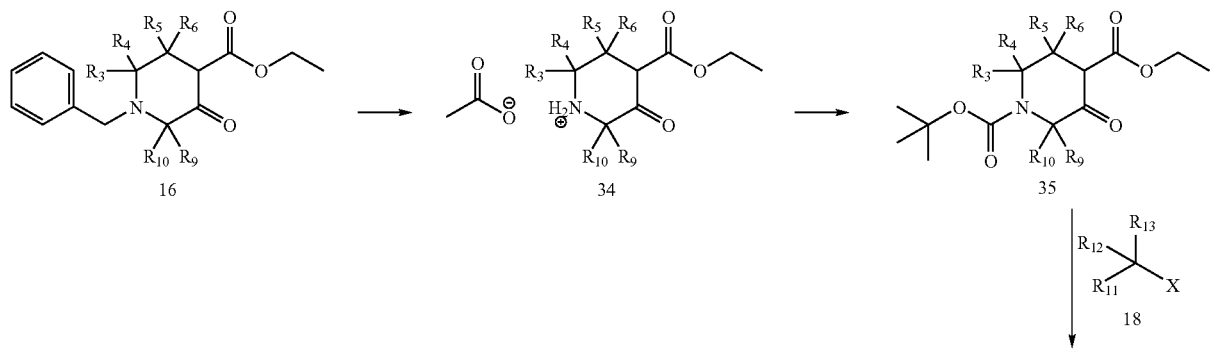

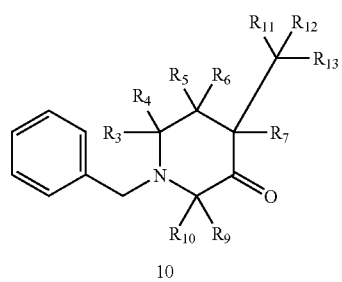
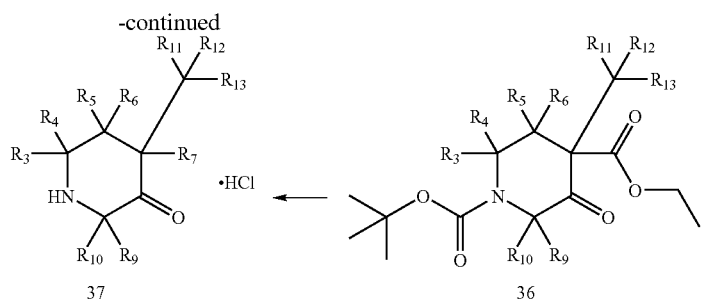

Compound 16 is reacted with an appropriate reducing agent, such as hydrogen gas and an appropriate catalyst, such as palladium on carbon, in the presence of an appropriate acid, such as acetic acid, in an appropriate solvent, such as methanol, to give compound 34. Compound 34 is reacted with an appropriate protecting agent, such as di-tert-butyl dicarbonate, in the presence of an appropriate base, such as potassium carbonate, in an appropriate solvent, such as tetrahydrofuran, to give compound 35. Compound 35 is reacted with compound 18 (wherein X is an appropriate leaving group, such as iodine), in the presence of an appropriate base, such as sodium hydride, in an appropriate solvent, such as tetrahydrofuran, at elevated temperature, to give compound 36. Compound 36 is reacted with an appropriate acid, such as hydrochloric acid, in an appropriate solvent, such as water, to give compound 37. Compound 37 is reacted with an appropriate protecting agent, such as benzyl bromide, in the presence of an appropriate base, such as triethylamine, to give compound 10.

Deuterium can be incorporated to different positions synthetically, according to the synthetic procedures as shown in Scheme IX, by using appropriate deuterated intermediates. For example, to introduce deuterium at one or more positions of $R_3$-$R_6$ and $R_9$-$R_{10}$, compound 16 with the corresponding deuterium substitutions can be used. To introduce deuterium at one or more positions of $R_{11}$-$R_{13}$, compound 18 with the corresponding deuterium substitutions can be used. To introduce deuterium at $R_7$, deuterium chloride and/or deuterium oxide can be used.

Scheme X

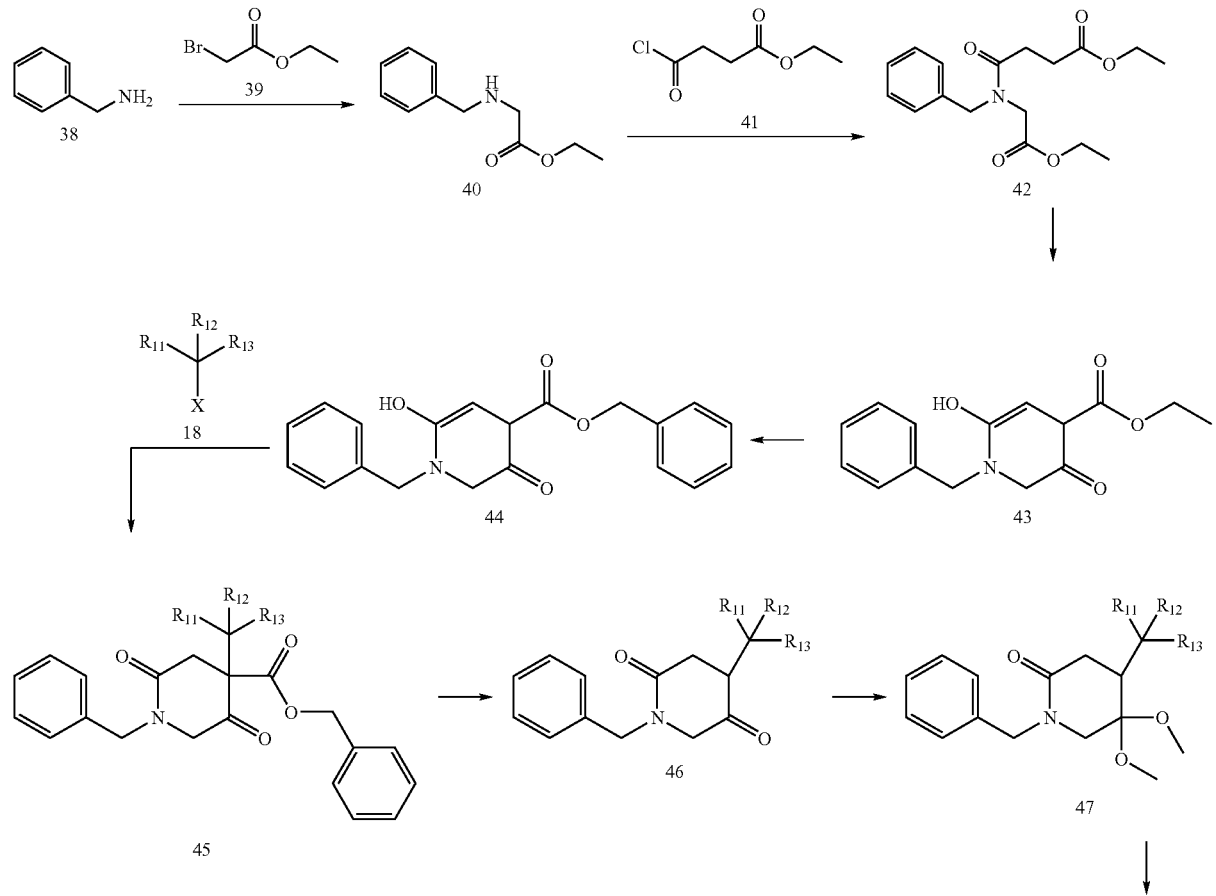

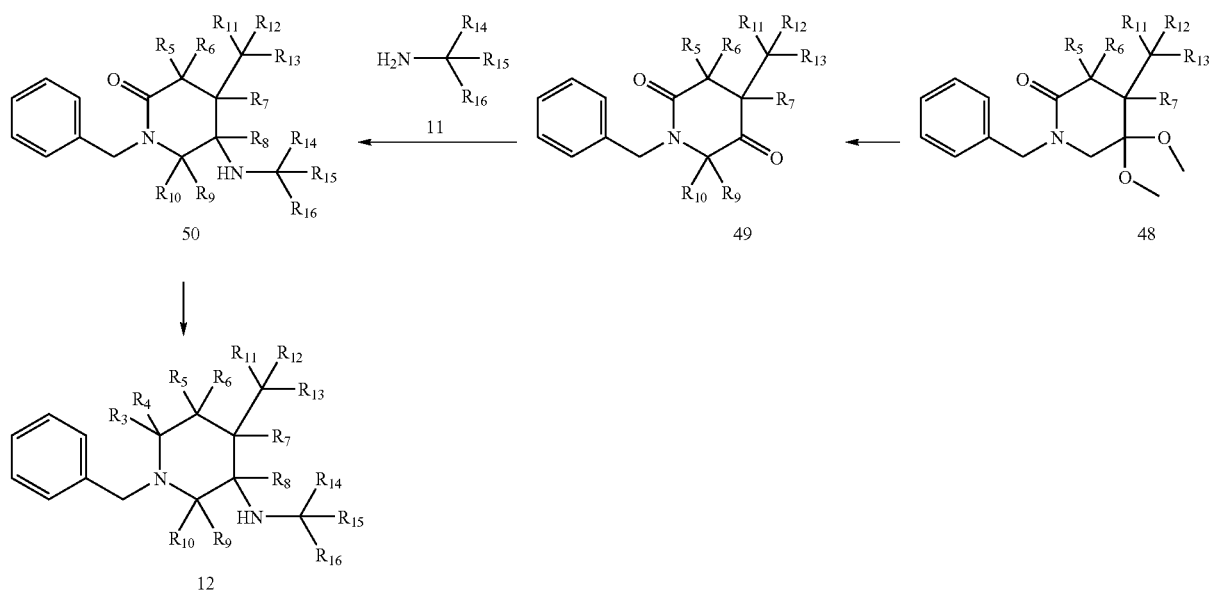

Compound 38 is reacted with compound 39 in the presence of an appropriate base, such as diisopropylethylamine, to give compound 40. Compound 40 is reacted with compound 41 in the presence of an appropriate base, such as potassium carbonate, in an appropriate solvent, such as a combination of water and tetrahydrofuran, to give compound 42. Compound 42 is reacted with an appropriate base, such as sodium ethoxide, in an appropriate solvent, such as a combination of ethanol and 1,4-dioxane, to give compound 43. Compound 43 is reacted with benzyl alcohol at elevated temperature to give compound 44. Compound 44 is reacted with compound 18 (wherein X is an appropriate leaving group, such as iodine), in the presence of an appropriate base, such as potassium carbonate, in an appropriate solvent, such as acetone, at elevated temperature, to give compound 45. Compound 45 is reacted with an appropriate reducing agent, such as hydrogen and an appropriate catalyst, such as palladium on carbon, in an appropriate solvent, such as ethyl acetate, to give compound 46. Compound 46 is reacted with an appropriate dehydrating agent agent, such as trimethyl orthoformate, in the presence of an appropriate acid, such as toluenesulfonic acid, in an appropriate solvent, such as methanol, to give compound 47. Compound 47 is reacted with an appropriate base, such as sodium hydroxide, in an appropriate solvent, such as a combination of water and methanol, to give compound 48. Compound 48 is reacted with an appropriate acid, such as hydrochloric acid, in an appropriate solvent, such as water, to give compound 49. Compound 49 is reacted with compound 11 in the presence of an appropriate acid, such as acetic acid, and an appropriate reducing agent, such as triacetoxyborohydride, in an appropriate solvent, such as tetrahydrofuran, to give compound 50. Compound 50 is reacted with an appropriate reducing agent, such as lithium aluminum hydride, in an appropriate solvent, such as tetrahydrofuran, to give compound 12.

Deuterium can be incorporated to different positions synthetically, according to the synthetic procedures as shown in Scheme X, by using appropriate deuterated intermediates. For example, to introduce deuterium at one or more positions of $R_{11}$-$R_{13}$, compound 18 with the corresponding deuterium substitutions can be used. To introduce deuterium at $R_5$-$R_7$, $d_1$-sodium hydroxide, deuterium oxide, and/or $d_4$-methanol can be used. To introduce deuterium at $R_9$-$R_{10}$, deuterium chloride and/or deuterium oxide can be used. To introduce deuterium at $R_8$, sodium triacetoxyborodeuteride can be used. To introduce deuterium at $R_3$-$R_4$, lithium aluminum deuteride can be used. To introduce deuterium at one or more positions of $R_{14}$-$R_{16}$, compound 18 with the corresponding deuterium substitutions can be used.

The invention is further illustrated by the following examples. All IUPAC names were generated using CambridgeSoft's ChemDraw 10.0.

EXAMPLE 1

3-((3R,4R)-4-Methyl-3-(methyl(7H-pyrrolo[2,3-d]pyrimidin-4-yl)amino)piperidin-1-yl)-3-oxopropanenitrile Mono Citrate Salt (CP-690550 Citrate Salt)

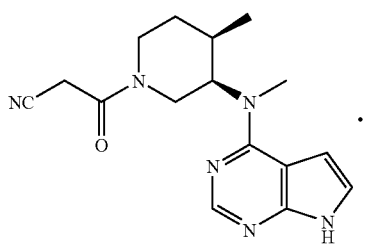

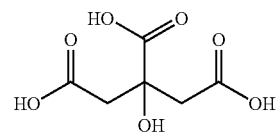

Step 1

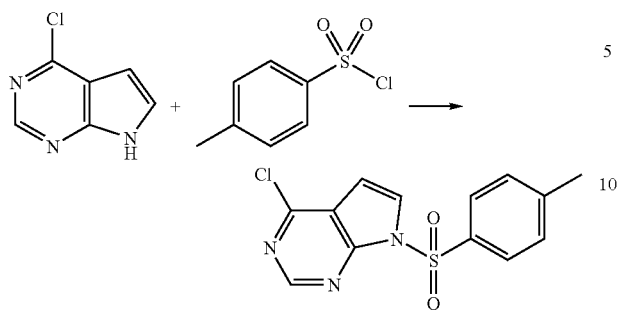

4-Chloro-7-tosyl-7H-pyrrolo[2,3-d]pyrimidine

At about 0° C., sodium hydroxide (2 mol/L in water, 8 mL, 1.20 equiv.) was added to a solution of 4-methylbenzene-1-sulfonyl chloride (2.7 g, 13.9 mmol, 1.10 equiv.) and 4-chloro-7H-pyrrolo[2,3-d]pyrimidine (2 g, 12.8 mmol, 1.00 equiv.) in acetone (20 mL). The resulting solution was stirred at about 20° C. for about 6 hours. The solids were collected by filtration and washed with acetone/water to give the title product as a white solid (4.0 g; yield=97%). $^1$H NMR (300 MHz, CDCl$_3$) δ: 8.78 (s, 1H), 8.11 (d, J=8.4 Hz, 2H), 7.80 (d, J=4.2 Hz, 1H), 7.34 (d, J=8.4 Hz, 2H), 7.73 (d, J=4.2 Hz, 1H), 2.42 (s, 3H). LC-MS: m/z=308/310 (M+H)$^+$.

Step 2

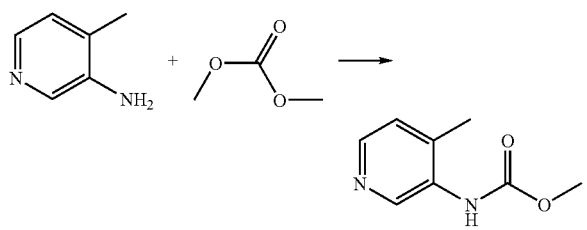

Methyl 4-methylpyridin-3-ylcarbamate

At about 0° C., potassium tert-butoxide (47 g, 420 mmol, 3.00 equiv.) was added in several batches to a solution of 4-methylpyridin-3-amine (15 g, 139 mmol, 1.00 equiv.) in tetrahydrofuran (400 mL). After stifling the solution for about 30 minutes, dimethyl carbonate (18.8 g, 209 mmol, 1.50 equiv.) was then added. The solution was stirred at ambient temperature for about 16 hours and then water (100 mL) was added. Following standard extractive workup with ethyl acetate (3×200 mL), the crude product was purified by recrystallization from ethyl acetate/petroleum ether (1:1) to give the title product as a pale yellow solid (17 g; yield=74%). LC-MS: m/z=167 (M+H)$^+$.

Step 3

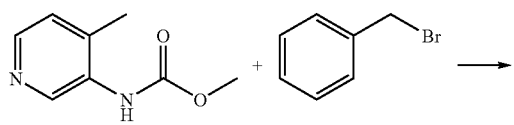

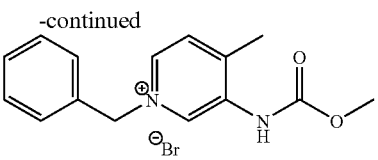

1-Benzyl-3-methoxycarbonylamino-4-methyl-pyridinium bromide 1-(Bromomethyl)benzene (19 g, 111 mmol, 1.10 equiv.) was added to a solution of methyl 4-methylpyridin-3-ylcarbamate (17 g, 102 mmol, 1.00 equiv.) in toluene (500 mL). The solution was stirred at about 110° C. for about 16 hours. After cooling to ambient temperature, the solids were collected by filtration and washed with toluene to afford the title product as a light brown solid (35 g; yield=97%).

Step 4

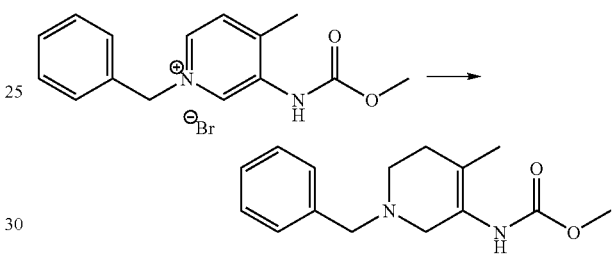

Methyl 1-benzyl-4-methyl-1,2,5,6-tetrahydropyridin-3-ylcarbamate

Sodium borohydride (4.4 g, 116 mmol, 1.20 equiv.) was added in several batches to a solution of 1-benzyl-3-methoxycarbonylamino-4-methyl-pyridinium bromide (35 g, 104 mmol, 1.00 equiv.) in methanol (300 mL). The resulting solution was stirred at ambient temperature for about 16 hours, and then water (200 mL) was added. After concentrating the mixture in vacuo, standard extractive workup with ether (3×200 mL) gave a crude residue that was then purified by silica gel column chromatography (dichloromethane/methanol (20:1)) to afford the title product as a yellow solid (18 g; yield=66%). LC-MS: m/z=261 (M+H)$^+$.

Step 5

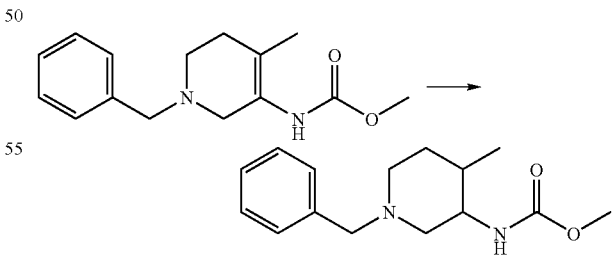

Methyl 1-benzyl-4-methylpiperidin-3-yl-carbamate

Platinum oxide (1.0 g, 4.41 mmol, 0.11 equiv.) was added to a solution of methyl 1-benzyl-4-methyl-1,2,5,6-tetrahydropyridin-3-ylcarbamate (10 g, 38.46 mmol, 1.00 equiv.) in methanol (200 mL). After introducing hydrogen gas, the mixture was stirred at about 60° C. for about 16 hours and then was filtered. The resulting filtrate was concentrated to give a crude residue that was then purified by silica gel column chromatography (ethyl acetate/petroleum (1:2)) to afford the title product a yellow solid (7 g; yield=66%). LC-MS: m/z=263 (M+H)+.

Step 6

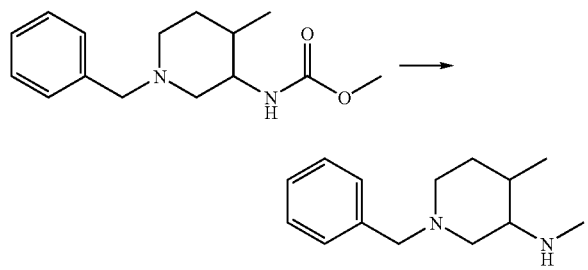

(1-Benzyl-4-methyl-piperidin-3-yl)-methyl-amine

At about 0° C., lithium aluminum hydride (3.6 g, 92.8 mmol, 5.00 equiv.) was added in several batches to a solution of methyl 1-benzyl-4-methylpiperidin-3-yl-carbamate (5.0 g, 18.1 mmol, 1.00 equiv.) in tetrahydrofuran (100 mL). The resulting solution was heated at reflux for about 16 hours, and then water (10 mL) was added. The mixture was filtered, and the resulting filtrate was concentrated in vacuo to give a crude residue that was then purified by silica gel column chromatography (dichloromethane/methanol (20:1)) to afford the title product as a yellow oil (3.0 g; yield=72%). $^1$H NMR (300 MHz, CDCl$_3$) δ: 7.20-7.38 (m, 5H), 3.58 (d, J=13.2 Hz, 1H), 3.48 (d, J=13.2 Hz, 1H), 2.60-2.82 (m, 2H), 2.46 (br s, 1H), 2.34 (s, 3H), 2.02-2.22 (m, 2H), 2.64-2.84 (m, 2H), 1.45-1.58 (m, 2H), 0.97 (d, J=6.9 Hz, 3H). LC-MS: m/z=219 (M+H)+.

Step 7

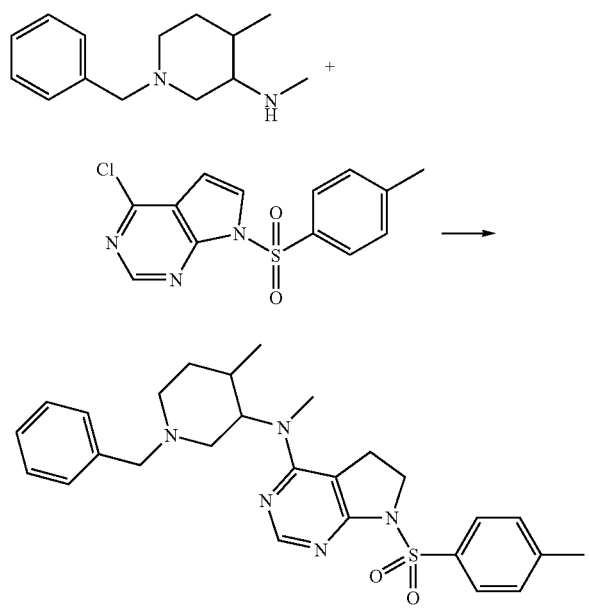

N-(1-Benzyl-4-methylpiperidin-3-yl)-N-methyl-7-tosyl-7H-pyrrolo[2,3-d]pyrimidin-4-amine 4-Chloro-7-tosyl-7H-pyrrolo[2,3-d]pyrimidine (2 g, 6.37 mmol, 2.00 equiv.) and potassium carbonate (2.7 g, 19.4 mmol, 6.00 equiv.) were added to a solution of (1-benzyl-4-methyl-piperidin-3-yl)-methyl-amine (700 mg, 2.89 mmol, 1.00 equiv.) in water (30 mL). The solution was stirred at about 100° C. for about 16 hours, and then was cooled to ambient temperature. Following standard extractive workup with ethyl acetate (3×100 mL), the crude residue was purified by silica gel column chromatography (ethyl acetate/petroleum (1:1)) to give the title product as a light yellow solid (1.5 g; yield=96%). $^1$H NMR (300 MHz, CDCl$_3$) δ: 8.36 (s, 1H), 8.08 (d, J=8.4 Hz, 2H), 7.45 (d, J=4.2 Hz, 1H), 7.20-7.42 (m, 7H), 6.75 (d, J=4.2 Hz, 1H), 5.05-5.20 (m, 1H), 3.40-3.65 (m, 5H), 2.70-2.92 (m, 2H), 2.50-2.70 (m, 1H), 2.42 (s, 3H), 2.23-2.42 (m, 1H), 2.10-2.23 (m, 1H), 1.55-1.75 (m, 2H), 0.92 (d, J=6.9 Hz, 3H). LC-MS: m/z=490 (M+H)+.

Step 8

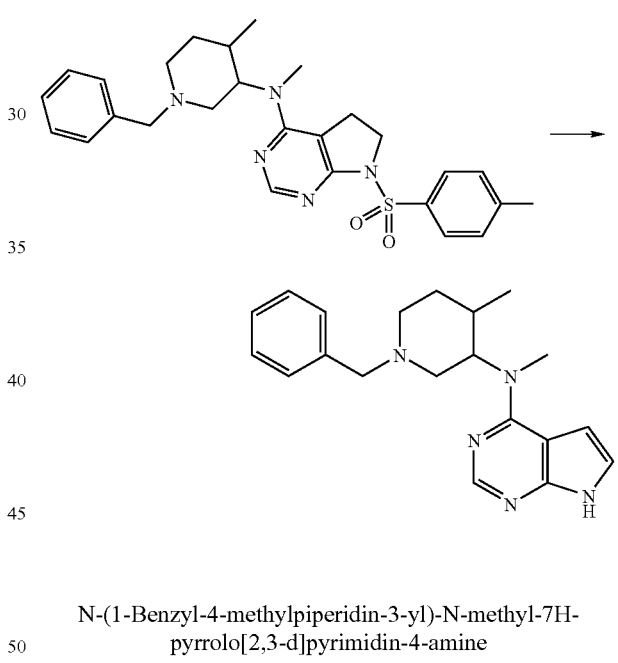

N-(1-Benzyl-4-methylpiperidin-3-yl)-N-methyl-7H-pyrrolo[2,3-d]pyrimidin-4-amine

A mixture of 50% sodium hydroxide (10 mL) and N-(1-benzyl-4-methylpiperidin-3-yl)-N-methyl-7-tosyl-7H-pyrrolo[2,3-d]pyrimidin-4-amine (400 mg, 0.80 mmol, 1.00 equiv.) was stirred at about 60° C. for about 16 hours, and then was cooled to ambient temperature. Following standard extractive workup with ethyl acetate (4×10 mL), the crude residue was then purified by silica gel column chromatography (dichloromethane/methanol (10:1)) to give the title product as a yellow solid (0.25 g; yield=88%). $^1$H NMR (300 MHz, CDCl$_3$) δ: 11.35 (br s, 1H), 8.30 (s, 1H), 7.20-7.40 (m, 5H), 7.06 (d, J=3.6 Hz, 1H), 6.60 (d, J=3.6 Hz, 1H), 5.20-5.30 (m, 1H), 3.66 (s, 3H), 3.48-3.65 (m, 2H), 2.85-2.98 (m, 1H), 2.60-2.85 (m, 2H), 2.30-2.45 (m, 1H), 2.12-2.30 (m, 1H), 1.60-1.92 (m, 2H), 0.98 (d, J=6.0 Hz, 3H). LC-MS: m/z=336 (M+H)+.

Step 9

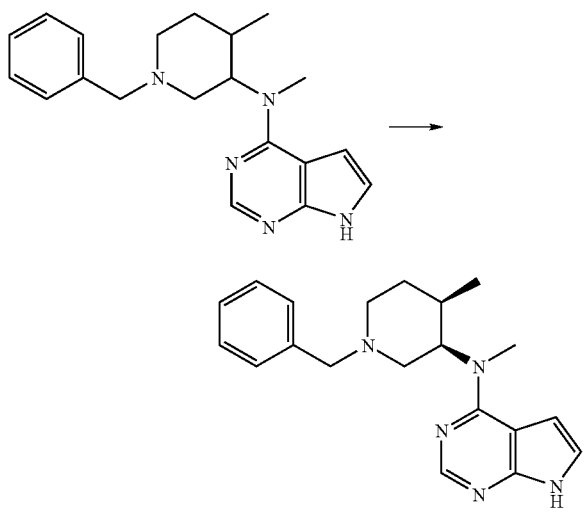

N-((3R,4R)-1-Benzyl-4-methylpiperidin-3-yl)-N-methyl-7H-pyrrolo[2,3-d]pyrimidin-4-amine The enantiomer N-((3R,4R)-1-benzyl-4-methylpiperidin-3-yl)-N-methyl-7H-pyrrolo[2,3-d]pyrimidin-4-amine (4.5 g) was isolated by chiral resolution using chiral-Prep-HPLC with the following conditions: Column: Chiralpak IA, 0.46× 25 cm; mobile phase: hexane (in 0.1% triethylamine): isopropanol (90:10); Detector: UV 254 nm. Retention time of desired enantiomer: 11.72 minutes, undesired enantiomer retention time: 7.88 minutes. ee %>99.8%. The title product was isolated a yellow solid (1.8 g; yield=40%). $^1$H NMR (300 MHz, CDCl$_3$) δ: 11.35 (br s, 1H), 8.30 (s, 1H), 7.20-7.40 (m, 5H), 7.06 (d, J=3.6 Hz, 1H), 6.60 (d, J=3.6 Hz, 1H), 5.20-5.30 (m, 1H), 3.66 (s, 3H), 3.48-3.65 (m, 2H), 2.85-2.98 (m, 1H), 2.60-2.85 (m, 2H), 2.30-2.45 (m, 1H), 2.12-2.30 (m, 1H), 1.60-1.92 (m, 2H), 0.98 (d, J=6.0 Hz, 3H). LC-MS: m/z=336 (M+H)$^+$.

Step 10

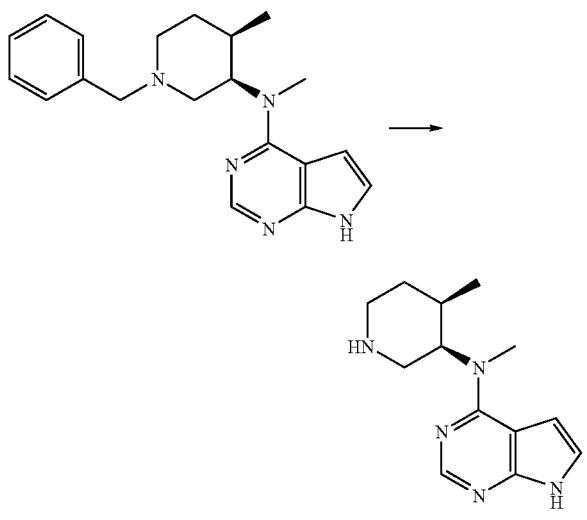

N-Methyl-N-((3R,4R)-4-methylpiperidin-3-yl)-7H-pyrrolo[2,3-d]pyrimidin-4-amine

Palladium hydroxide on carbon (50 mg), and acetic acid (44 mg, 0.72 mmol, 1.00 equiv.) were added to a solution of N-((3R,4R)-1-benzyl-4-methylpiperidin-3-yl)-N-methyl-7H-pyrrolo[2,3-d]pyrimidin-4-amine (250 mg, 0.67 mmol, 1.00 equiv.) in isopropanol/water (10 mL/2 mL). After hydrogen gas was introduced, the resulting mixture was stirred at about 50° C. for about 16 hours. After filtering the mixture, the pH value of the filtrate was adjusted to 8 by adding sodium hydroxide. Standard extractive workup with dichloromethane (3×20 mL) afforded the title product as an off-white solid (140 mg; yield=81%) $^1$H NMR (300 MHz, CDCl$_3$) δ: 10.60 (br s, 1H), 8.35 (s, 1H), 7.07 (d, J=3.6 Hz, 1H), 6.60 (d, J=3.6 Hz, 1H), 4.88-4.98 (m, 1H), 3.45 (s, 3H), 3.25-3.37 (m, 1H), 2.80-3.10 (m, 3H), 2.45-2.58 (m, 1H), 1.82-2.00 (m, 1H), 1.60-1.80 (m, 2H), 1.11 (d, J=7.2 Hz, 3H). LC-MS: m/z=246 (M+H)$^+$.

Step 11

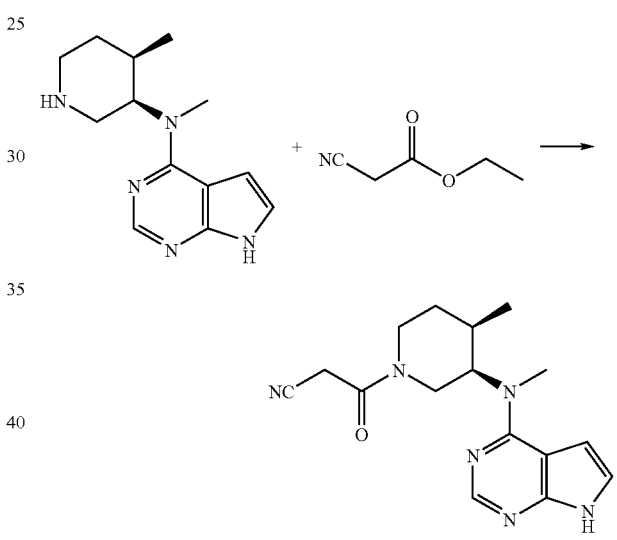

3-((3R,4R)-4-Methyl-3-(methyl(7H-pyrrolo[2,3-d]pyrimidin-4-yl)amino)piperidin-1-yl)-3-oxopropanenitrile (CP-690550)

Ethyl 2-cyanoacetate (140 mg, 1.23 mmol, 6.00 equiv.) and triethylamine (40 mg, 0.39 mmol, 2.00 equiv.) were added to a solution of N-methyl-N-((3R,4R)-4-methylpiperidin-3-yl)-7H-pyrrolo[2,3-d]pyrimidin-4-amine 12 (50 mg, 0.19 mmol, 1.00 equiv.) in toluene (10 mL). The resulting solution was stirred at about 110° C. for about 16 hours and then was concentrated in vacuo. The resulting residue was purified by silica gel column chromatography (ethyl acetate/methanol (50:1)) to give the title product as a light yellow solid (33 mg; yield=52%). $^1$H NMR (300 MHz, CD$_3$OD) δ: 8.10 (s, 1H), 7.10 (d, J=4.0 Hz, 1H), 6.65 (d, J=4.0 Hz, 1H), 5.00-5.10 (m, 1H), 3.80-4.00 (m, 2H), 3.55-3.75 (m, 1H), 3.40-3.55 (m, 1H), 3.30-3.40 (m, 5H), 2.40-2.55 (m, 1H), 1.82-2.00 (m, 1H), 1.60-1.80 (m, 1H), 1.05-1.20 (m, 3H). LC-MS: m/z=313 (M+H)$^+$.

Step 12

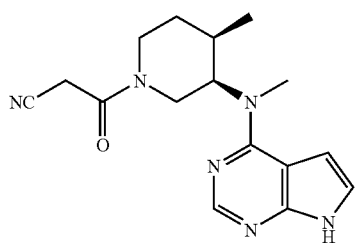

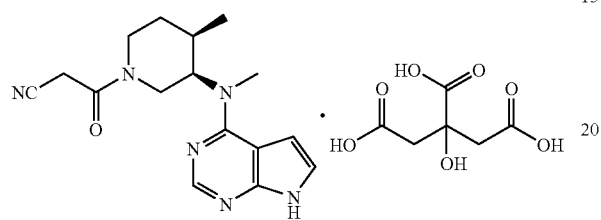

3-((3R,4R)-4-Methyl-3-(methyl(7H-pyrrolo[2,3-d]pyrimidin-4-yl)amino)piperidin-1-yl)-3-oxopropanenitrile mono citrate salt (CP-690550 citrate salt)

Citric acid (20 mg, 0.10 mmol, 1.00 equiv.) was added to a solution of 3-((3R,4R)-4-methyl-3-(methyl(7H-pyrrolo[2,3-d]pyrimidin-4-yl)amino)piperidin-1-yl)-3-oxopropanenitrile (33 mg, 0.10 mmol, 1.00 equiv.) in water/methanol (5/0.5 mL). The resulting solution was stirred at about 40° C. for about 10 minutes, and then was cooled to ambient temperature. The solvent was then removed by using a cryofreeze-dryer to give the title compound as an off-white solid (40 mg; yield=76%). $^1$H NMR (300 MHz, CD$_3$OD) δ: 8.15 (s, 1H), 7.15 (d, J=3.6 Hz, 1H), 6.70 (d, J=3.6 Hz, 1H), 4.95-5.15 (m, 1H), 3.85-4.08 (m, 4H), 3.58-3.80 (m, 1H), 3.40-3.60 (m, 4H), 2.92 (Ab$_q$, J=15.6 Hz, 2H), 2.80 (Ab$_q$, J=15.6 Hz, 2H), 2.40-2.60 (m, 1H), 1.85-2.05 (m, 1H), 1.68-1.85 (m, 1H), 1.05-1.20 (m, 3H). LC-MS: m/z=313 (MH—C$_6$H$_8$O$_7$)$^+$.

EXAMPLE 2

3-((3R,4R)-4-Methyl-3-(d$_3$-methyl(2-d$_1$-7H-pyrrolo[2,3-d]pyrimidin-4-yl)amino)piperidin-1-yl)-3-oxopropanenitrile Mono Citrate Salt (CP-690550-d$_4$ Citrate Salt)

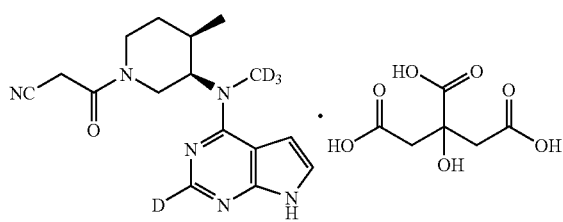

Step 1

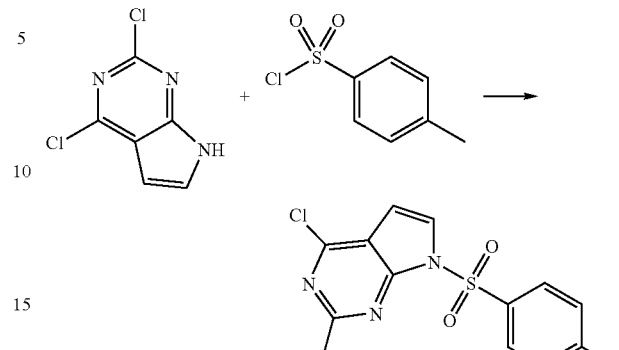

4-Chloro-7-tosyl-7H-pyrrolo[2,3-d]pyrimidine

4-Methylbenzene-1-sulfonyl chloride (3.7 g, 19.32 mmol, 1.20 equiv.) was added to a solution of 2,4-dichloro-7H-pyrrolo[2,3-d]pyrimidine 1 (3 g, 16.1 mmol, 1.00 equiv.) in acetone (20 mL). At about 0° C., an aqueous sodium hydroxide solution (2 mol/L, 12 mL) was added dropwise to the solution. The solution was then stirred at ambient temperature for about 3 hours. The solids were collected by filtration and washed with acetone/water to give the title product as a white solid (5.2 g; yield=95%). LC-MS: m/z=342 (M+H)$^+$.

Step 2

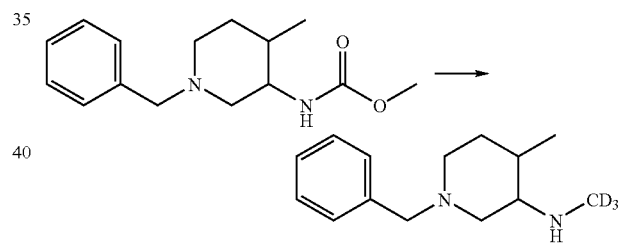

(1-Benzyl-4-methyl-piperidin-3-yl)-d$_3$-methyl-amine

The procedure of Example 1, Step 6 was followed but substituting lithium aluminum deuteride for lithium aluminum hydride. The title product was isolated as a yellow oil (3.0 g; yield=72%). LC-MS: m/z=222 (M+H)$^+$.

Step 3

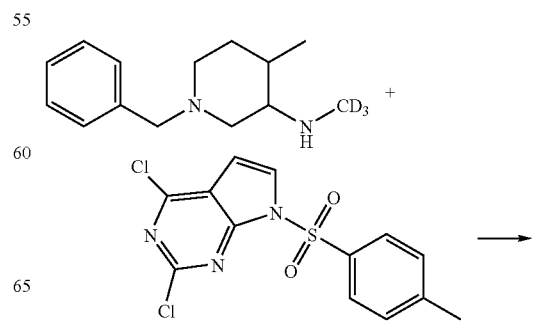

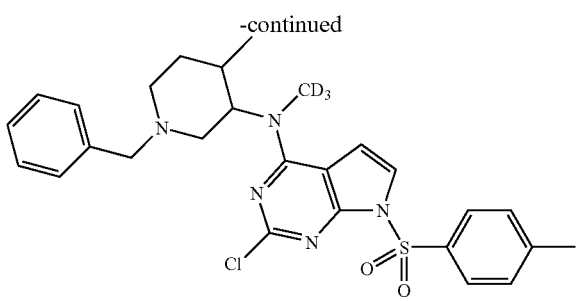

N-(1-Benzyl-4-methylpiperidin-3-yl)-2-chloro-N-d₃-methyl-7-tosyl-7H-pyrrolo[2,3-d]pyrimidin-4-amine A mixture of (1-benzyl-4-methyl-piperidin-3-yl)-d₃-methyl-amine (700 mg, 2.89 mmol, 1.00 equiv.), 2,4-dichloro-7H-pyrrolo[2,3-d]-pyrimidine (2 g, 5.78 mmol, 2.00 equiv.) and potassium carbonate (2.7 g, 19.4 mmol, 6.00 equiv) in tetrahydrofuran/water (1:1) (60 mL) was heated at about 60° C. for about 16 hours, and then the solvent was removed in vacuo. Following standard extractive workup with ethyl acetate (3×200 mL), the crude residue was purified by column chromatography to give the title product as a light yellow solid (1.5 g; yield=96%). LC-MS: m/z=527 (M+H)⁺.

Step 4

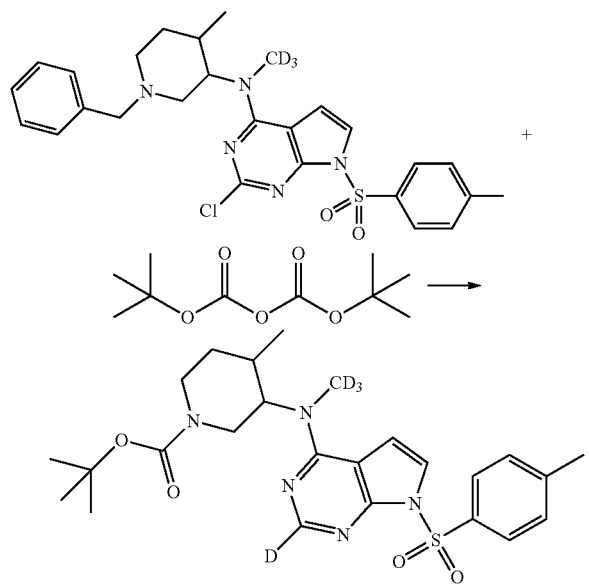

tert-Butyl 4-methyl-3-(d₃-methyl(2-d₁-7-tosyl-7H-pyrrolo[2,3-d]pyrimidin-4-yl)amino)piperidine-1-carboxylate Under an atmosphere of deuterium gas, a solution of N-(1-benzyl-4-methylpiperidin-3-yl)-2-chloro-N-d₃-methyl-7-tosyl-7H-pyrrolo[2,3-d]pyrimidin-4-amine (400 mg, 0.80 mmol, 1.00 equiv.), di-tert-butyl dicarbonate (348 mg, 1.6 mmol) and palladium hydroxide on carbon (1.00 equiv.; pretreated with deuterium oxide for three cycles) in d₄-methanol/deuterium oxide (1:3) (30 mL) was heated at about 70° C. for about 16 hours. Following standard extractive workup with ethyl acetate, the crude residue was purified by silica gel column chromatography to give the title product as a solid (300 mg; yield=78.5%). LC-MS: m/z=504 (M+H)⁺.

Step 5

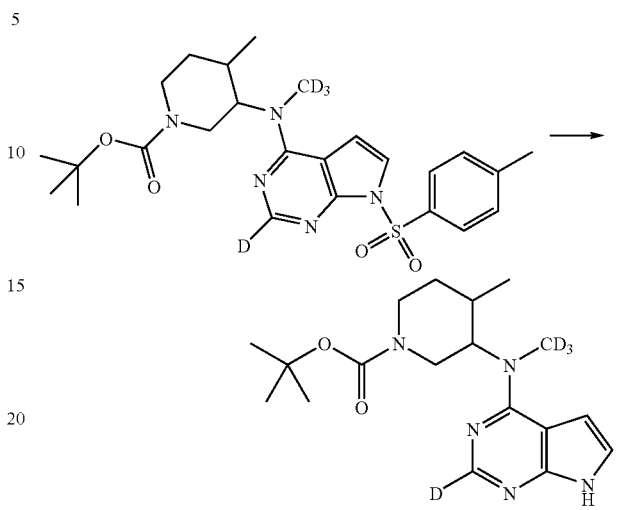

4-Methyl-3-[d₃-methyl-(2-d₁-7H-pyrrolo[2,3-d]pyrimidin-4-yl)-amino]-piperidine-1-carboxylic acid tert-butyl ester A solution of tert-butyl 4-methyl-3-(d₃-methyl(2-d₁-7-tosyl-7H-pyrrolo[2,3-d]pyrimidin-4-yl)amino)piperidine-1-carboxylate (300 mg) in 30% d₁-sodium hydroxide (60 mL) was heated at about 100° C. for about 2 hours. Following standard extractive workup with ethyl acetate (3×200 mL), the crude residue was purified by silica gel column chromatography to afford the title product as a foamy solid (190 mg; yield=90%). LC-MS: m/z=350 (M+H)⁺.

Step 6

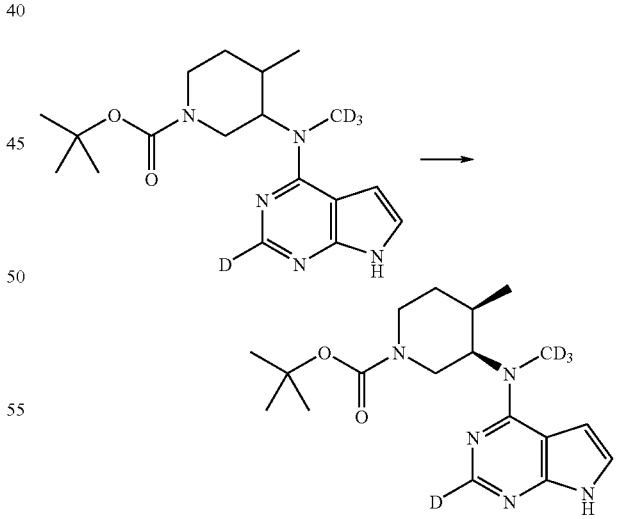

3-((3R,4R)-4-Methyl-3-[d₃-methyl-(2-d₁-7H-pyrrolo[2,3-d]pyrimidin-4-yl)-amino]-piperidine)-1-carboxylic acid tert-butyl ester The enantiomer 3-((3R,4R)-4-methyl-3-[d₃-methyl-(2-d₁-7H-pyrrolo[2,3-d]pyrimidin-4-yl)-amino]-piperidine)-1- carboxylic acid tert-butyl ester was isolated from 4-methyl-3-[d₃-methyl-(2-d₁-7H-pyrrolo[2,3-d]pyrimidin-4-yl)-amino]-piperidine-1-carboxylic acid tert-butyl ester (4.5 g) by chiral resolution using chiral-Prep-HPLC with the following conditions: column, Chiralpak IA, 0.46×15 cm; mobile phase: (hexane: isopropyl alcohol (90:10)); detector: UV 254 nm. Retention time of desired enantiomer: 7.19 minutes, undesired enantiomer retention time: 9.11 minutes. ee %>99.8%. The title product was isolated as a yellow solid (1.5 g; yield=35%). LC-MS: m/z=527 (M+H)⁺.

Step 7

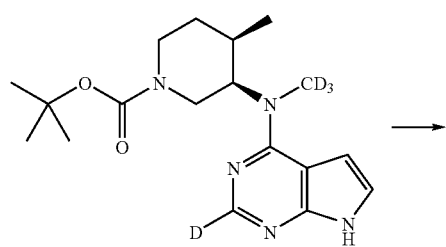

N-d₃-Methyl-N-((3R,4R)-4-methylpiperidin-3-yl)-2-d₁-7H-pyrrolo[2,3-d]pyrimidin-4-amine deuterochloride A solution of 3-((3R,4R)-4-methyl-3-[d₃-methyl-(2-d₁-7H-pyrrolo[2,3-d]pyrimidin-4-yl)-amino]-piperidine)-1-carboxylic acid tent-butyl ester (190 mg) in 5N deuterium chloride/dioxane (0.5 mL/3 mL) was stirred at 25° C. for about 16 hours. The solution was concentrated in vacuo, and the resulting residue was used in the next step without any further purification. LC-MS: m/z=250 (M+H)⁺.

Step 8

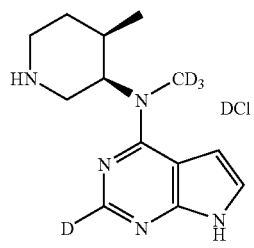

3-((3R,4R)-4-Methyl-3-(d₃-methyl(2-d₁-7H-pyrrolo[2,3-d]pyrimidin-4-yl)amino)piperidin-1-yl)-3-oxo-propanenitrile (CP-690550)

The procedure of Example 1, Step 11 was followed, but substituting N-d₃-methyl-N-((3R,4R)-4-methylpiperidin-3-yl)-2-d₁-7H-pyrrolo[2,3-d]pyrimidin-4-amine deuterochloride for N-methyl-N-((3R,4R)-4-methylpiperidin-3-yl)-7H-pyrrolo[2,3-d]pyrimidin-4-amine. The title product was isolated as a light yellow solid (33 mg; yield=52%). LC-MS: m/z=317 (M+H)⁺.

Step 9

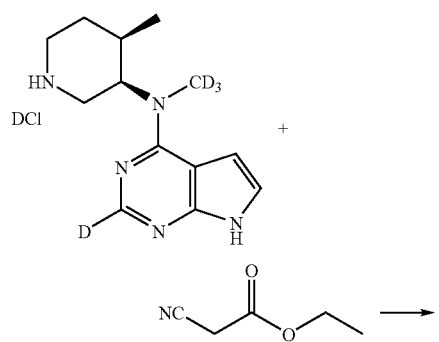

3-((3R,4R)-4-Methyl-3-(d₃-methyl(2-d₁-7H-pyrrolo[2,3-d]pyrimidin-4-yl)amino)piperidin-1-yl)-3-oxo-propanenitrile mono citrate salt (CP-690550-d₄ citrate salt)

The procedure of Example 1, Step 12 was followed, but substituting 3-((3R,4R)-4-methyl-3-(d₃-methyl(2-d₁-7H-pyrrolo[2,3-d]pyrimidin-4-yl)amino)piperidin-1-yl)-3-oxopropanenitrile for 3-((3R,4R)-4-methyl-3-(methyl(7H-pyrrolo[2,3-d]pyrimidin-4-yl)amino)piperidin-1-yl)-3-oxopropanenitrile. The title product was isolated as a white solid (40 mg; yield=76%). ¹H NMR (300 MHz, CD₃OD) δ: 7.36 (s, 1H), 6.89 (s, 1H), 4.95-5.15 (m, 1H), 3.85-4.08 (m, 4H), 3.48-3.75 (m, 2H), 2.94 (Ab_q, J=15.9 Hz, 2H), 2.81

($Ab_q$, J=15.6 Hz, 2H), 2.48-2.61 (m, 1H), 1.89-2.05 (m, 1H), 1.69-1.88 (m, 1H), 1.14 (d, J=6.6 Hz, 3H). LC-MS: m/z=317 (MH—$C_6H_8O_7$)$^+$.

EXAMPLE 3

3-((3R,4R)-4-$d_3$-methyl-3-($d_3$-methyl (2-$d_1$-7H-pyrrolo[2,3-d]pyrimidin-4-yl)amino)piperidin-1-yl)-3-oxopropanenitrile Mono Citrate Salt (CP-690550-$d_7$ Citrate Salt)

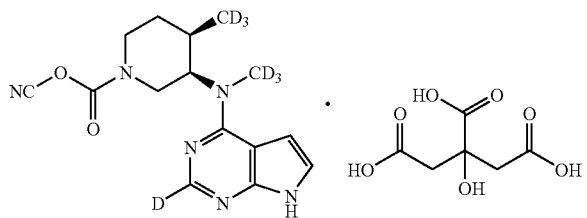

Step 1

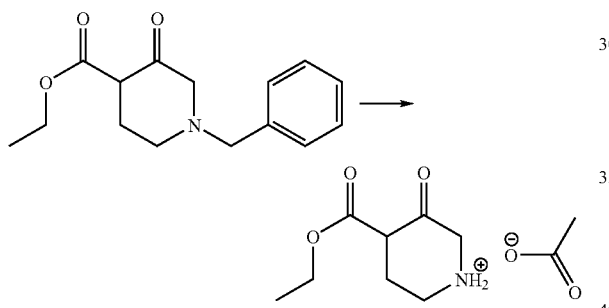

Ethyl 3-oxopiperidine-4-carboxylate acetic salt

Under an atmosphere of hydrogen, the mixture of ethyl 1-benzyl-3-oxopiperidine-4-carboxylate (20 g, 16.1 mmol, 1.00 equiv.), 10% palladium on carbon, acetic acid (10 mL), and methanol (100 mL) was heated at about 50° C. for about 4 hours. The mixture was filtered, the filtrate was evaporated to give the title product as an acetic salt (16 g; yield=85%). LC-MS: m/z=172 (M+H)$^+$.

Step 2

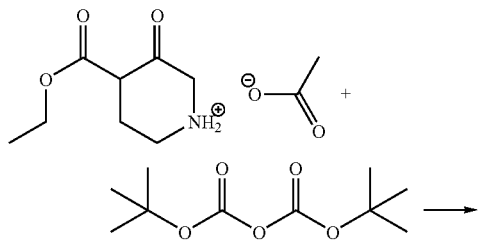

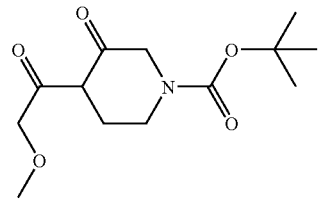

Methyl 4-methylpyridin-3-ylcarbamate

A solution of di-tert-butyl dicarbonate (5.66 g, 26 mmol), potassium carbonate (12 g, 86.4 mmol) and water (100 mL) was added to a solution of ethyl 3-oxopiperidine-4-carboxylate acetic salt (15 g, 21.6 mmol) in tetrahydrofuran (400 mL). The resulting mixture was stirred at ambient temperature for about 2 hours. After removing the solvent in vacuo, standard extractive workup with ethyl acetate (3×200 mL) afforded the title product as a pale white solid (14 g; yield=80%). LC-MS: m/z=172/272 (M+H)$^+$.

Step 3

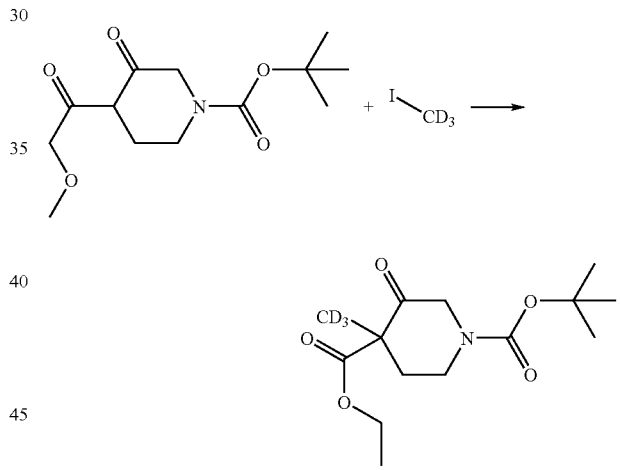

1-tert-Butyl-4-ethyl 4-$d_3$-methyl-3-oxopiperidine-1,4-dicarboxylate

70% Sodium hydride (3.54 g, 103 mmol) was added in several portions to a solution of 1-tert-butyl 4-ethyl 3-oxopiperidine-1,4-dicarboxylate (14 g, 51.6 mmol, 1.00 equiv.) in tetrahydrofuran (300 mL). The resulting mixture was heated at about 50° C. for about 2 hours, and then was cooled to ambient temperature. After adding iodomethane (15 g, 103 mmol), the resulting suspension was stirred at ambient temperature for about 3 hours and then poured into ice. Standard extractive workup with ethyl acetate (3×100 mL) gave a crude residue that was then purified by column chromatography to give the title product as a solid (7.4 g; yield=50%). LC-MS: m/z=289 (M+H)$^+$.

Step 4

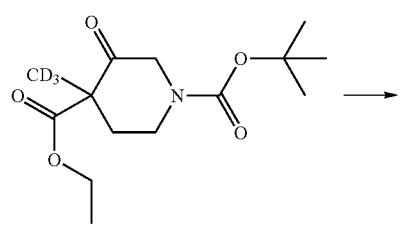

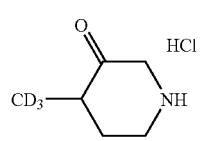

4-d₃-Methylpiperidin-3-one hydrochloride

37% Hydrogen chloride (30 mL) was added to 1-tert-butyl 4-ethyl 4-d₃-methyl-3-oxopiperidine-1,4-dicarboxylate (7 g, 25.6 mmol). The resulting mixture was heated at reflux for about 3 hours, and then the solvent was removed by evaporation in vacuo. The resulting residue was used in the next step without further purification. LC-MS: m/z=117/125 (M+H)⁺.

Step 5

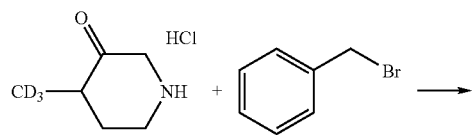

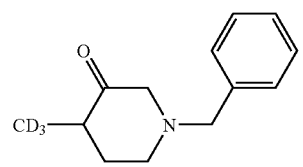

1-Benzyl-4-d₃-methylpiperidin-3-one (Bromomethyl)benzene (2.23 g, 10.5 mmol) was added dropwise to a solution of 4-d₃-methylpiperidin-3-one hydrochloride (1.2 g, 10.3 mmol, 1.00 equiv.) and triethylamine (2.1 g, 20.6 mmol) in tetrahydrofuran (30 mL). The resulting mixture was stirred at ambient temperature for about 16 hours, and then solvent was evaporated in vacuo. Following standard extractive workup with ethyl acetate, the crude residue was purified by column chromatography to give the title product as a solid (1.7 g; yield=80%). ¹H NMR (300 MHz, CD₃OD) δ: 7.21-7.39 (m, 5H), 3.5 (s, 2H), 3.23 (d, J=13.8 Hz, 1H), 2.94 (d, J=9.6 Hz, 1H), 2.79 (d, J=13.8 Hz, 1H), 2.45 (t, J=11.4 Hz, 1H), 2.29-2.39 (m, 1H), 1.98-2.01 (m, 1H), 1.59-1.71 (m, 341H). LC-MS: m/z=207/225 (M+H)⁺.

Step 6

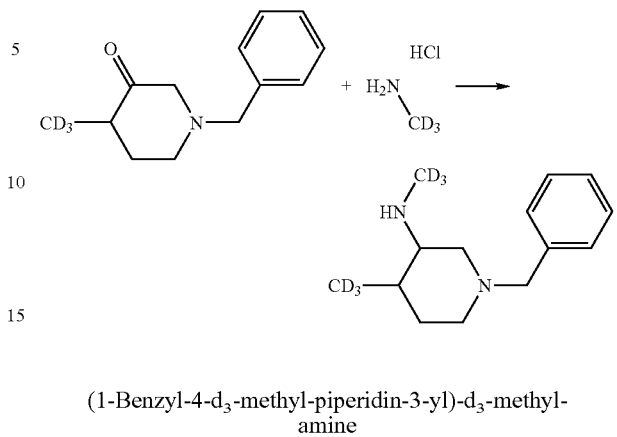

(1-Benzyl-4-d₃-methyl-piperidin-3-yl)-d₃-methyl-amine

At about 0° C., sodium methoxide (3.2 g, 38.2 mmol) was added to a suspension of d₃-methylamine hydrochloride (1.4 g, 19.4 mmol), 1-benzyl-4-d₃-methylpiperidin-3-one (2 g 9.7 mmol) and tetrahydrofuran (60 mL). The mixture was stirred at ambient temperature for about 16 hours, and then sodium triacetoxy borohydride (8.5 g, 40 mmol) was added. The mixture was stirred at ambient temperature for about 5 hours, and then 5% sodium hydroxide (50 mL) was added. Following standard extractive workup with ethyl acetate, the crude residue was purified by silica gel column chromatography (dichloromethane/methanol) to afford the title product (2.2 g; yield=50%). LC-MS: m/z=225 (M+H)⁺.

Step 7

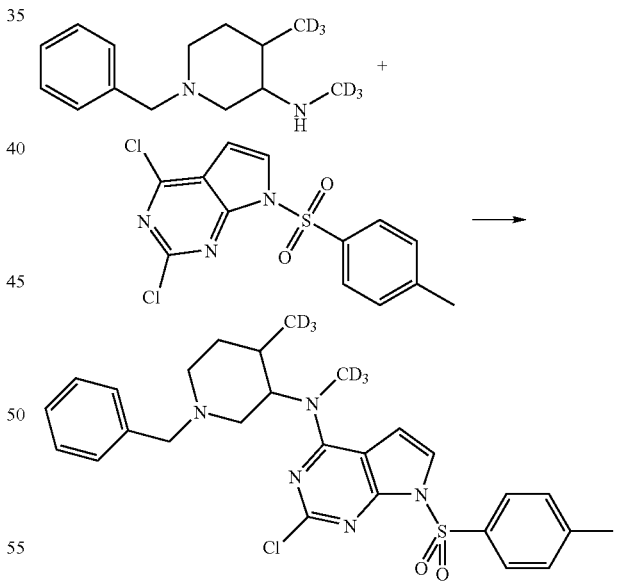

N-(1-Benzyl-4-d₃-methylpiperidin-3-yl)-2-chloro-N-d₃-methyl-7-tosyl-7H-pyrrolo[2,3-d]pyrimidin-4-amine The procedure of Example 2, Step 3 was followed but substituting (1-benzyl-4-d₃-methyl-piperidin-3-yl)-d₃-methyl-amine for (1-benzyl-4-methyl-piperidin-3-yl)-d₃-methyl-amine. The title product was isolated a light yellow solid (1.4 g; yield=90%). LC-MS: m/z=530 (M+H)⁺.

Step 8

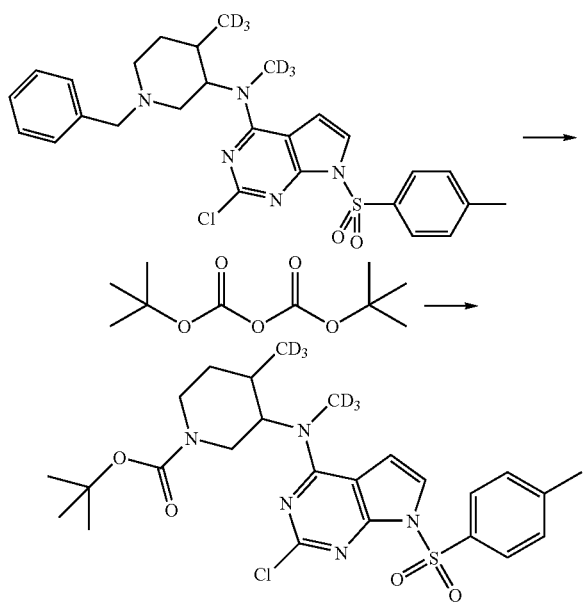

tert-Butyl 4-d₃-methyl-3-(d₃-methyl(2-d₁-7-tosyl-
7H-pyrrolo[2,3-d]pyrimidin-4-yl)amino)piperidine-
1-carboxylate The procedure of Example 2, Step 4 was followed but substituting N-(1-benzyl-4-d₃-methylpiperidin-3-yl)-2-chloro-N-d₃-methyl-7-tosyl-7H-pyrrolo[2,3-d]pyrimidin-4-amine for N-(1-benzyl-4-methylpiperidin-3-yl)-2-chloro-N-d₃-methyl-7-tosyl-7H-pyrrolo[2,3-d]pyrimidin-4-amine. The title product was isolated as a solid (270 mg, yield=70%). LC-MS: m/z=507 (M+H)⁺.

Step 9

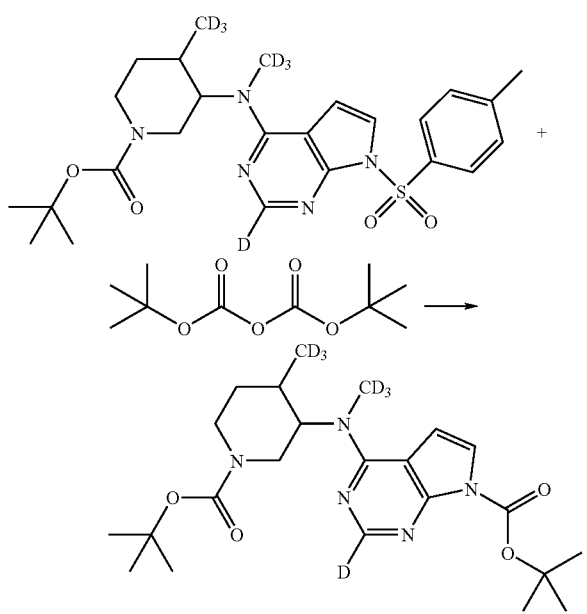

tert-Butyl 4-((1-(tert-butoxycarbonyl)-4-d₃-methylpi-
peridin-3-yl)-d₃-methyl)amino)-2-d₁-7H-pyrrolo[2,
3-d]pyrimidine-7-carboxylate A mixture of tert-butyl 4-d₃-methyl-3-(d₃-methyl(2-d₁-7-tosyl-7H-pyrrolo[2,3-d]pyrimidin-4-yl)amino)piperidine-1-carboxylate (200 mg, 0.4 mmol) and 30% d₁-sodium hydroxide (60 mL) was heated at about 100° C. for about 16 hours. After cooling the mixture to ambient temperature, di-tert-butyl dicarbonate (170 mg, 0.8 mmol) and tetrahydrofuran (20 ml) were added. The mixture was stirred at ambient temperature for about 16 hours, and then the solvent was removed in vacuo. Following standard extractive workup with ethyl acetate, the resulting crude residue was purified by silica gel column chromatography (ethyl acetate/petroleum (1:5)) to give the title product as a white solid. LC-MS: m/z=453 (M+H)⁺.

Step 10

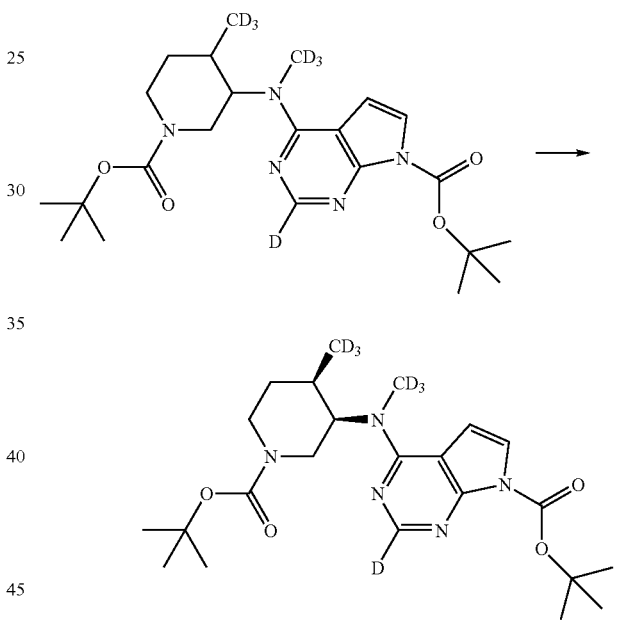

(3R,4R)-tert-Butyl 4-((1-(tert-butoxycarbonyl)-4-d₃-
methylpiperidin-3-yl)(d₃-methyl)amino)-2-d₁-7H-
pyrrolo[2,3-d]pyrimidine-7-carboxylate The enantiomer (3R,4R)-tert-butyl 4-((1-(tert-butoxycarbonyl)-4-d₃-methylpiperidin-3-yl)(d₃-methyl)amino)-2-d₁-7H-pyrrolo[2,3-d]pyrimidine-7-carboxylate was isolated from tert-butyl 4-((1-(tert-butoxycarbonyl)-4-d₃-methylpiperidin-3-yl)(d₃-methyl)amino)-2-d₁-7H-pyrrolo[2,3-d]pyrimidine-7-carboxy-late (300 mg) by chiral resolution using chiral-Prep-HPLC with the following conditions: column: Chiralpak IA (Waters 2767-1), 0.46×25 cm; mobile phase: hexane/isopropyl alcohol (90:10); detector: UV 254 nm. Retention time of desired enantiomer: 6.08 minutes, undesired enantiomer retention time: 10.16 minutes. ee %>99.8%. The title product was isolated as a white solid (0.1 g; yield=35%). LC-MS: m/z=353 (M+H)⁺.

Step 11

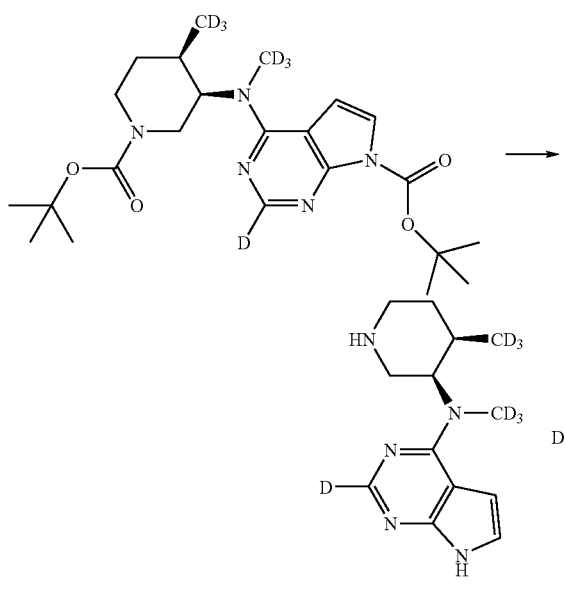

N-d₃-Methyl-N-((3R,4R)-4-d₃-methylpiperidin-3-yl)-2-d₁-7H-pyrrolo[2,3-d]pyrimidin-4-amine deuterochloride The procedure of Example 2, Step 7 was followed, but substituting (3R,4R)-tert-butyl 4-(1-(tert-butoxycarbonyl)-4-d₃-methylpiperidin-3-yl)(d₃-methyl)amino)-2-d₁-7H-pyrrolo[2,3-d]pyrimidine-7-carboxylate for 3-((3R,4R)-4-methyl-3-[d₃-methyl-(2-d₁-7H-pyrrolo[2,3-d]pyrimidin-4-yl)-amino]-piperidine)-1-carboxylic acid tert-butyl ester. The title product was isolated as a crude residue and was used in the next step without any further purification. LC-MS: m/z=253 (M+H)⁺.

Step 12

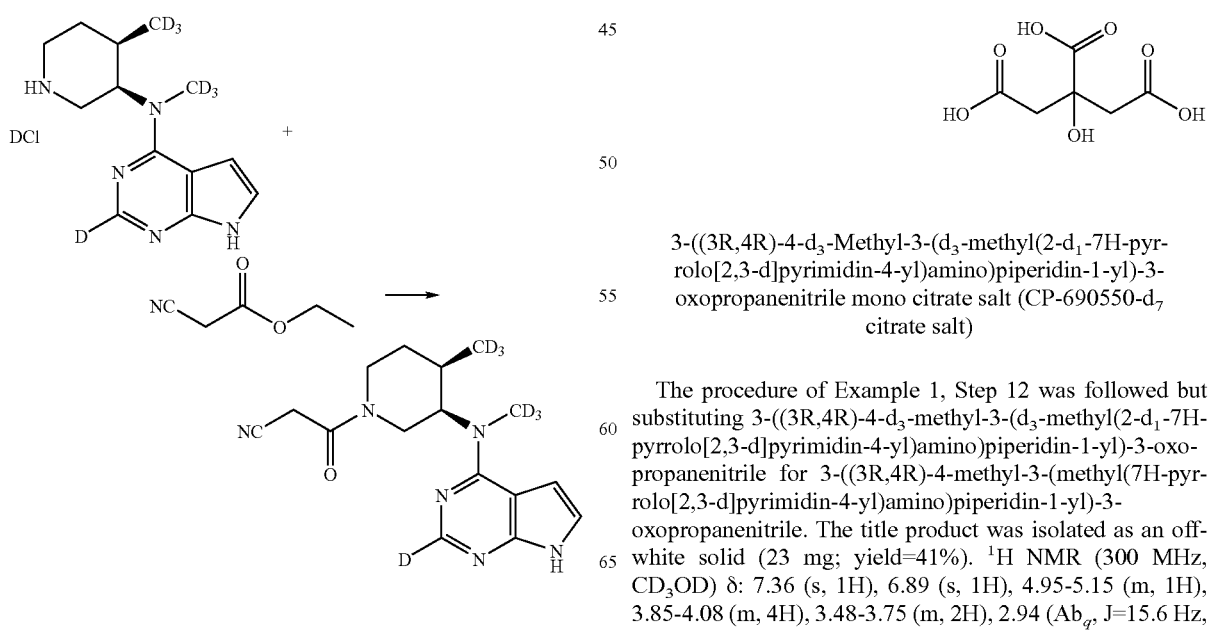

3-((3R,4R)-4-d₃-Methyl-3-(d₃-methyl(2-d₁-7H-pyrrolo[2,3-d]pyrimidin-4-yl)amino)piperidin-1-yl)-3-oxopropanenitrile (CP-690550-d₇)

The procedure of Example 1, Step 11 was followed but substituting N-d₃-methyl-N-((3R,4R)-4-d₃-methylpiperidin-3-yl)-2-d₁-7H-pyrrolo[2,3-d]pyrimidin-4-amine deuterochloride for N-methyl-N-((3R,4R)-4-methylpiperidin-3-yl)-7H-pyrrolo[2,3-d]pyrimidin-4-amine. The title product was isolated as a light yellow solid (40 mg; yield=56%). LC-MS: m/z=320 (M+H)⁺.

Step 13

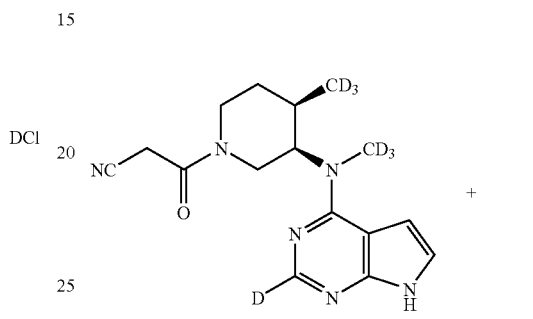

3-((3R,4R)-4-d₃-Methyl-3-(d₃-methyl(2-d₁-7H-pyrrolo[2,3-d]pyrimidin-4-yl)amino)piperidin-1-yl)-3-oxopropanenitrile mono citrate salt (CP-690550-d₇ citrate salt)

The procedure of Example 1, Step 12 was followed but substituting 3-((3R,4R)-4-d₃-methyl-3-(d₃-methyl(2-d₁-7H-pyrrolo[2,3-d]pyrimidin-4-yl)amino)piperidin-1-yl)-3-oxopropanenitrile for 3-((3R,4R)-4-methyl-3-(methyl(7H-pyrrolo[2,3-d]pyrimidin-4-yl)amino)piperidin-1-yl)-3-oxopropanenitrile. The title product was isolated as an off-white solid (23 mg; yield=41%). ¹H NMR (300 MHz, CD₃OD) δ: 7.36 (s, 1H), 6.89 (s, 1H), 4.95-5.15 (m, 1H), 3.85-4.08 (m, 4H), 3.48-3.75 (m, 2H), 2.94 (Ab_q, J=15.6 Hz, 2H), 2.81 (Ab$_q$, J=15.9 Hz, 2H), 2.48-2.61 (m, 1H), 1.89-2.05 (m, 1H), 1.69-1.88 (m, 1H). LC-MS: m/z=320 (MH—C$_6$H$_8$O$_7$)$^+$.

EXAMPLE 4

3-((3R,4R)-4-d$_3$-methyl-3-(d$_3$-methyl (2-d$_1$-7H-pyrrolo[2,3-d]pyrimidin-4-yl)amino)-2,2',3,4-d$_4$-piperidin-1-yl)-3-oxo-propanenitrile Mono Citrate Salt (CP-690550-d$_{11}$ Citrate Salt)

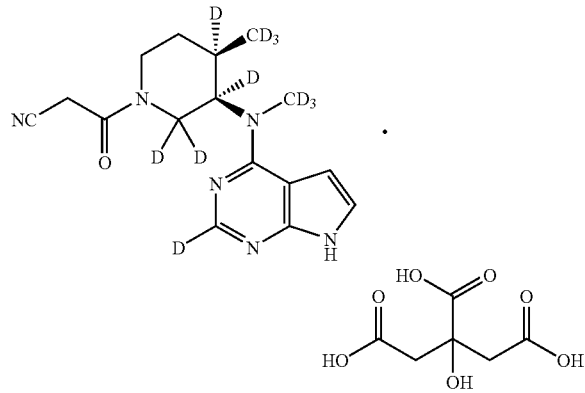

Step 1

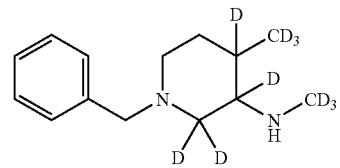

1-Benzyl-4-d$_3$-methyl-(2,2',4-d$_3$)-piperidin-3-one

A mixture of 1-benzyl-4-d$_3$-methylpiperidin-3-one 6 (2.5 g, 12.1 mmol) in 2N deuterium chloride in deuterium oxide (60 mL) was heated at about 80° C. for about 16 hours. After cooling the mixture to ambient temperature, 2N d$_1$-sodium hydroxide in deuterium oxide (80 mL) was added. Standard extractive workup with ethyl acetate, gave a crude residue which was used in the next step without further purification. LC-MS: m/z=210/228 (M+H)$^+$.

Step 2

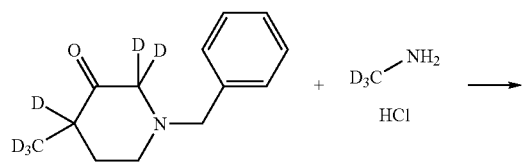

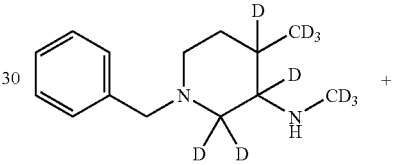

(1-Benzyl-4-d$_3$-methyl-2,2',3,4-d$_4$-piperidin-3-yl)-d$_3$-methyl-amine

The procedure of Example 3, Step 6 was followed but substituting 1-benzyl-4-d$_3$-methyl-(2,2',4-d$_3$)-piperidin-3-one for 1-benzyl-4-d$_3$-methyl-piperidin-3-one. The title product was isolated as a solid (3.9 g; yield=90%). LC-MS: m/z=229 (M+H)$^+$.

Step 3

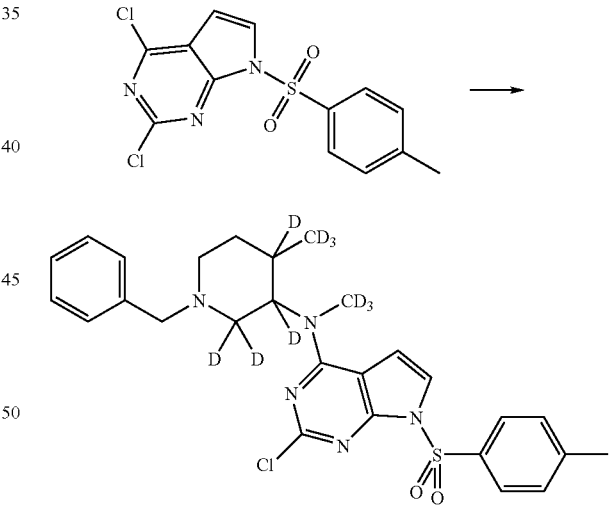

N-(1-Benzyl-4-d$_3$-methyl-2,2',3,4-d$_4$-piperidin-3-yl)-2-chloro-N-d$_3$-methyl-7-tosyl-7H-pyrrolo[2,3-d]pyrimidin-4-amine The procedure of Example 2, Step 3 was followed, but substituting (1-benzyl-4-d$_3$-methyl-2,2',3,4-d$_4$-piperidin-3-yl)-d$_3$-methyl-amine for (1-Benzyl-4-methyl-piperidin-3-yl)-d$_3$-methyl-amine. The title product was isolated as a light yellow solid (1.4 g; yield=90%). LC-MS: m/z=534 (M+H)$^+$.

Step 4

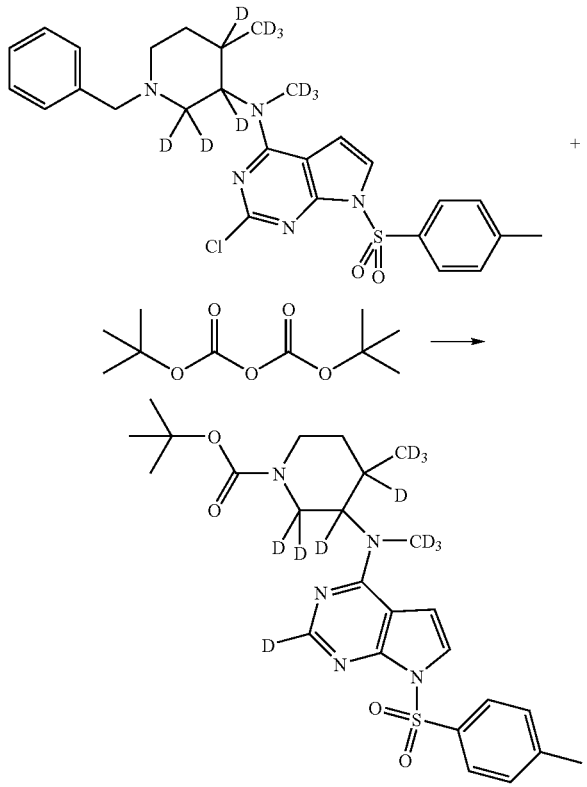

tert-Butyl 4-d₃-methyl-3-(d₃-methyl(2-d₁-7-tosyl-7H-pyrrolo[2,3-d]pyrimidin-4-yl)amino)-2,2',3,4-d₄-piperidine-1-carboxylate The procedure of Example 2, Step 4 was followed, but substituting N-(1-benzyl-4-d₃-methyl-2,2',3,4-d₄-piperidin-3-yl)-2-chloro-N-d₃-methyl-7-tosyl-7H-pyrrolo[2,3-d]pyrimidin-4-amine for N-(1-benzyl-4-methylpiperidin-3-yl)-2-chloro-N-d₃-methyl-7-tosyl-7H-pyrrolo[2,3-d]pyrimidin-4-amine. The title product was isolated as a solid (270 mg; yield=70%). LC-MS: m/z=411/511 (M+H)⁺.

Step 5

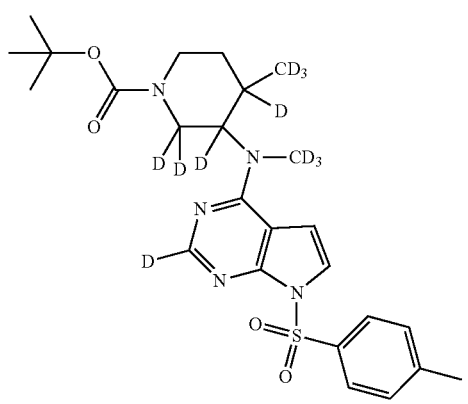

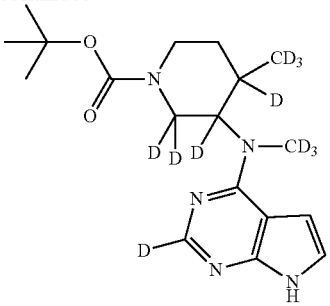

tert-Butyl 4-d₃-methyl-3-(d₃-methyl(2-d₁-7-tosyl-7H-pyrrolo[2,3-d]pyrimidin-4-yl)amino)-2,2',3,4-d₄-piperidine-1-carboxy-late The procedure of Example 2, Step 5 was followed, but substituting tert-butyl 4-d₃-methyl-3-(d₃-methyl(2-d₁-7-tosyl-7H-pyrrolo[2,3-d]pyrimidin-4-yl)amino)-2,2',3,4-d₄-piperidine-1-carboxylate for tert-butyl 4-methyl-3-(d₃-methyl(2-d₁-7-tosyl-7H-pyrrolo[2,3-d]pyrimidin-4-yl)amino)piperidine-1-carboxylate. The title product was isolated as a foamy solid (130 mg; yield=90%). ¹H NMR (300 MHz, CD₃OD) δ: 10.41-10.73 (brs, 1H), 7.07 (d, J=3.6 Hz, 1H), 6.57 (d, J=2.4 Hz, 1H), 3.38-3.71 (brs, 2H), 1.76-1.91 (m, 1H), 1.58-1.65 (m, 1H), 1.47 (s, 9H). LC-MS: m/z=257/357 (M+H)⁺.

Step 6

(3R,4R)-tert-Butyl-4-d₃-methyl-3-(d₃-methyl (2-d₁-7H-pyrrolo[2,3-d]pyrimidin-4-yl)amino)-2,2,3,4-d₄-piperidine-1-carboxylate The enantiomer (3R,4R)-tert-butyl-4-d₃-methyl-3-(d₃-methyl (2-d₁-7H-pyrrolo[2,3-d]pyrimidin-4-yl)amino)-2,2,3,4-d₄-piperidine-1-carboxylate was isolated from tert-butyl 4-d₃-methyl-3-(d₃-methyl(2-d₁-7-tosyl-7H-pyrrolo[2,3-d]

pyrimidin-4-yl)amino)-2,2',3,4-d₄-piperidine-1-carboxylate by chiral resolution using chiral-prep-HPLC with the following conditions: column: Chiralpak IC 2×25 cm (Waters 2767-1), 5 um Chiral-P(IC)001IC00CJ-LD016; mobile phase: hexane/isopropyl alcohol (85:15); detector: UV 254 nm. Retention time of desired enantiomer: 12.01 minutes, undesired enantiomer retention time: 15.10 minutes. ee %>99.8%. The title product was isolated as a yellow solid (0.1 g; yield=35%). LC-MS: m/z=490 (M+H)⁺.

Step 7

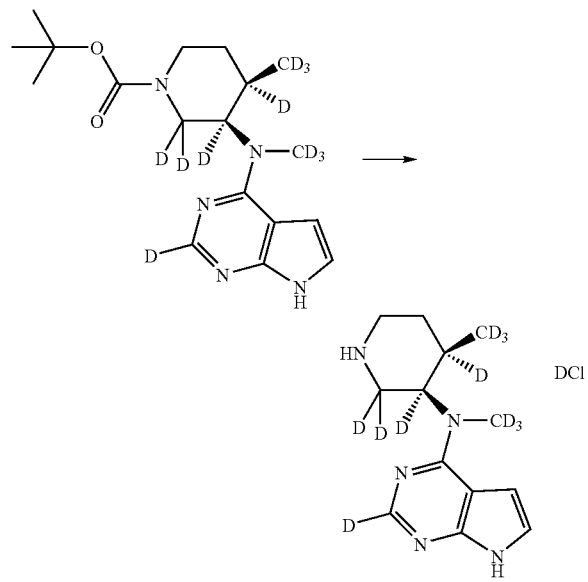

N-d₃-Methyl-N-((3R,4R)-4-d₃-methyl-2,2',3,4-d₄-piperidin-3-yl)-2-d₁-7H-pyrrolo[2,3-d]pyrimidin-4-amine deuterochloride The procedure of Example 2, Step 7 was followed, but substituting (3R,4R)-tert-butyl-4-d₃-methyl-3-(d₃-methyl (2-d₁-7H-pyrrolo[2,3-d]pyrimidin-4-yl)amino)-2,2,3,4-d₄-piperidine-1-carboxylate for 3-((3R,4R)-4-methyl-3-[d₃-methyl-(2-d₁-7H-pyrrolo[2,3-d]pyrimidin-4-yl)-amino]-piperidine)-1-carboxylic acid tert-butyl ester. The title product was isolated and used in the next step without further purification. LC-MS: m/z=257 (M+H)⁺.

Step 8

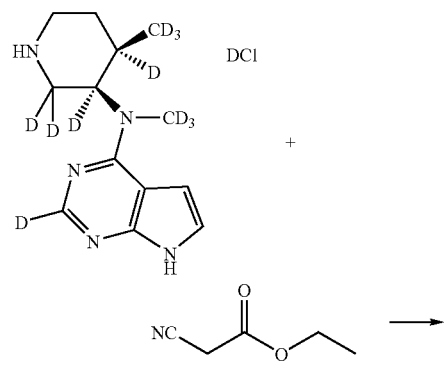

3-((3R,4R)-4-d₃-Methyl-3-(d₃-methyl(2-d₁-7H-pyrrolo[2,3-d]pyrimidin-4-yl)amino)-2,2,3,4-d₄-piperidin-1-yl)-3-oxopropane-nitrile (CP-690550-d₁₁)

The procedure of Example 1, Step 11 was followed, but substituting N-d₃-methyl-N-((3R,4R)-4-d₃-methyl-2,2',3,4-d₄-piperidin-3-yl)-2-d₁-7H-pyrrolo[2,3-d]pyrimidin-4-amine deuterochloride for N-methyl-N-((3R,4R)-4-methylpiperidin-3-yl)-7H-pyrrolo[2,3-d]pyrimidin-4-amine. The title product was isolated as a light yellow solid (50 mg; yield=63%). LC-MS: m/z=324 (M+H)⁺.

Step 9

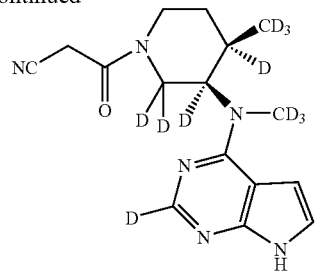

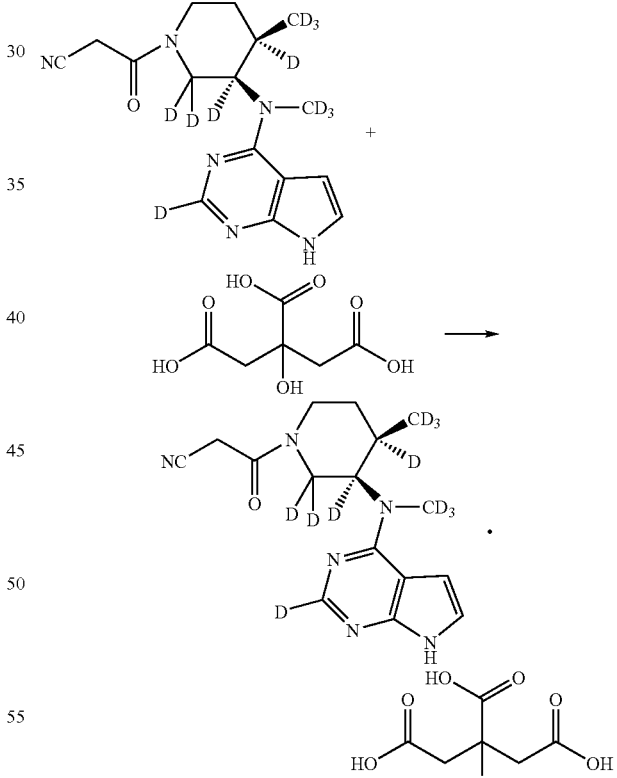

3-((3R,4R)-4-d₃-Methyl-3-(d₃-methyl (2-d₁-7H-pyrrolo[2,3-d]pyrimidin-4-yl)amino))-2,2,3,4-d₄-piperidin-1-yl)-3-oxopropane-nitrile mono citrate salt ((CP-690550-d₁₁ citrate salt)

The procedure of Example 1, Step 12 was followed, but substituting 3-((3R,4R)-4-d₃-methyl-3-(d₃-methyl(2-d₁-7H- pyrrolo[2,3-d]pyrimidin-4-yl)amino)-2,2,3,4-$d_4$-piperidin-1-yl)-3-oxopropane-nitrile for 3-((3R,4R)-4-methyl-3-(methyl(7H-pyrrolo[2,3-d]pyrimidin-4-yl)amino)piperidin-1-yl)-3-oxopropanenitrile. The title product was isolated as an off-white solid (50 mg; yield=80%). $^1$H NMR (300 MHz, CD$_3$OD) δ: 7.36 (s, 1H), 6.89 (s, 1H), 3.91-4.08 (m, 2H), 3.48-3.75 (m, 2H), 2.94 (Ab$_q$, J=15.6 Hz, 2H), 2.81 (Ab$_q$, J=15.9 Hz, 2H), 1.89-2.05 (m, 1H), 1.69-1.88 (m, 1H). LC-MS: m/z=324 (MH—$C_6H_8O_7$)$^+$.

EXAMPLE 5

3-((3R,4R)-4-$d_3$-Methyl-3-($d_3$-methyl(2-$d_1$-7H-pyrrolo[2,3-d]pyrimidin-4-yl)amino)-2,2',3,4,5,5',6,6'-$d_8$-piperidin-1-yl)-3-oxopro-panenitrile Mono Citrate Salt (CP-690550-$d_{15}$ Citrate Salt)

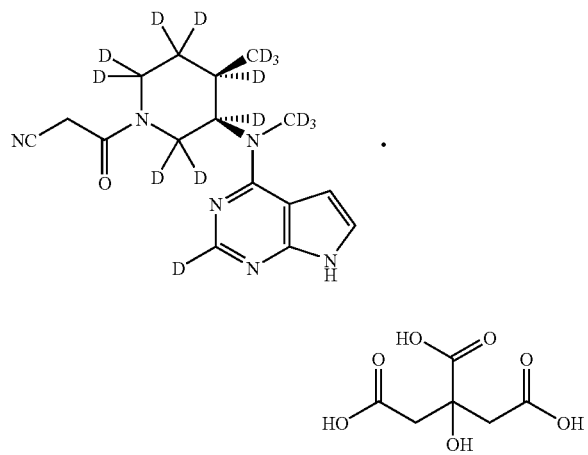

Step 1

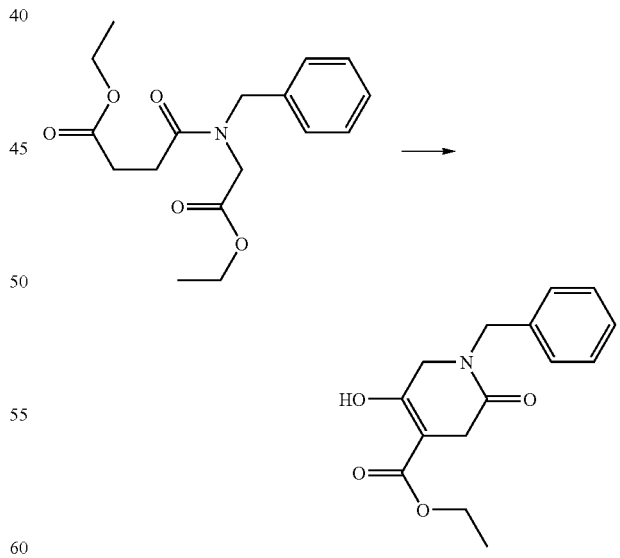

Ethyl 2-(benzylamino)acetate

A solution of diisopropylethylamine (155 g, 1.2 mol) and benzylamine (96 g, 0.9 mol) was added dropwise to a solution of ethyl bromoacetate (100 g, 0.6 mol) in dioxane (1000 mL). The resulting suspension was heated at about 90° C. for about 5 hours, and then was cooled to ambient temperature. Standard extractive workup with ethyl acetate afforded the title product as a yellow oil (90 g; yield=80%). LC-MS: m/z=194 (M+H)$^+$.

Step 2

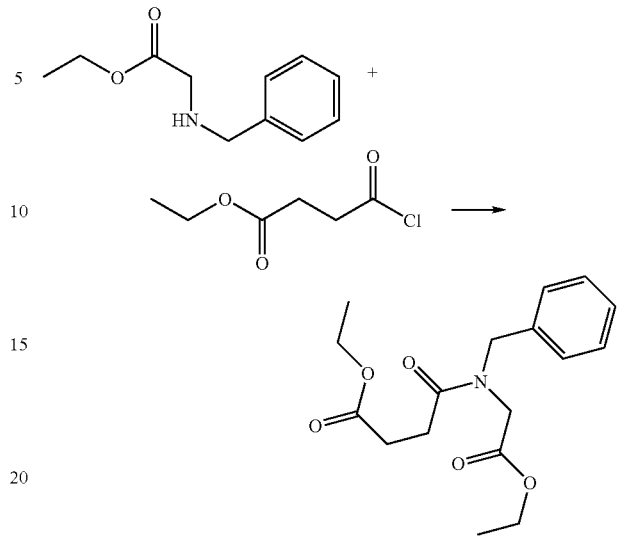

Ethyl 4-(benzyl(2-ethoxy-2-oxoethyl)amino)-4-oxobutanoate

Potassium carbonate (110.4 g, 0.97 mol) was added in one portion to a solution of ethyl 2-(benzylamino)acetate (78 g, 0.4 mol) in tetrahydrofuran (500 mL) and water (200 mL). Ethyl 4-chloro-4-oxobutanoate (72.7 g, 0.485 mol) in anhydrous tetrahydrofuran (200 mL) was then added dropwise over a period of 1 hour to the mixture. The mixture was filtered, and the filtrate was washed with ethyl acetate. After the solvent was removed by evaporation, standard extractive workup with ethyl acetate (100 mL) to afford the title product as a yellow oil (110 g; yield=80%). LC-MS: m/z=322 (M+H)$^+$.

Step 3

Ethyl 1-benzyl-5-hydroxy-2-oxo-1,2,3,6-tetrahydropyridine-4-carboxylate

Ethyl 4-(benzyl(2-ethoxy-2-oxoethyl)amino)-4-oxobutanoate (123.2 g, 0.4 mol) in ethanol (37 g, 0.8 mol) and dioxane (200 ml) was added dropwise to a suspension of sodium (18.4 g, 0.8 mol) in dioxane (500 mL). The resulting mixture was heated at reflux until the sodium metal was no longer visible. After cooling the mixture to ambient temperature, acetic acid (48 g, 0.8 mol) was added. Standard extractive workup with ethyl acetate, gave a crude product that was purified by re-crystallization from ether/acetone to afford the title product as a yellow solid (40 g; yield=40%). $^1$H NMR (300 MHz, CD$_3$OD) δ: 11.81 (s, 1H), 7.19-7.41 (m, 5H), 4.65 (s, 2H), 4.25 (q, J=7.2 Hz, 2H), 3.91 (t, J=3 Hz, 2H), 3.27 (t, J=3 Hz, 2H), 1.32 (t, J=7.2 Hz, 3H). LC-MS: m/z=276 (M+H)$^+$.

Step 4

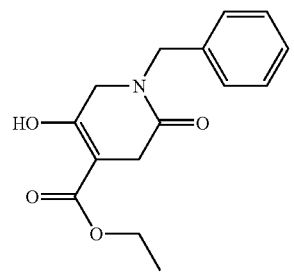

+

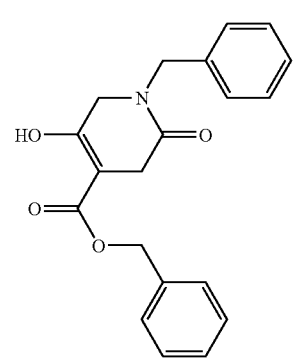

Benzyl 1-benzyl-5-hydroxy-2-oxo-1,2,3,6-tetrahydropyridine-4-carboxylate

A solution of 1-benzyl-5-hydroxy-2-oxo-1,2,3,6-tetrahydropyridine-4-carboxylate 4 (14 g, 50.9 mmol) in benzyl alcohol (27.5 g, 255 mmol) was heated at about 170° C. for about 16 hours. The solvent was removed in vacuo, and the resulting residue was re-crystallized from ether to give the title product as a yellow solid (14 g; yield=85%). LC-MS: m/z=338 (M+H)$^+$.

Step 5

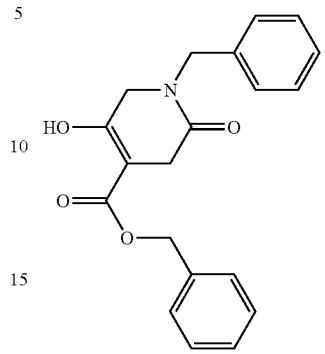

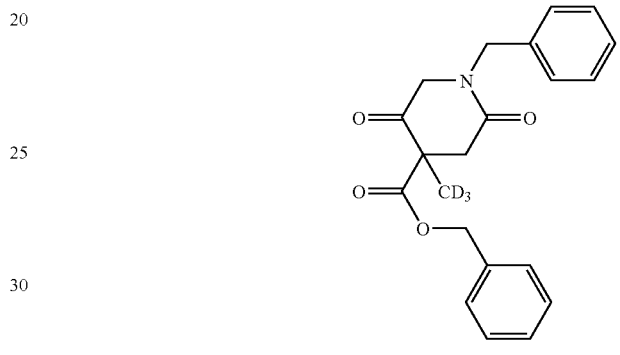

Benzyl 1-benzyl-4-trideuteromethyl-2,5-dioxopiperidine-4-carboxylate

A mixture of benzyl 1-benzyl-5-hydroxy-2-oxo-1,2,3,6-tetrahydropyridine-4-carboxylate 5 (13.5 g, 40 mmol), d$_3$-iodomethane (8.7 g, 60 mmol), potassium carbonate (16.6 g, 120 mmol) and acetone (60 mL) was heated at reflux for about 3 hours. The mixture was filtered, and the resulting filtrate was concentrated in vacuo. Standard extractive workup with ethyl acetate gave a crude residue that was then purified by re-crystallization from ether/acetone to afford the title product as a light yellow solid (11.3 g; yield=80%). LC-MS: m/z=355 (M+H)$^+$.

Step 6

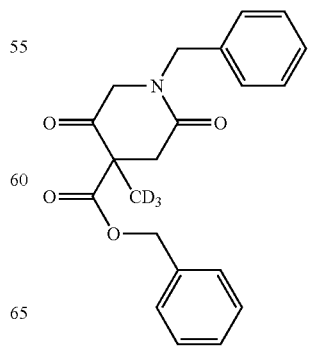

Step 8

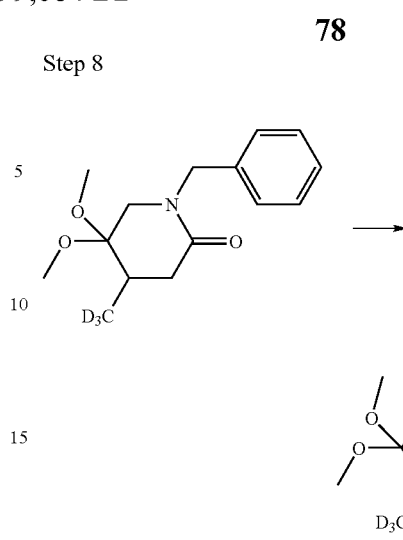

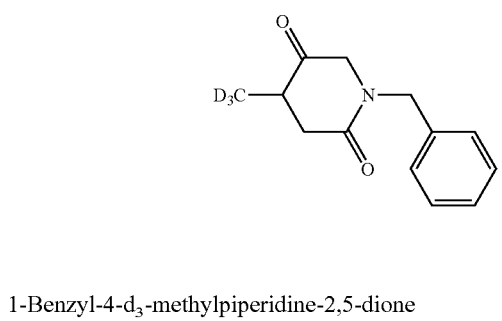

1-Benzyl-4-d₃-methylpiperidine-2,5-dione

Hydrogen gas was introduced to a suspension of 1-benzyl-4-d₃-methyl-2,5-dioxopiperidine-4-carboxylate (12.5 g, 35.3 mmol), 10% palladium on carbon (2 g), and ethyl acetate (100 mL). The mixture was heated at about 50° C. for about 16 hours. The mixture was then filtered through a Celite pad, and the filtrate was washed with ethyl acetate. The filtrate was heated at reflux for about 3 hours, and then the solvent was removed by evaporation in vacuo. The resulting residue was purified by silica gel column (petroleum ether/ethyl acetate) to give the title product (7 g; yield=90%). LC-MS: m/z=221 (M+H)⁺.

Step 7

1-Benzyl-5,5-dimethoxy-4-d₃-methyl-3,3-d₂-piperidin-2-one

A mixture of 1-benzyl-5,5-dimethoxy-4-d₃-methylpiperidin-2-one (4 g, 15 mmol), d₄-methanol (10 mL) and 30% d₁-sodium hydroxide (50 mL) was heated at about 50° C. until reaction completion, as measured by LC-MS. The mixture was cooled to ambient temperature, and deuterium oxide (25 mL) was then added. Standard extractive workup with ethyl acetate gave the title product as a yellow oil (3.3 g; yield=80%). LC-MS: m/z=269 (M+H)⁺.

Step 9

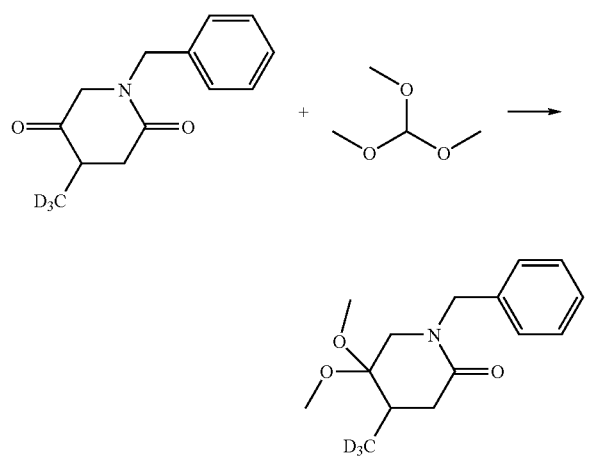

1-Benzyl-5,5-dimethoxy-4-d₃-methylpiperidin-2-one

A solution of methyl orthoformate (10 mL) and 4-methylbenzenesulfonic acid (0.5 g) in methanol (20 mL) was added dropwise to a solution of 1-benzyl-4-trideuteromethylpiperidine-2,5-dione (7 g, 31.8 mmol) in methanol (50 mL). The resulting mixture was heated at reflux for about 16 hours and then cooled to ambient temperature. After adding triethylamine (2 ml), standard extractive workup with ethyl acetate afforded a crude residue that was then purified by silica gel column chromatography to give the title product as a yellow oil (7.8 g; yield=90%). LC-MS: m/z=267 (M+H)⁺.

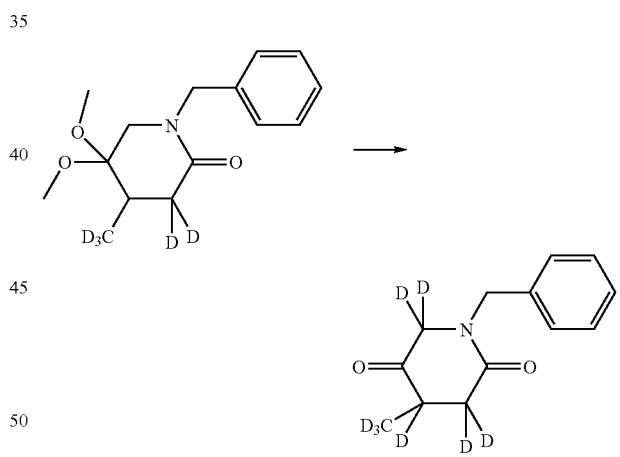

1-Benzyl-4-d₃-methyl-3,3',4,6,6',-d₅-piperidine-2,5-dione

A mixture of 1-benzyl-5,5-dimethoxy-4-d₃-methyl-3,3-d₂-piperidin-2-one (8 g, 29.8 mmol) in 1N deuterochloric acid (in deuterium oxide) (200 mL) was heated at about 80° C. for about 16 hours. The mixture was cooled to ambient temperature, and then 2N d₁-sodium hydroxide (in deuterium oxide) (110 mL) was added. The mixture was extracted with ethyl acetate, dried, and evaporated in vacuo. The resulting residue was purified by silica gel column chromatography to give the title product (4.7 g; yield=60%). LC-MS: m/z=226/244 (M+H)⁺.

Step 10

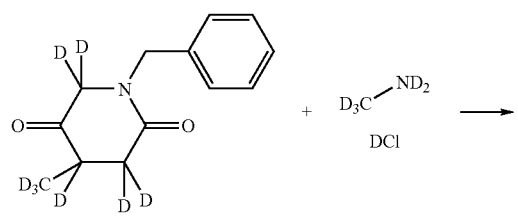

1-Benzyl-4-d$_3$-methyl-5-(d$_3$-methylamino)-3,3',4,5,
6,6'-d$_6$-piperidin-2-one At about 0° C., sodium d$_3$-methoxide (0.9 g, 16 mmol) was added to a suspension of d$_5$-methylamine deuterium chloride (1.2 g, 16 mmol) in tetrahydrofuran (10 mL). After 30 minutes, d$_4$-acetic acid (1.1 g, 16 mmol) was injected into the mixture using a syringe. The resulting mixture was then stirred at ambient temperature for about 30 minutes. After replacing the atmosphere with nitrogen, 1-benzyl-4-d$_3$-methyl-3,3',4,6,6',-d$_5$-piperidine-2,5-dione (3 g, 13.3 mmol) in tetrahydrofuran (20 mL) was then added dropwise. The mixture was stirred for about 16 hours, and then sodium triacetoxy borodeuteride (7.4 g, 32 mmol) was added. The mixture was stirred at ambient temperature for about 5 hours, and then 5% d$_1$-sodium hydroxide (50 mL) was added. Following standard extractive workup with ethyl acetate, the crude residue was purified by silica gel column chromatography to give the title product (1.2 g; yield=37%). LC-MS: m/z=245 (M+H)$^+$.

Step 11

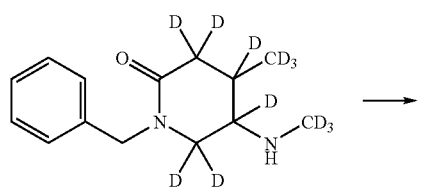

(1-Benzyl-4-d$_3$-methyl-2,2',3,4,5,5',6,6'-d$_8$-piperidin-3-yl)-d$_3$-methyl-amine 1-Benzyl-4-d$_3$-methyl-5-(d$_3$-methylamino)-3,3',4,5,6,6'-d$_6$-piperidin-2-one (1.0 g, 4.1 mmol) in tetrahydrofuran (5 mL) was added dropwise to a suspension of lithium aluminum deuteride (860 mg, 20.5 mmol) in tetrahydrofuran (20 mL). The mixture was stirred at ambient temperature for about 1 hour. After cooling the mixture to about −10° C., the mixture was poured into 10% sodium hydroxide (5 mL) containing ice. After filtering, the filtrate was concentrated in vacuo, and extracted with ethyl acetate. The organic phases were combined, washed with brine, dried, and evaporated in vacuo, to give the title product as a yellow solid (1.0 g; yield=85%). LC-MS: m/z=233 (M+H)$^+$.

Step 12

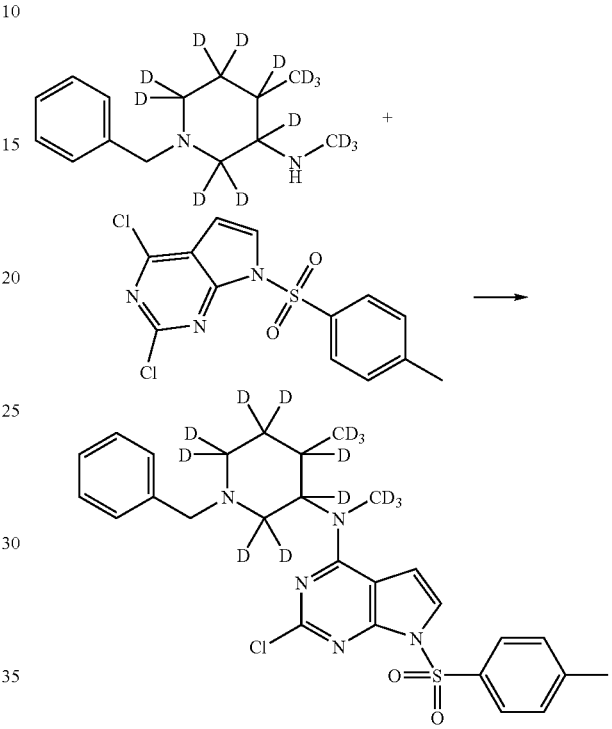

N-(1-Benzyl-4-d$_3$-methyl-2,2',3,4,5,5',6,6'-d$_8$-piperidin-3-yl)-2-chloro-N-d$_3$-methyl-7-tosyl-7H-pyrrolo[2,3-d]pyrimidin-4-amine The procedure of Example 2, Step 3 was followed, but substituting (1-benzyl-4-d$_3$-methyl-2,2',3,4,5,5',6,6'-d$_8$-piperidin-3-yl)-d$_3$-methyl-amine for (1-benzyl-4-methyl-piperidin-3-yl)-d$_3$-methyl-amine. The title product was isolated as a light yellow solid (1.4 g, yield=90%). LC-MS: m/z=538 (M+H)$^+$.

Step 13

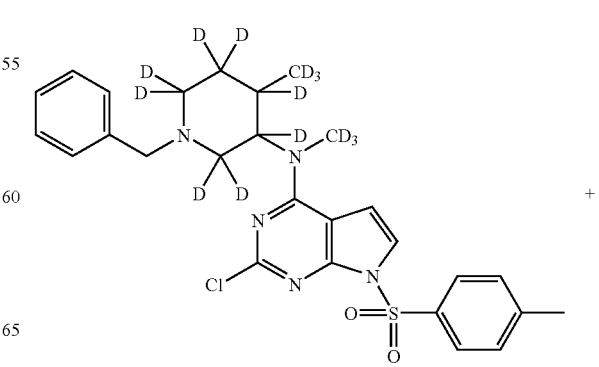

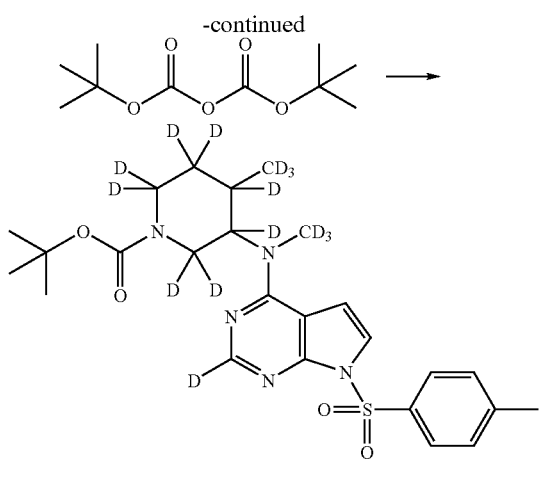

tert-Butyl 3-((2-d₁-7-tosyl-7H-pyrrolo[2,3-d]pyrimidin-4-yl)(d₃-methyl)amino)-4-d₃-methyl-2,2',3,4,5,5',6,6'-d₈-piperidine-1-carboxylate The procedure of Example 2, Step 4 was followed, but substituting N-(1-benzyl-4-d₃-methyl-2,2',3,4,5,5',6,6'-d₈-piperidin-3-yl)-2-chloro-N-d₃-methyl-7-tosyl-7H-pyrrolo[2,3-d]pyrimidin-4-amine for N-(1-benzyl-4-methylpiperidin-3-yl)-2-chloro-N-d₃-methyl-7-tosyl-7H-pyrrolo[2,3-d]pyrimidin-4-amine. The title product was isolated as a solid. LC-MS: m/z=515 (M+H)⁺.

Step 14

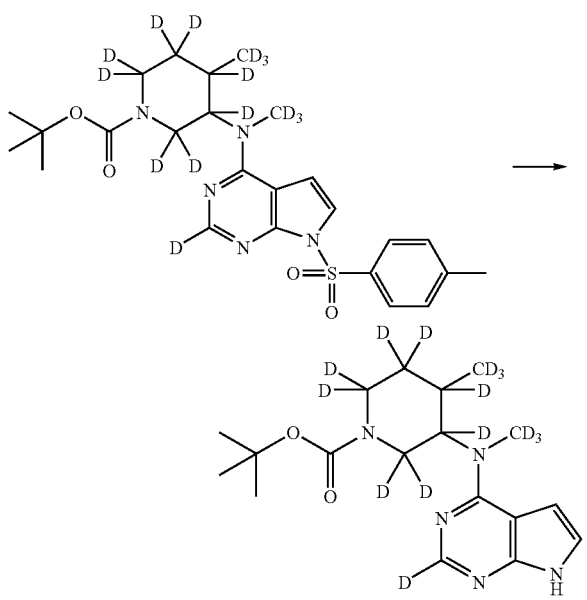

tert-Butyl 4-d₃-methyl-3-(d₃-methyl(2-d₁-7H-pyrrolo[2,3-d]pyrimidin-4-yl)amino)-2,2',3,4,5,5',6,6'-d₈-piperidine-1-carboxylate The procedure of Example 2, Step 5 was followed, but substituting tert-butyl 3-((2-d₁-7-tosyl-7H-pyrrolo[2,3-d]pyrimidin-4-yl)(d₃-methyl)amino)-4-d₃-methyl-2,2',3,4,5,5',6,6'-d₈-piperidine-1-carboxylate for tert-butyl 4-methyl-3-(d₃-methyl(2-d₁-7-tosyl-7H-pyrrolo[2,3-d]pyrimidin-4-yl)amino)piperidine-1-carboxylate. The title product was isolated as a foamy solid (130 mg; yield=90%). LC-MS: m/z=361 (M+H)⁺.

Step 15

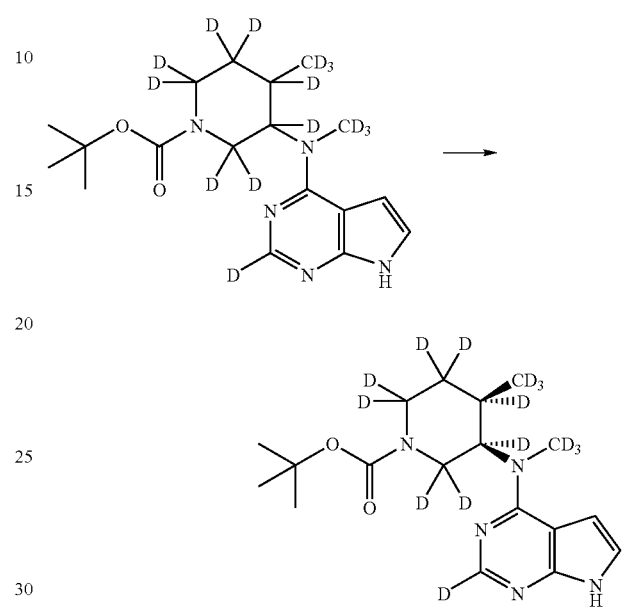

(3R,4R)-tert-Butyl 3-((2-d₁-7-tosyl-7H-pyrrolo[2,3-d]pyrimidin-4-yl)(d₃-methyl)amino)-4-d₃-methyl-2,2',3,4,5,5',6,6'-d₈-piperidine-1-carboxylate The enantiomer was isolated from tert-utbyl 4-d₃-methyl-3-(d₃-methyl(2-d₁-7H-pyrrolo[2,3-d]pyrimidin-4-yl)amino)-2,2',3,4,5,5',6,6'-d₈-piperidine-1-carboxylate by chiral resolution using chrial-prep-HPLC with the following conditions: column: Chiralpak IC2×25 cm (Waters 2767-1), 5 um Chiral-P(IC)001IC00CJ-LD016; mobile phase: hexane/isopropyl alcohol (85:15); detector: UV 254 nm. Retention time of desired enantiomer: 12.13 minutes, undesired enantiomer retention time: 15.15 minutes. ee %>99.8%. The title product was isolated as a yellow solid (0.1 g; yield=35%). LC-MS: m/z=361 (M+H)⁺.

Step 16

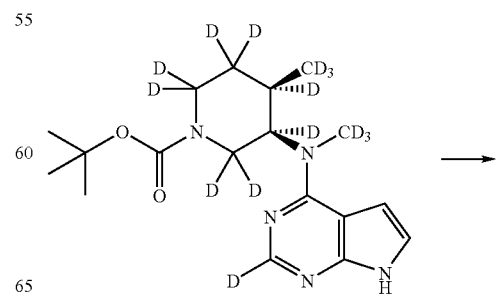

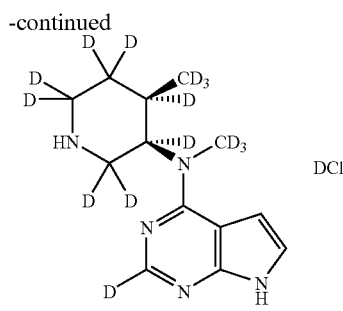

N-d₃-Methyl-N-((3R,4R)-4-d₃-methyl 2,2',3,4,5,5',6,6'-d₈-piperidin-3-yl)-2-d₁-7H-pyrrolo[2,3-d]pyrimidin-4-amine deuterochloride The procedure of Example 2, Step 7 was followed, but substituting (3R,4R)-tert-butyl 3-((2-d₁-7-tosyl-7H-pyrrolo[2,3-d]pyrimidin-4-yl)(d₃-methyl)amino)-4-d₃-methyl-2,2',3,4,5,5',6,6'-d₈-piperidine-1-carboxylate for 3-((3R,4R)-4-methyl-3-[d₃-methyl-(2-d₁-7H-pyrrolo[2,3-d]pyrimidin-4-yl)-amino]-piperidine)-1-carboxylic acid tert-butyl ester. The title product was isolated as a crude residue which was used in the next step without any further purification. LC-MS: m/z=261 (M+H)⁺.

Step 17

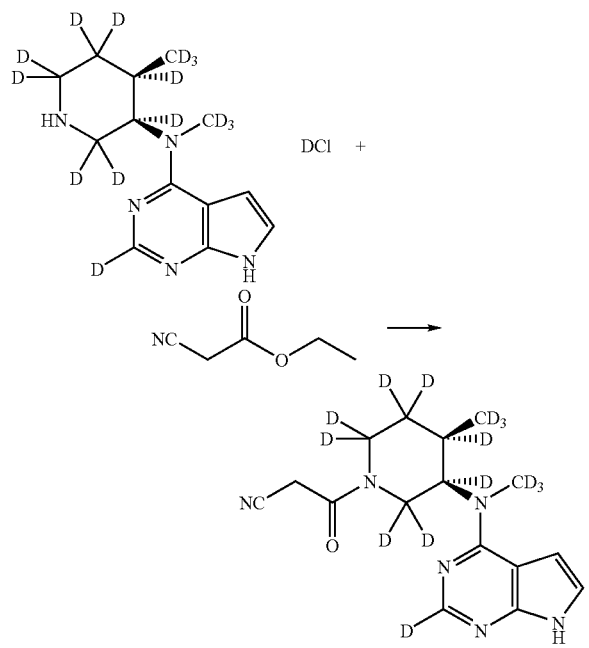

3-((3R,4R)-4-d₃-Methyl-3-(d₃-methyl(2-d₁-7H-pyrrolo[2,3-d]pyrimidin-4-yl)amino)-2,2',3,4,5,5',6,6'-d₈-piperidin-1-yl)-3-oxopropanenitrile (CP-690550-d₁₅)

The procedure of Example 1, Step 11 was followed but substituting N-d₃-methyl-N-((3R,4R)-4-d₃-methyl-2,2',3,4,5,5',6,6'-d₈-piperidin-3-yl)-2-d₁-7H-pyrrolo[2,3-d]pyrimidin-4-amine deuterochloride for N-methyl-N-((3R,4R)-4-methylpiperidin-3-yl)-7H-pyrrolo[2,3-d]pyrimidin-4- amine. The title product was isolated as a light yellow solid (50 mg; yield=63%). LC-MS: m/z=328 (M+H)⁺.

Step 18

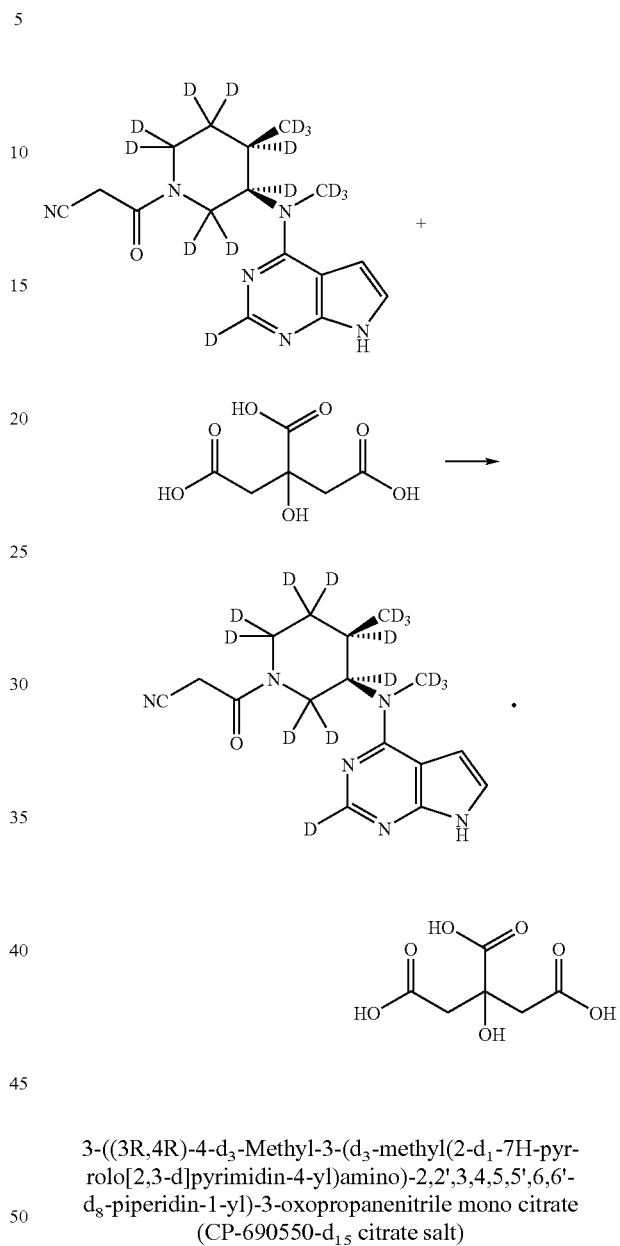

3-((3R,4R)-4-d₃-Methyl-3-(d₃-methyl(2-d₁-7H-pyrrolo[2,3-d]pyrimidin-4-yl)amino)-2,2',3,4,5,5',6,6'-d₈-piperidin-1-yl)-3-oxopropanenitrile mono citrate (CP-690550-d₁₅ citrate salt)

The procedure of Example 1, Step 12 was followed but substituting 3-((3R,4R)-4-d₃-methyl-3-(d₃-methyl(2-d₁-7H-pyrrolo[2,3-d]pyrimidin-4-yl)amino)-2,2',3,4,5,5',6,6'-d₈-piperidin-1-yl)-3-oxopropanenitrile for 3-((3R,4R)-4-methyl-3-(methyl(7H-pyrrolo[2,3-d]pyrimidin-4-yl)amino)piperidin-1-yl)-3-oxopropanenitrile. The title product was isolated as a white solid (54 mg; yield=90%). ¹H NMR (300 MHz, CD₃OD) δ: 7.35 (s, 1H), 6.89 (d, J=2.7 Hz, 1H), 3.91-4.08 (m, 2H), 2.94 (Ab$_q$, J=15.6 Hz, 2H), 2.81 (Ab$_q$, J=15.9 Hz, 2H). LC-MS: m/z=328 (MH—C₆H₈O₇)⁺.

The following compounds can generally be made using the methods described above. It is expected that these compounds when made will have activity similar to those described in the examples above.

85
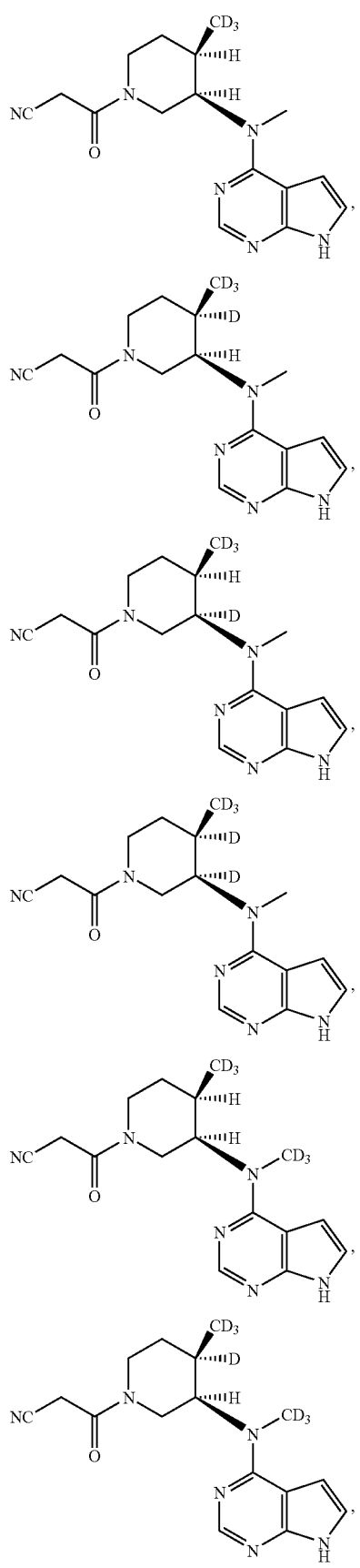
86
-continued
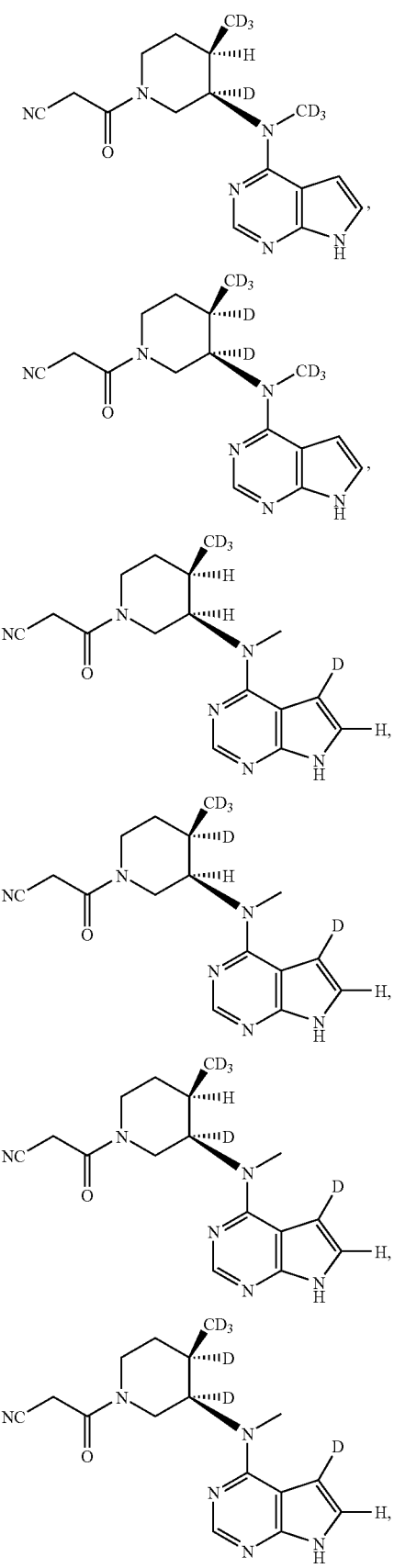

87
-continued
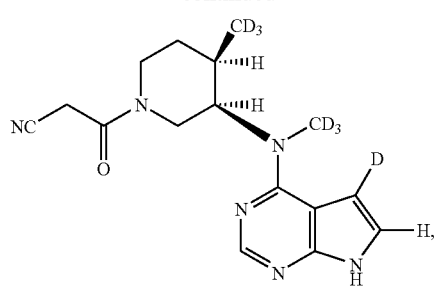
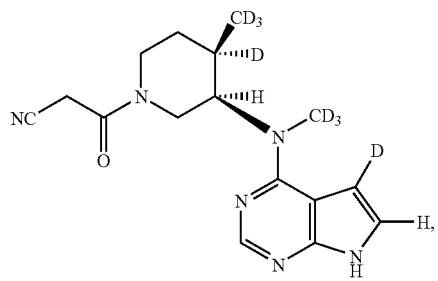
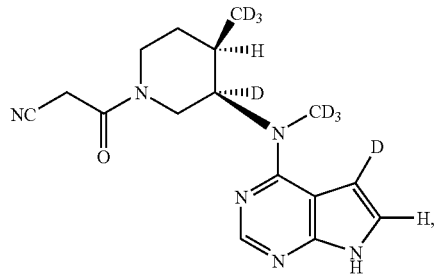
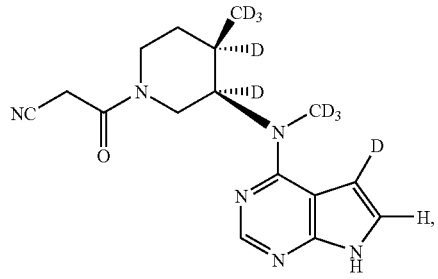
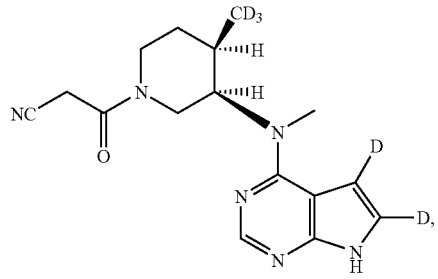
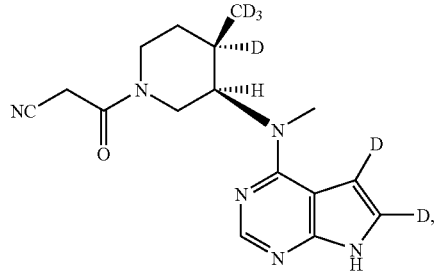
88
-continued
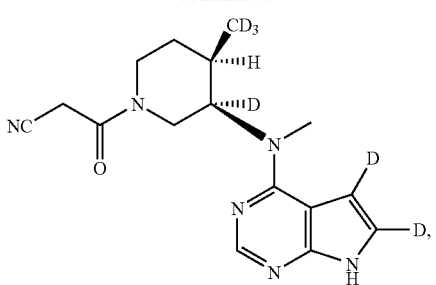
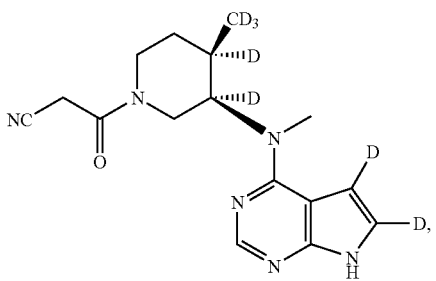
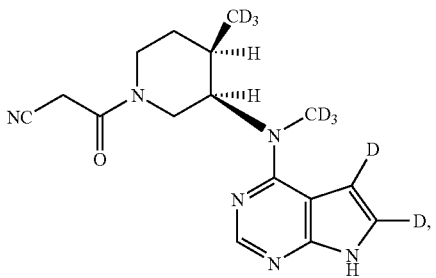
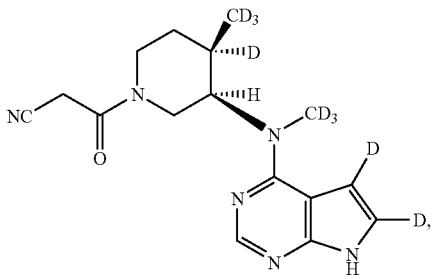
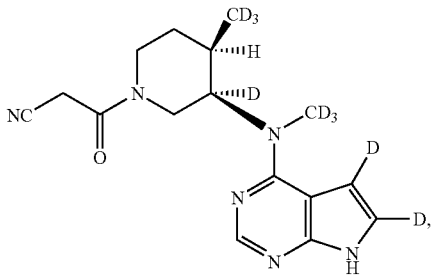
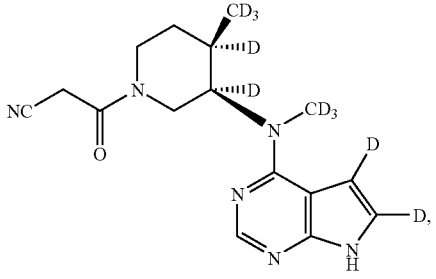

89
-continued
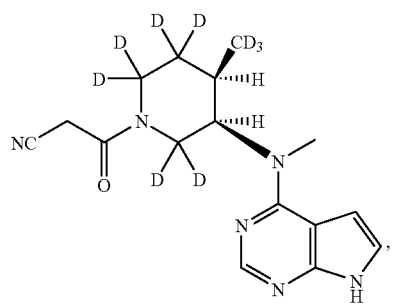
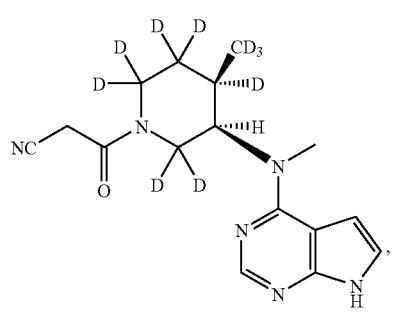
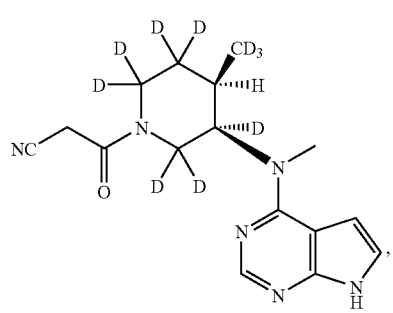
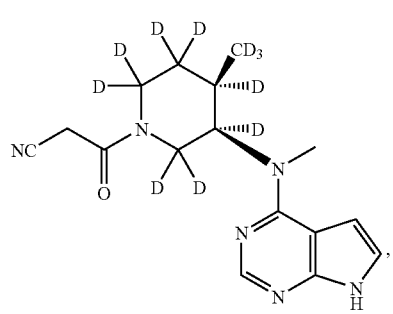
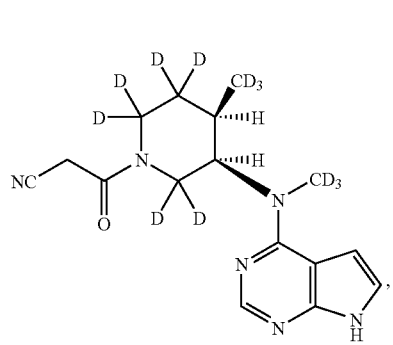
90
-continued
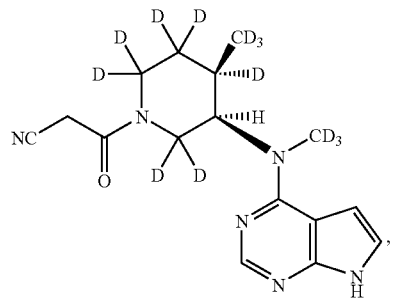
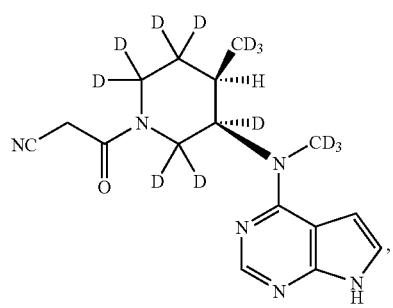
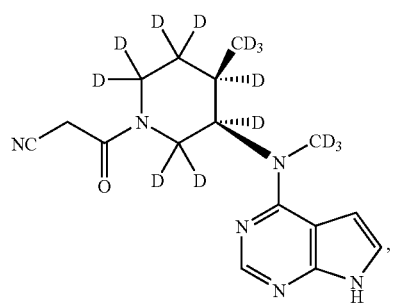
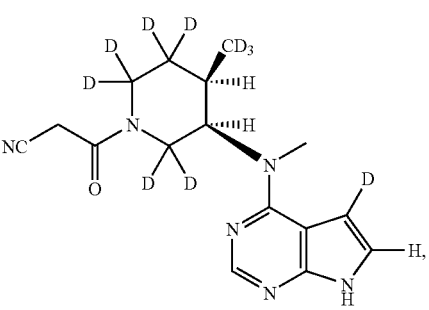
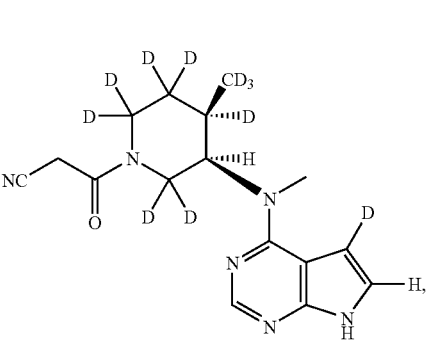

91
-continued
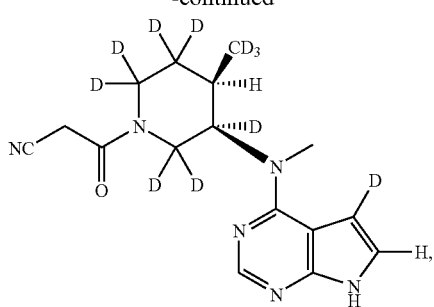
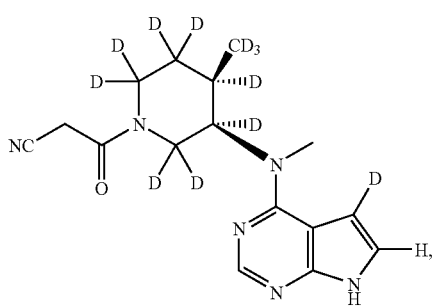
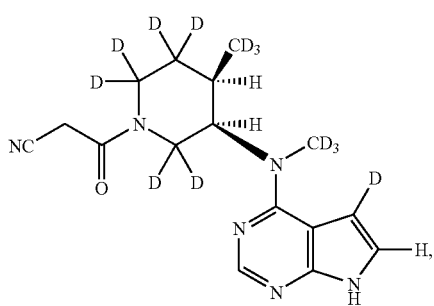
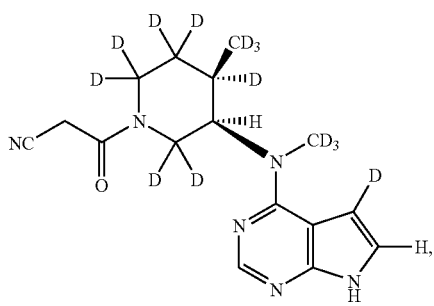
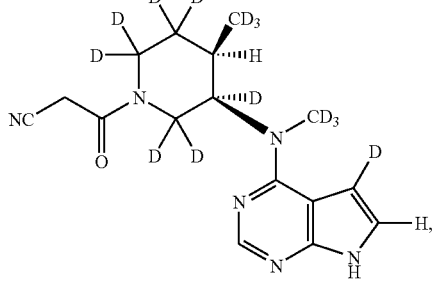
92
-continued
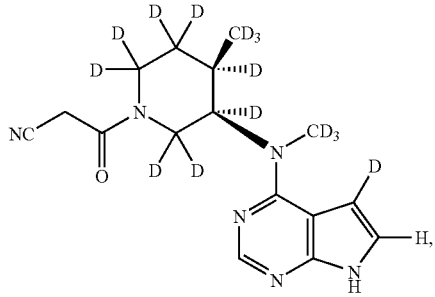
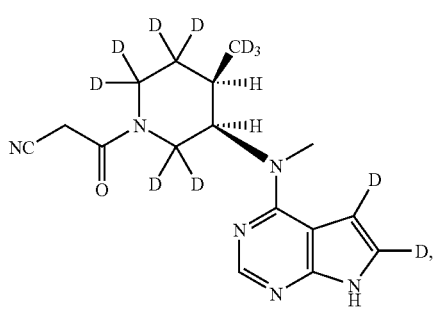
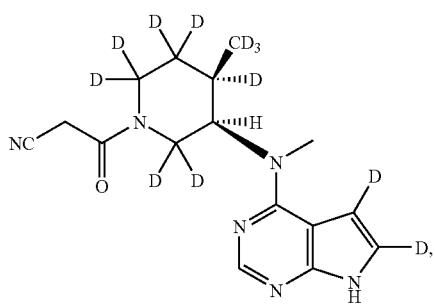
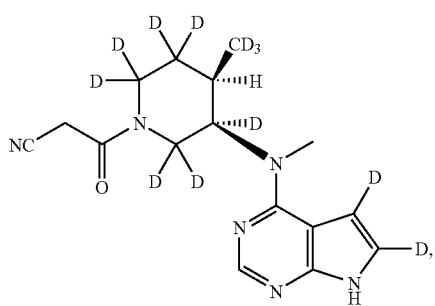
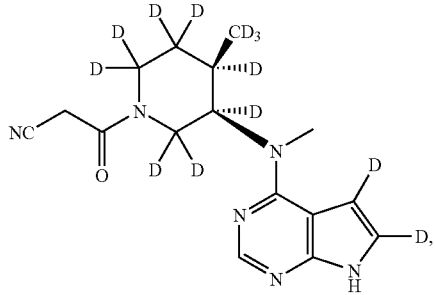

93
-continued
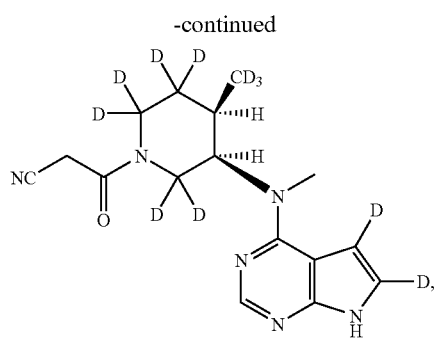
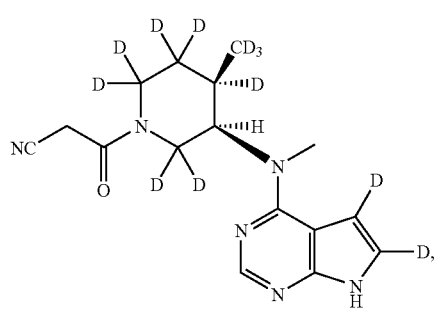
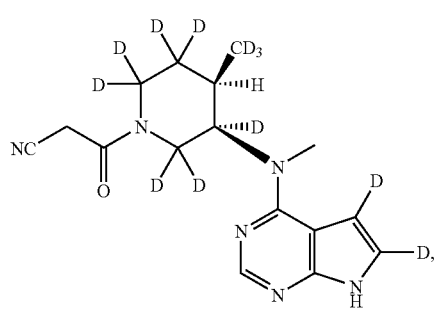
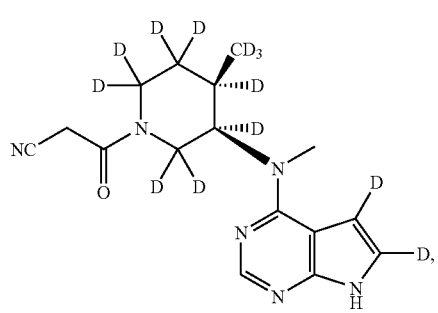
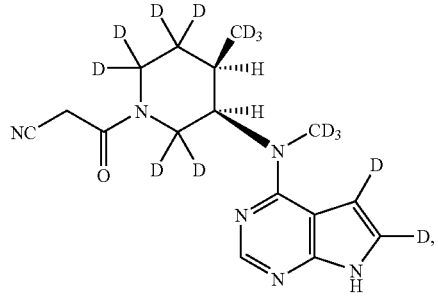
94
-continued
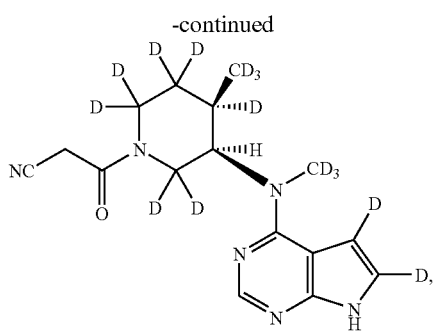
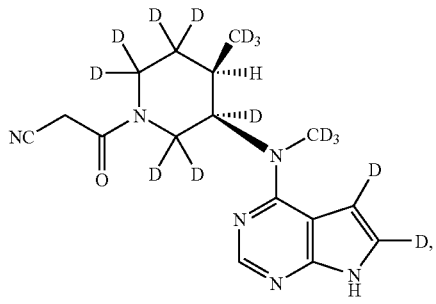
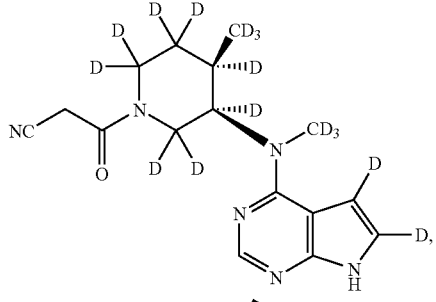
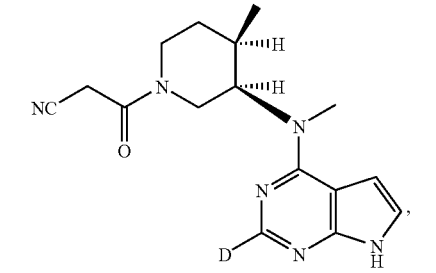
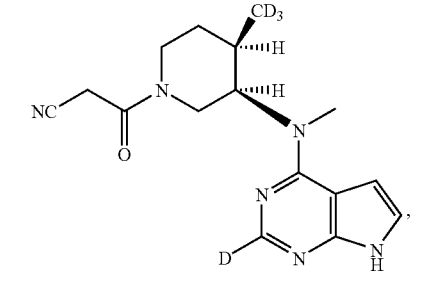
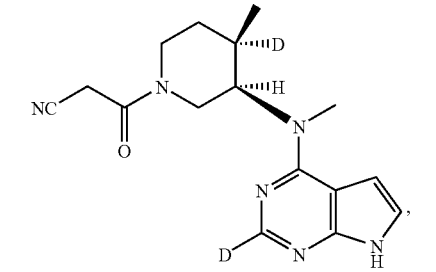

95
-continued
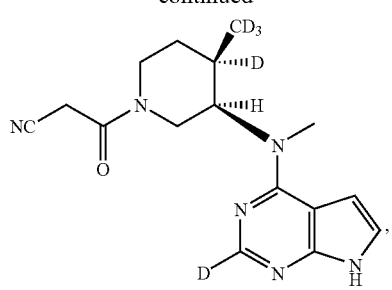
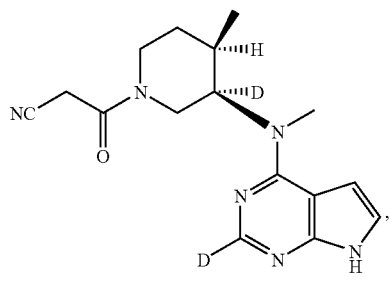
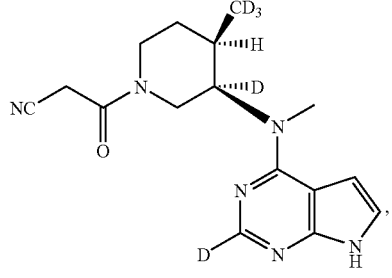
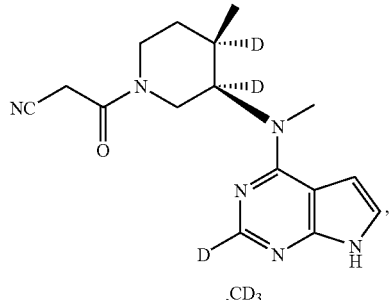
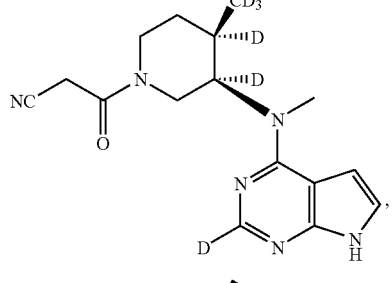
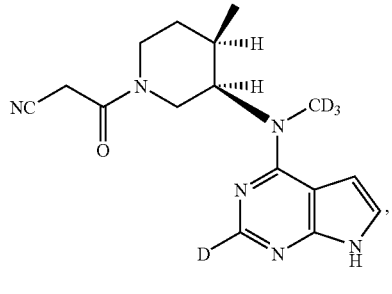
96
-continued
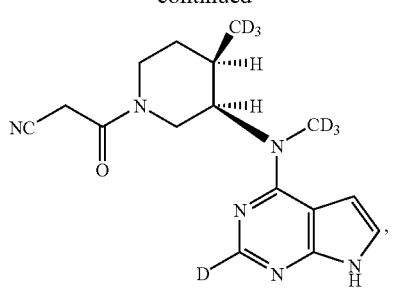
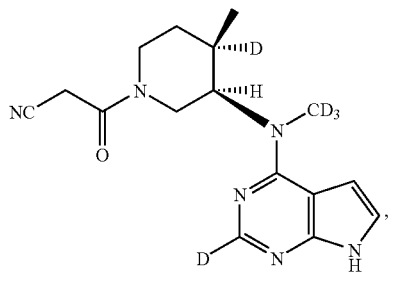
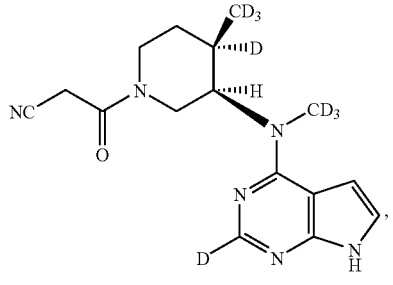
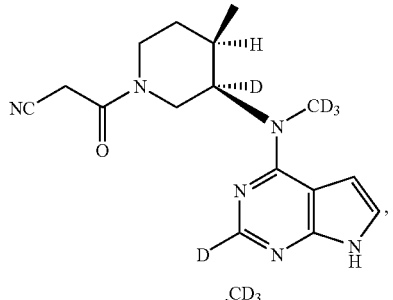
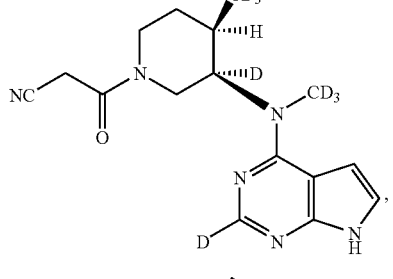
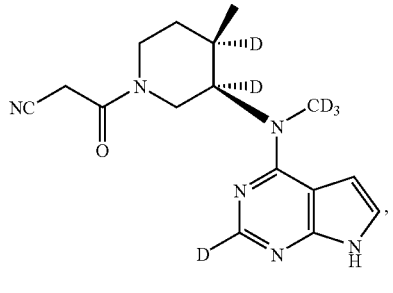

97
-continued
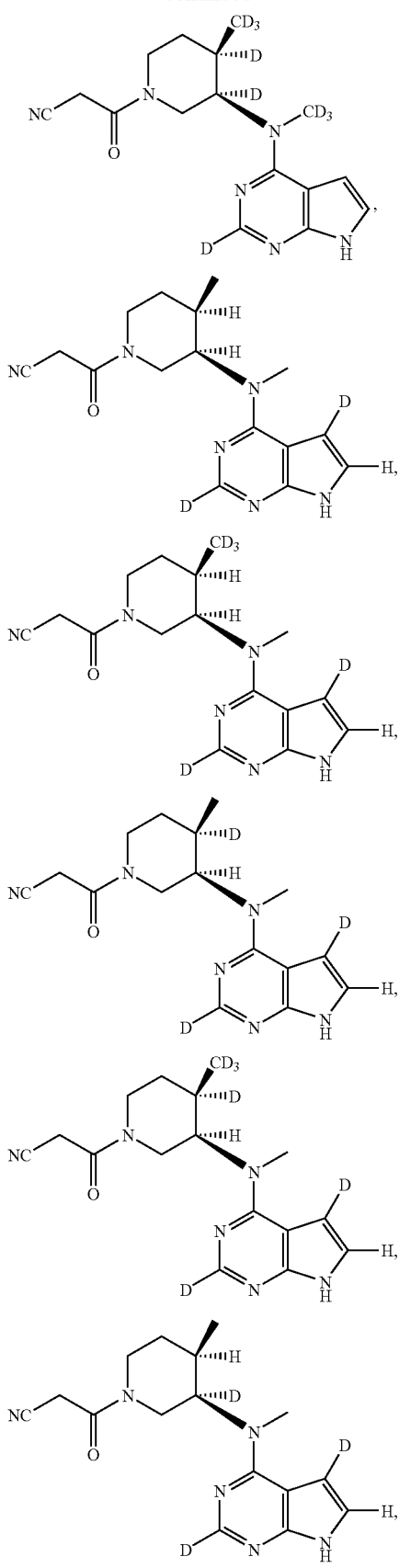
98
-continued
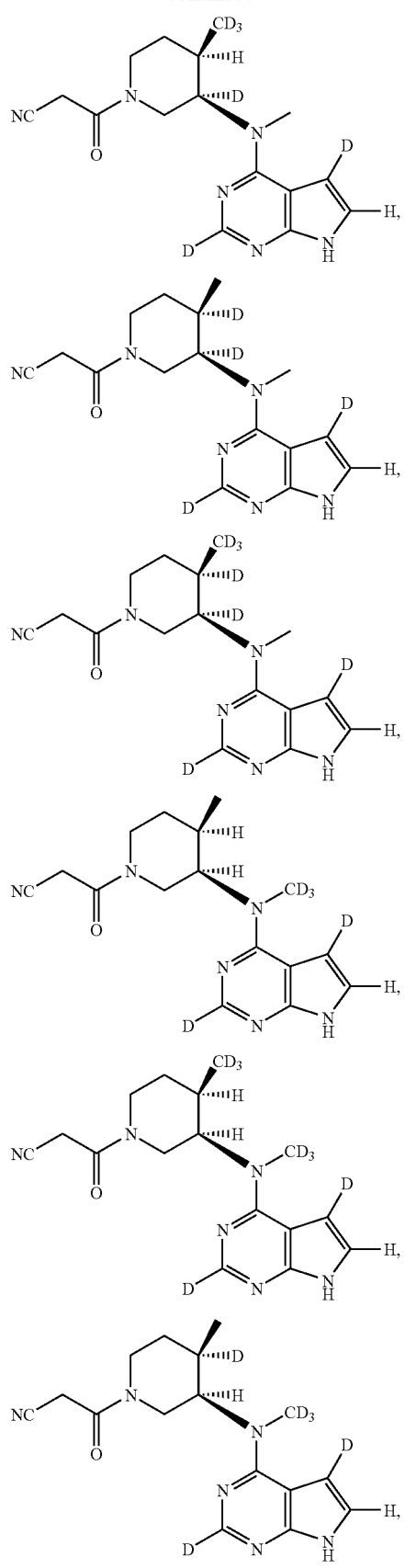

99
-continued
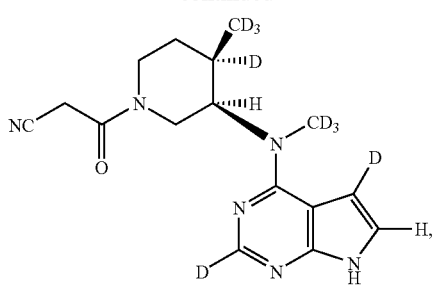
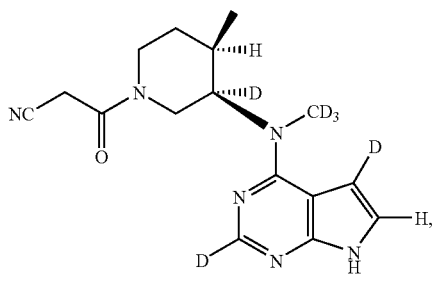
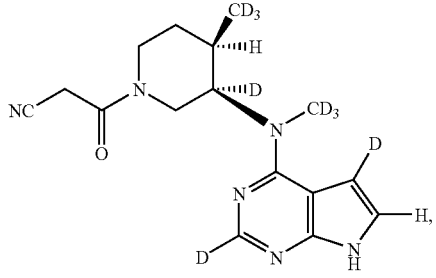
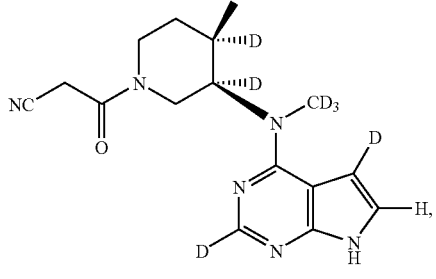
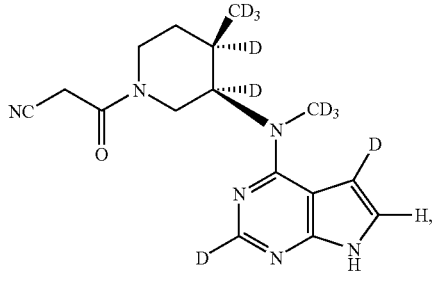
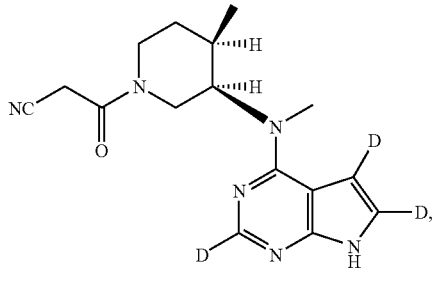
100
-continued
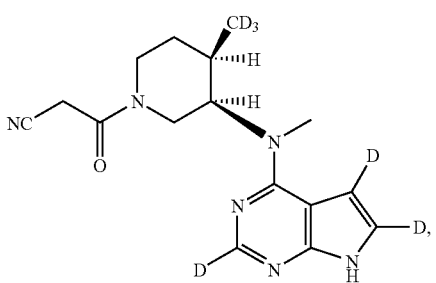
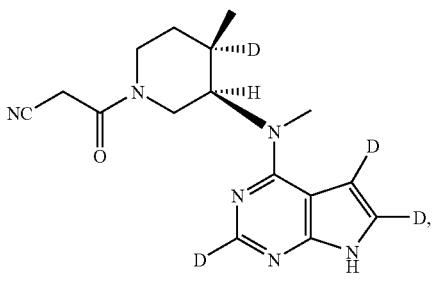
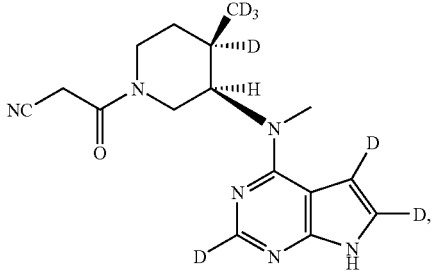
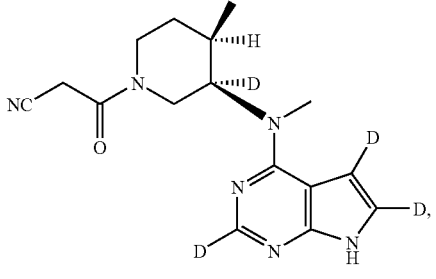
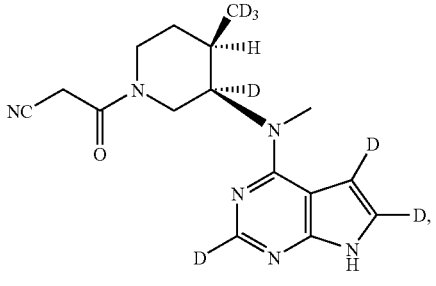
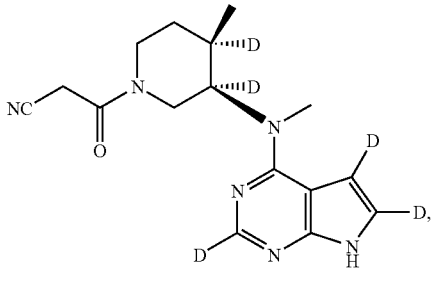

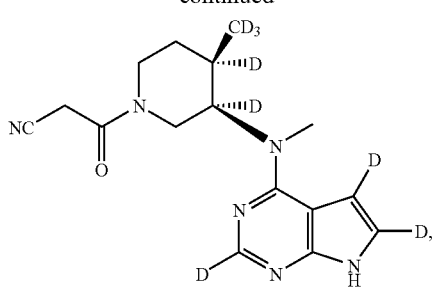
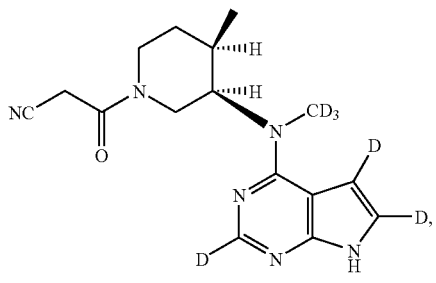
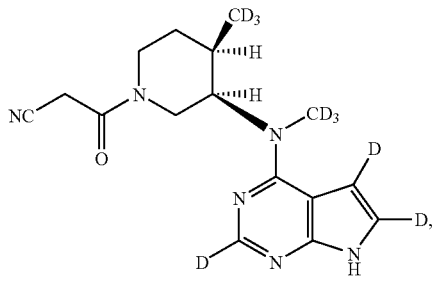
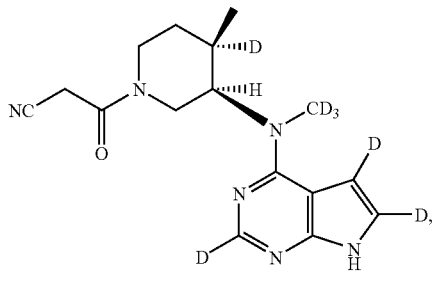
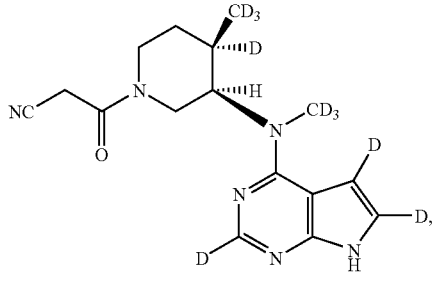
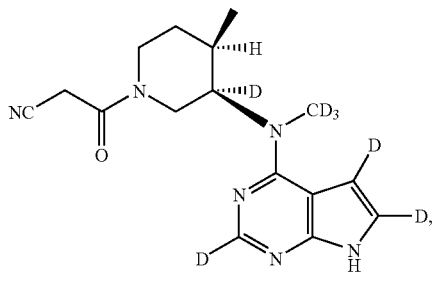
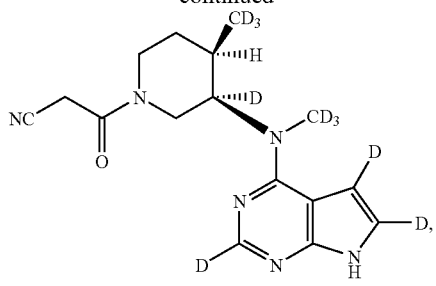
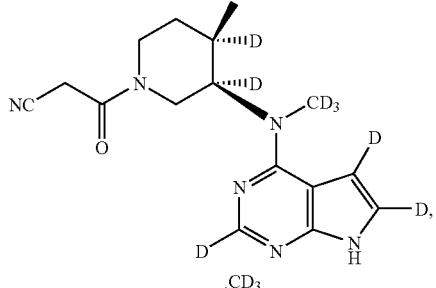
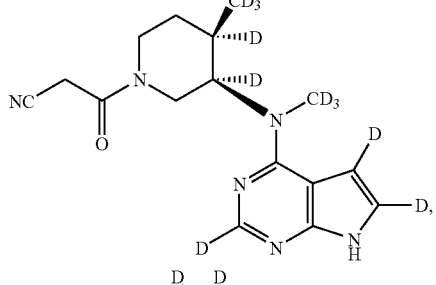
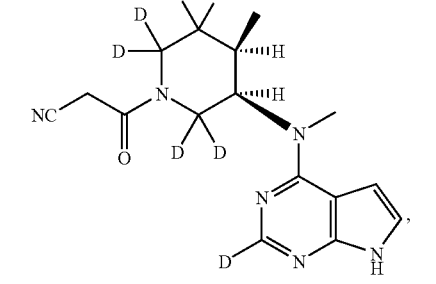
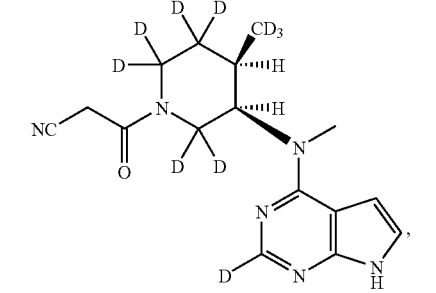
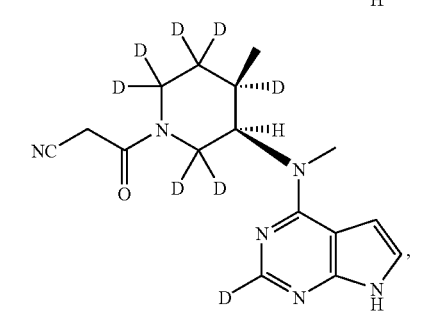

103
-continued
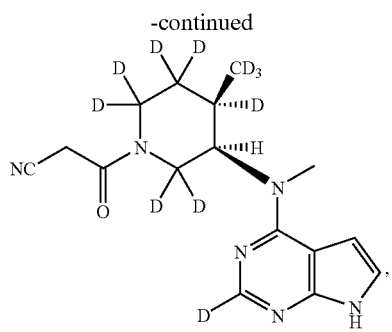
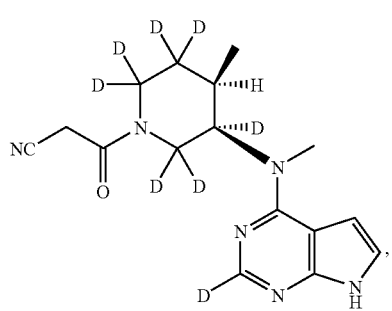
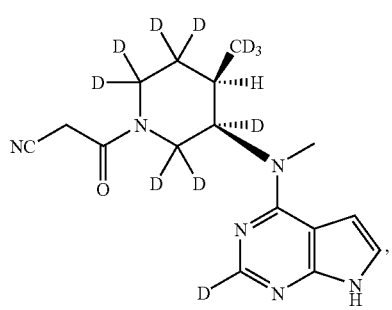
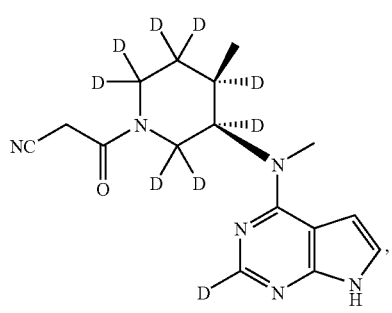
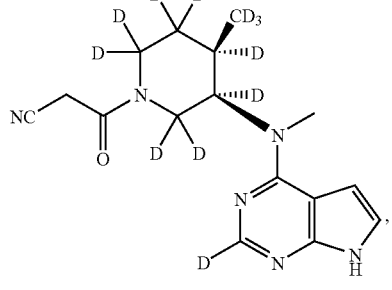
104
-continued
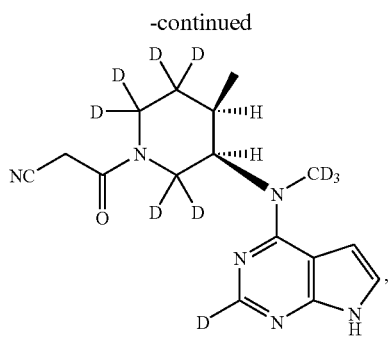
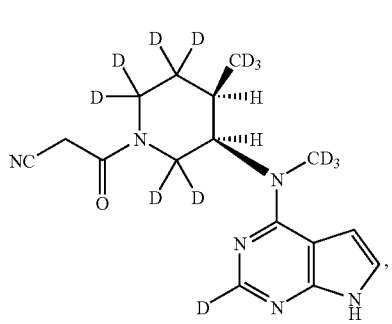
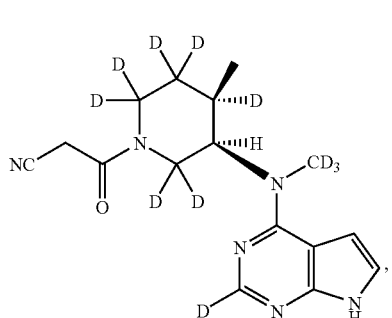
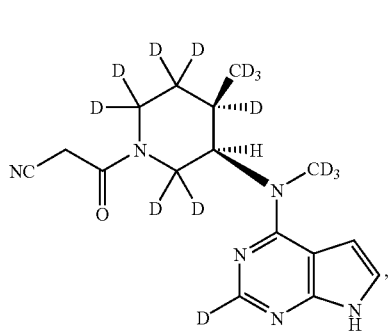
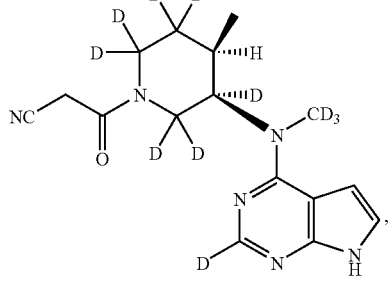

| 105 | 106 |
|---|---|
| -continued | -continued |
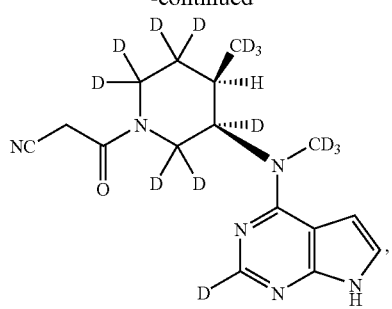
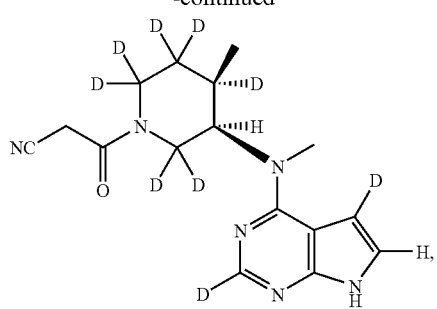
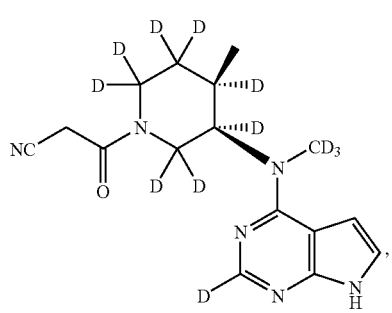
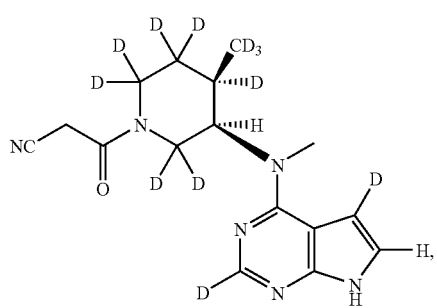
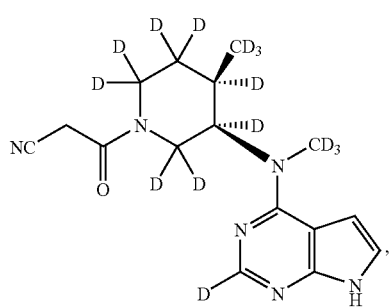
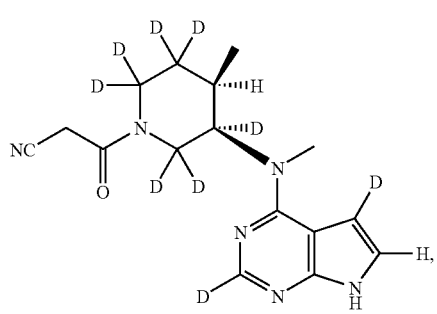
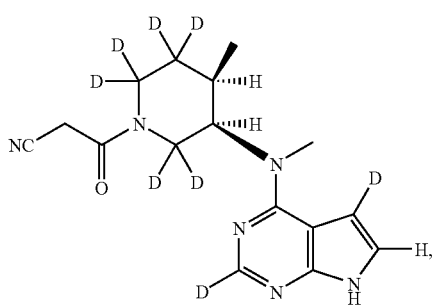
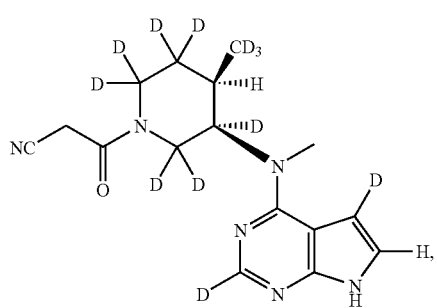
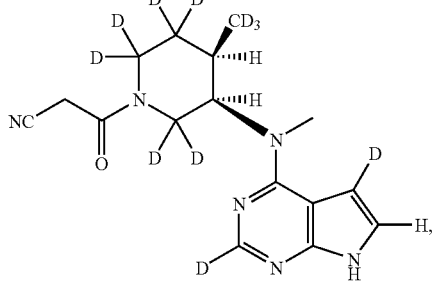
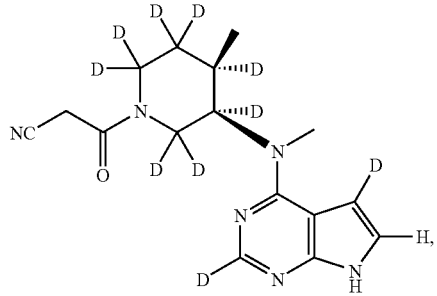

107
-continued
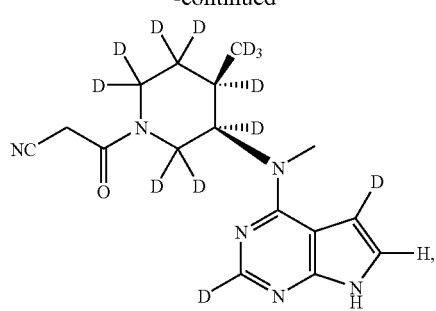
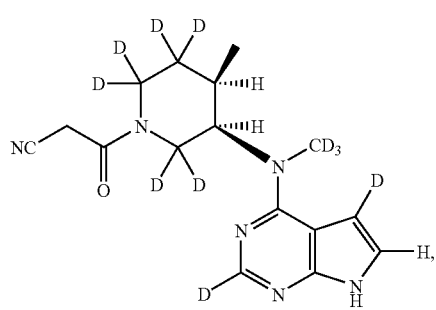
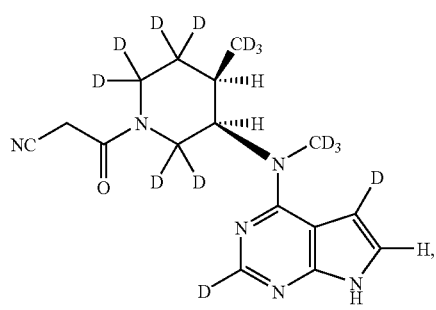
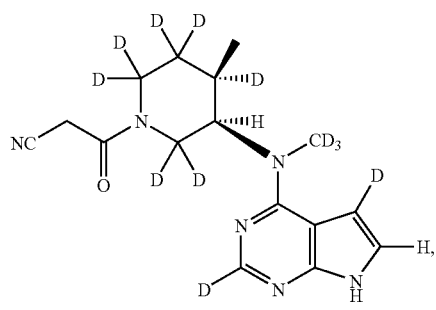
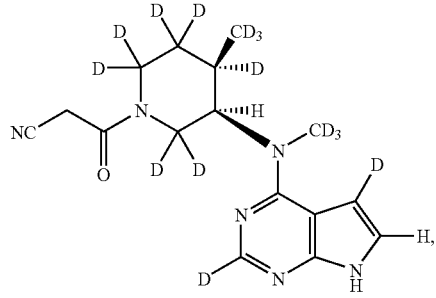
108
-continued
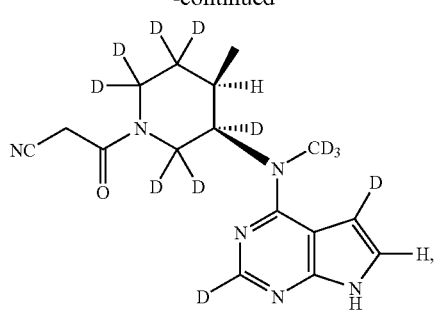
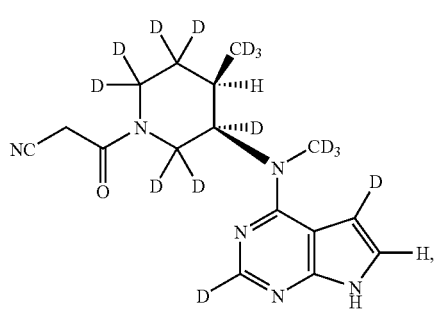
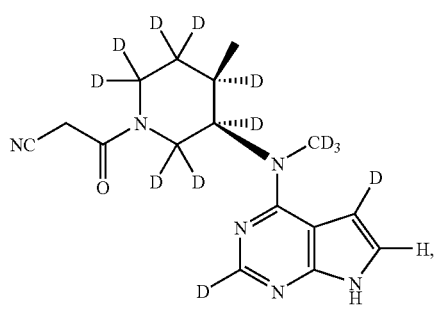
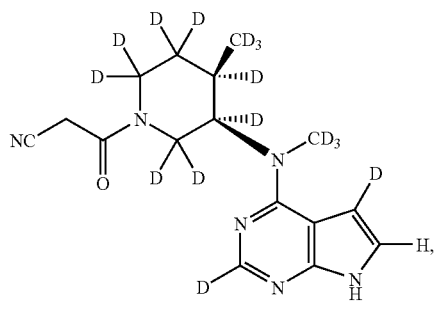
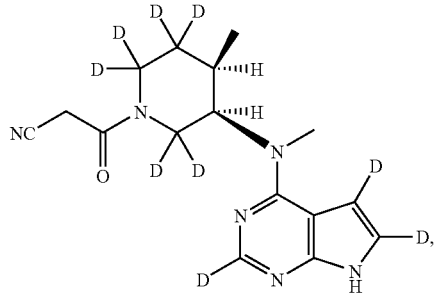

109
-continued
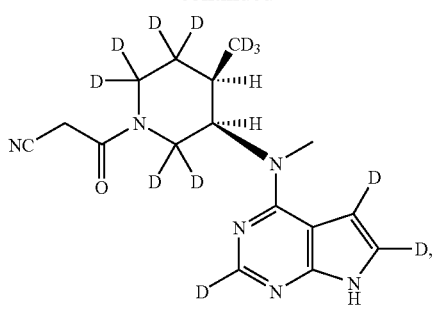
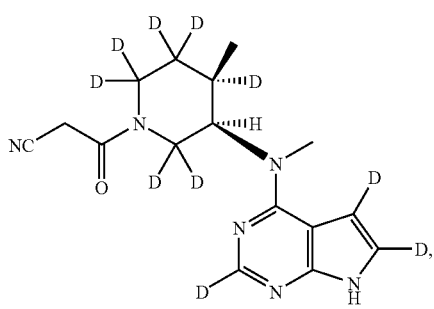
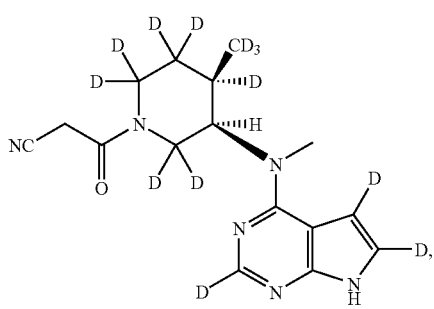
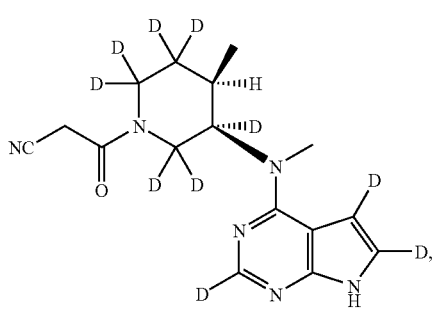
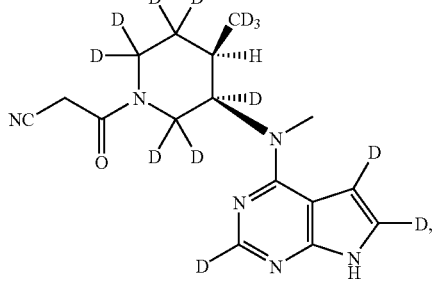
110
-continued
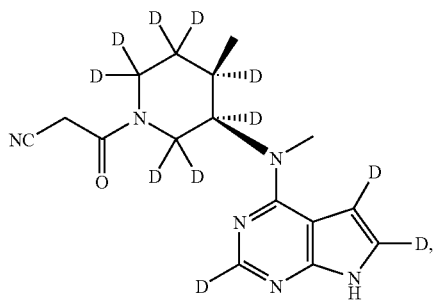
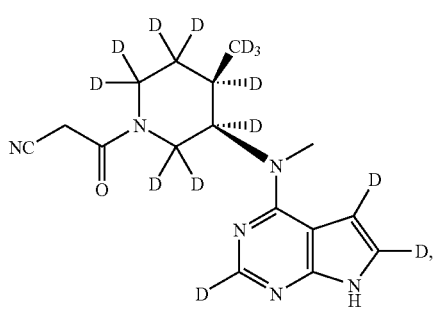
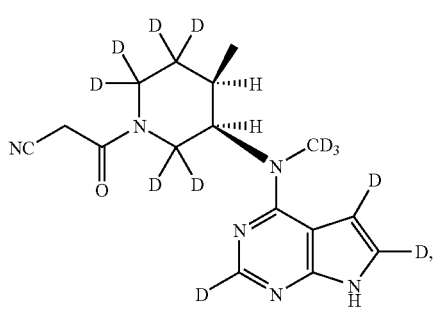
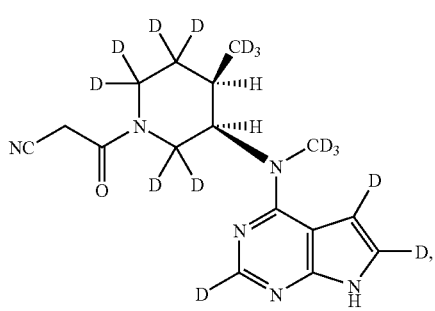
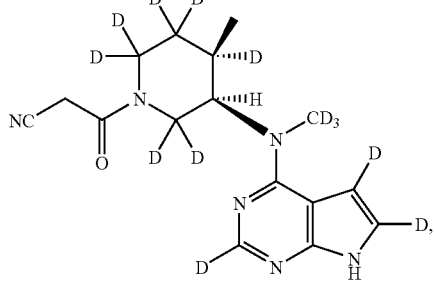

111
-continued
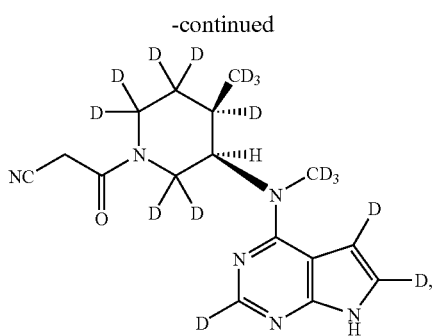
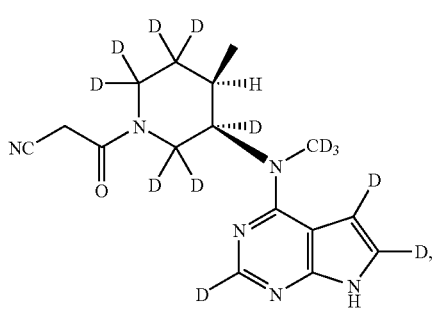
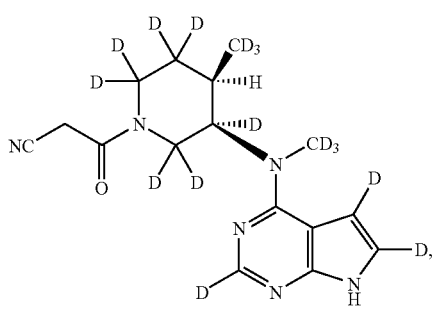
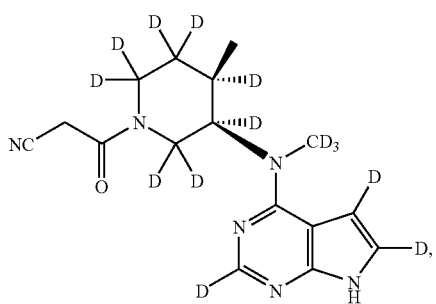
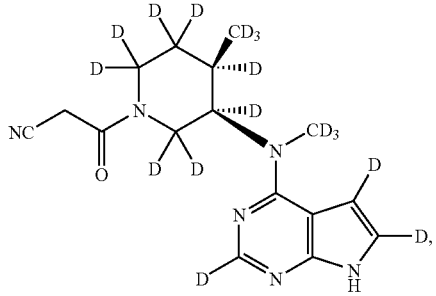
112
-continued
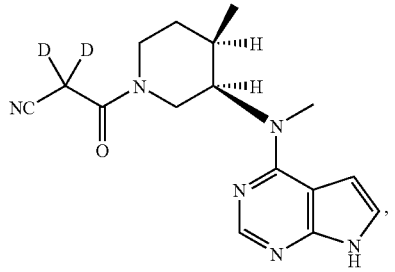
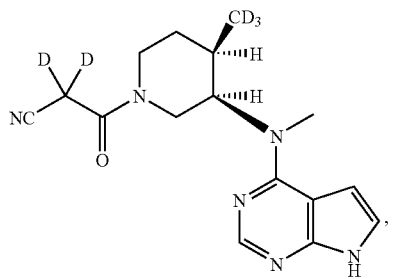
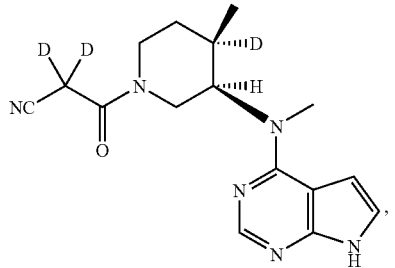
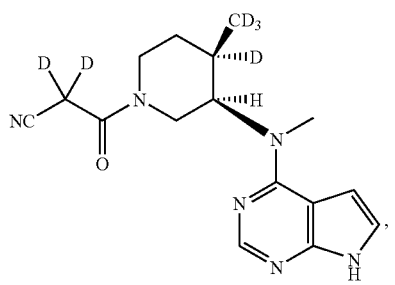
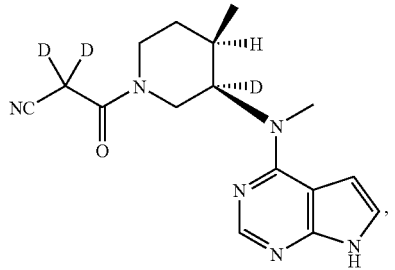
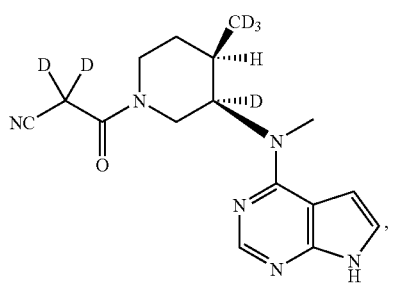

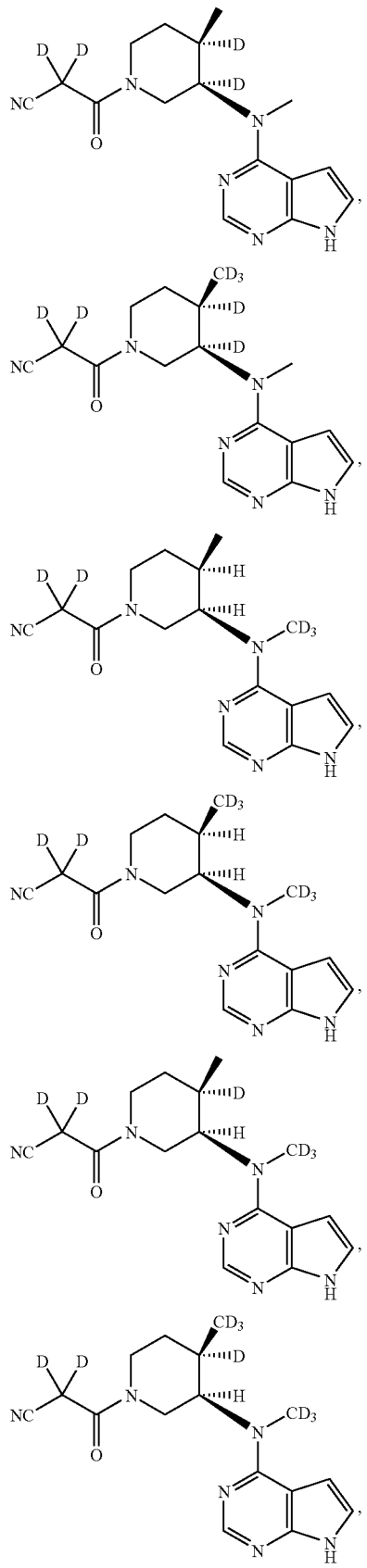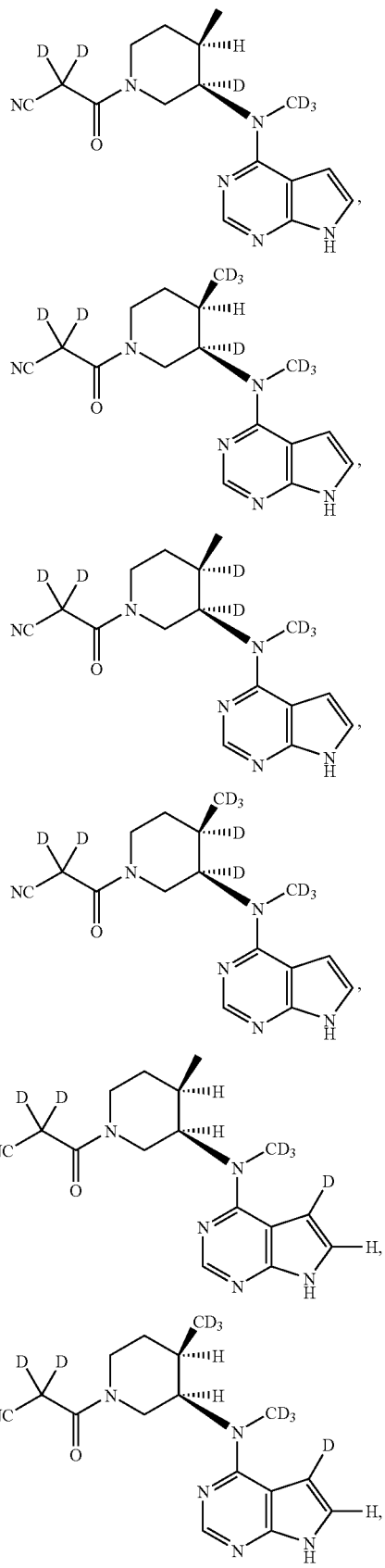

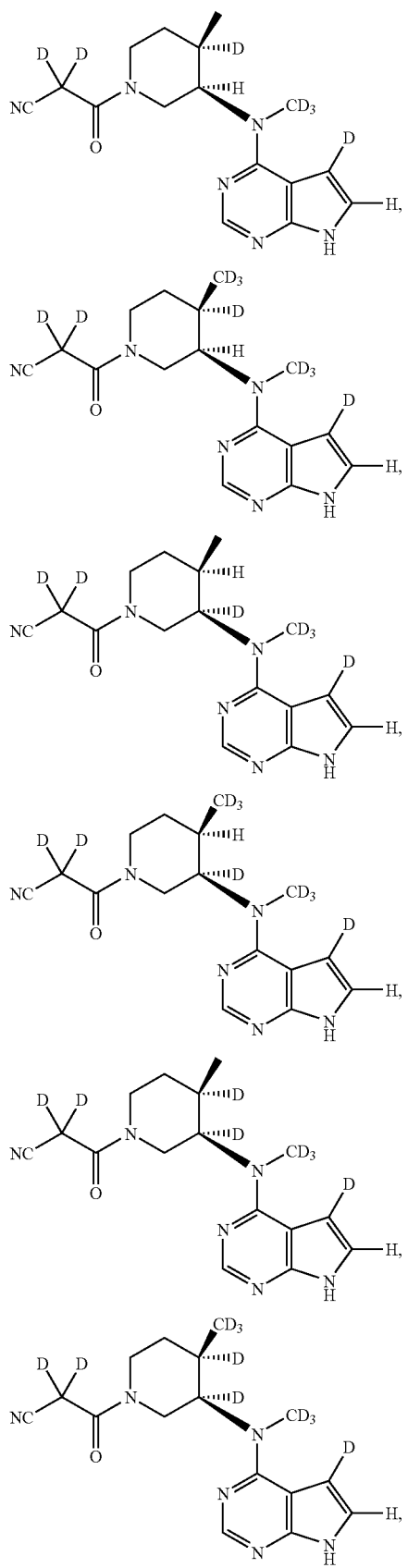
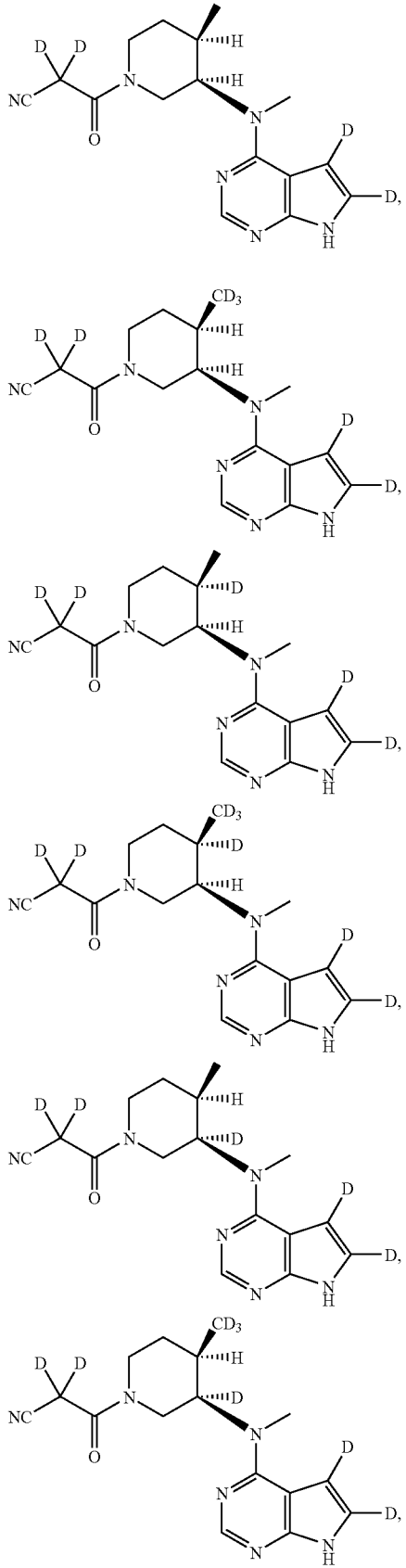

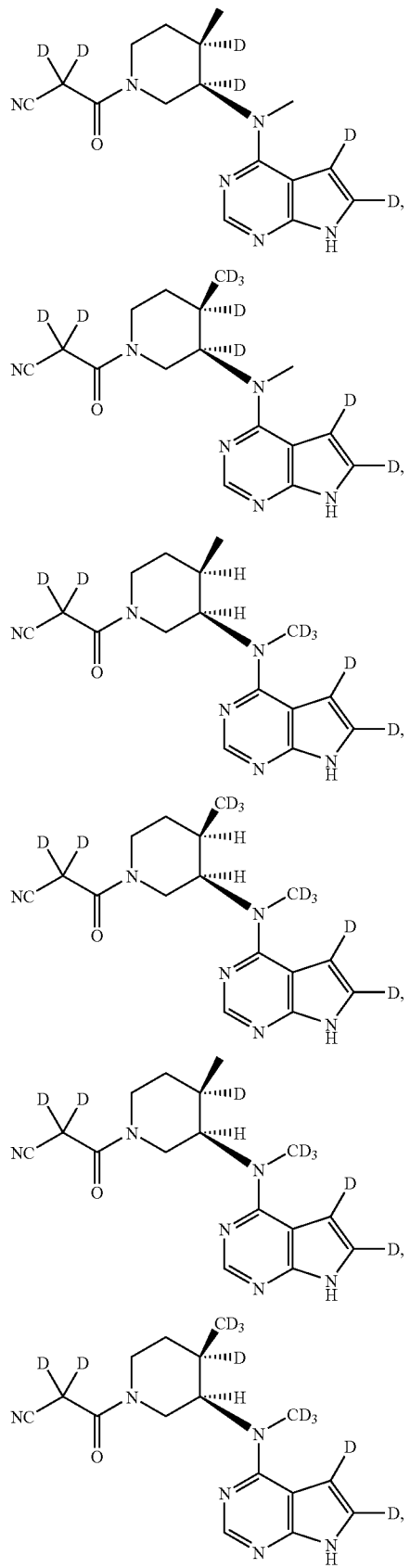
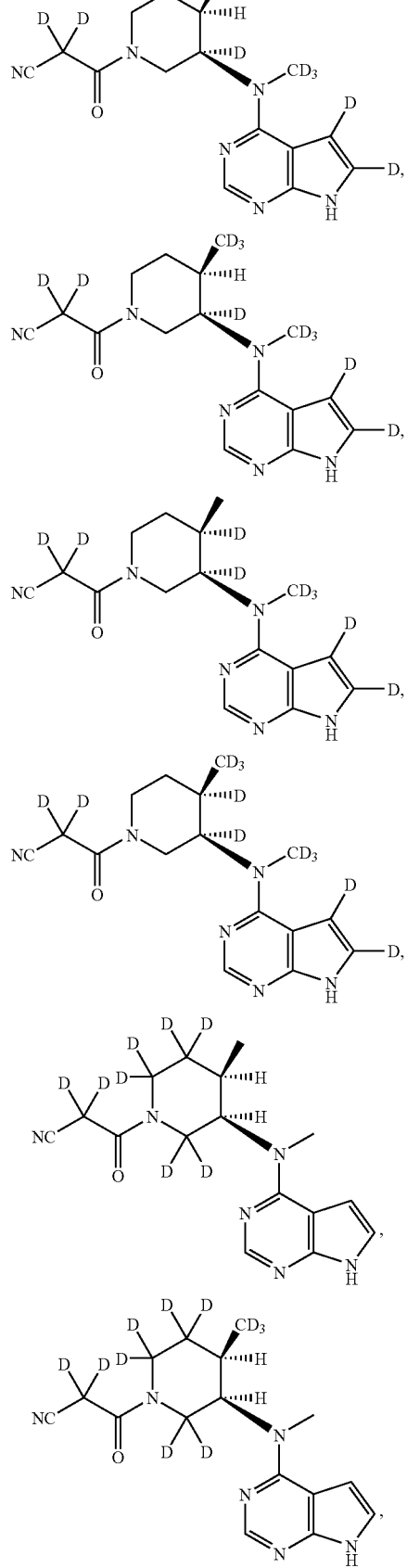

119
-continued
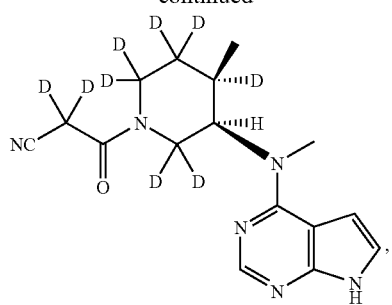
,
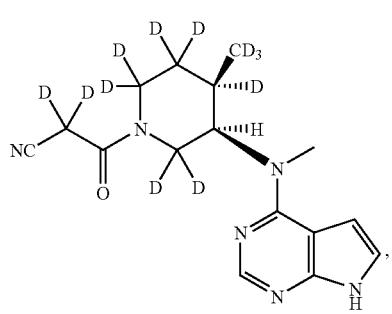
,
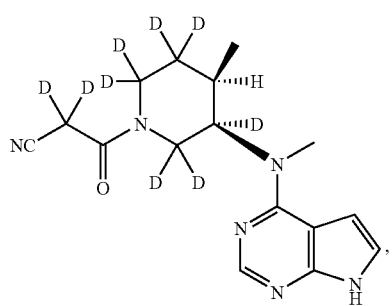
,
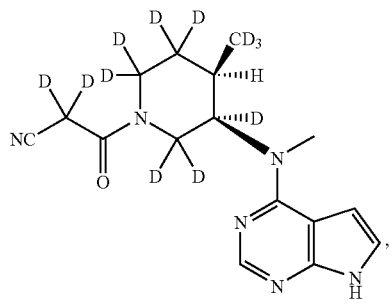
,
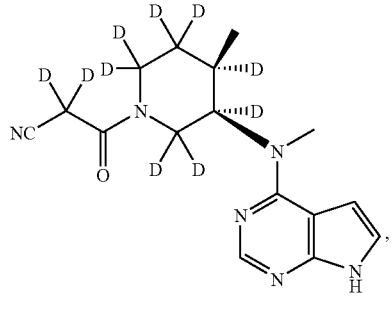
,
120
-continued
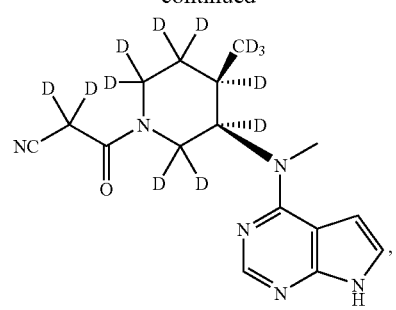
,
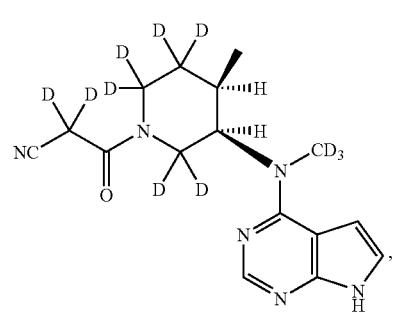
,
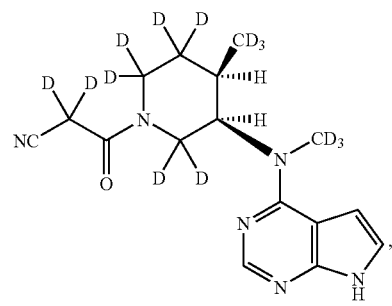
,
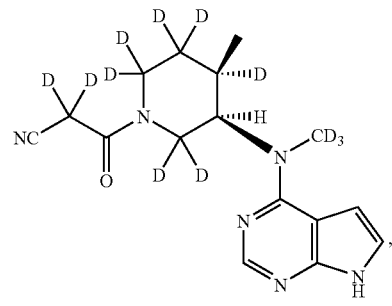
,
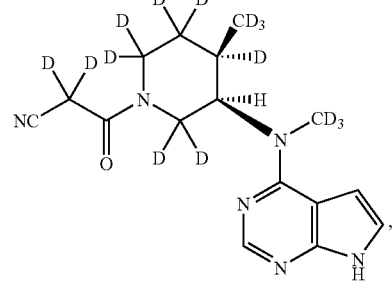
, 121
-continued
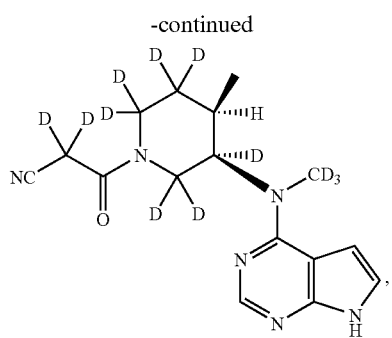
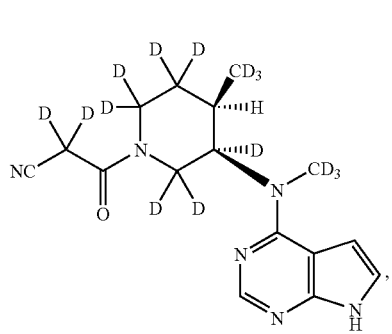
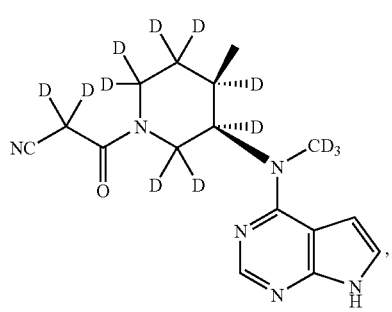
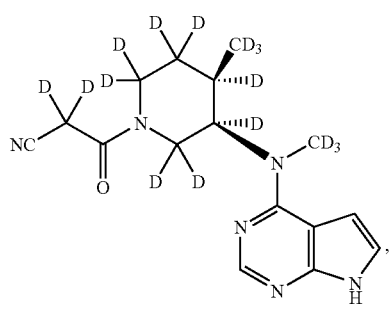
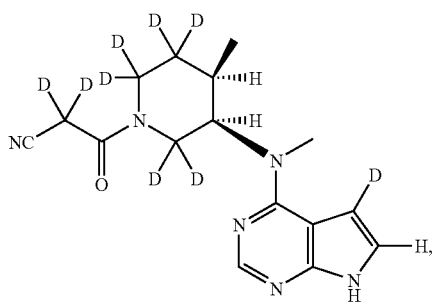
122
-continued
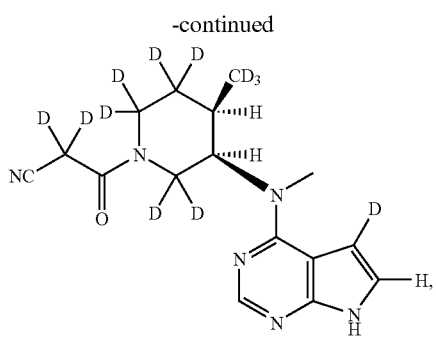
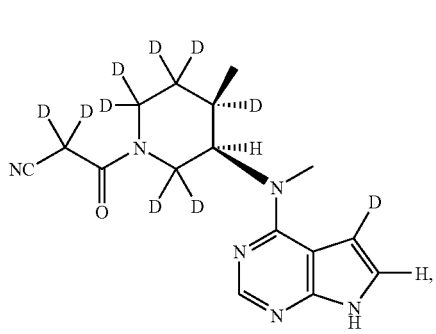
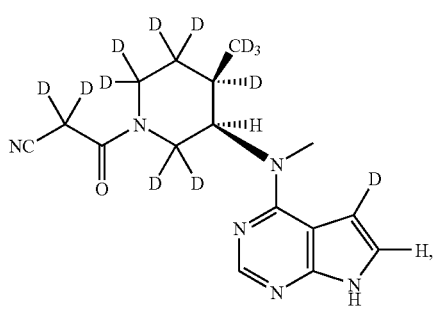
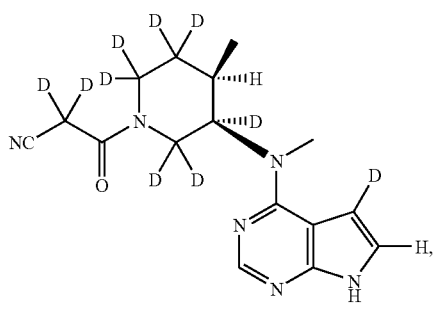
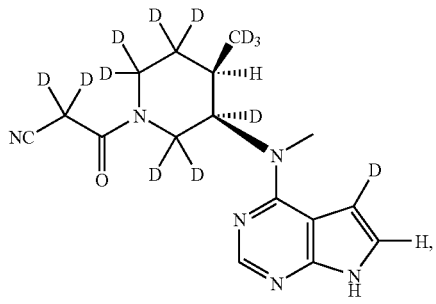

123
-continued
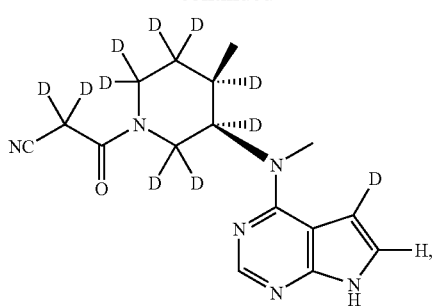
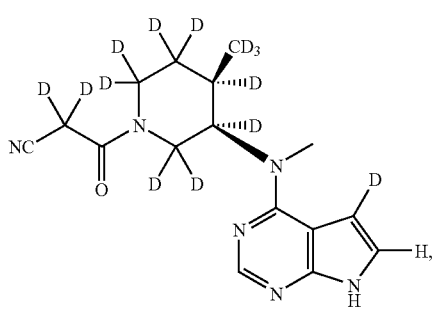
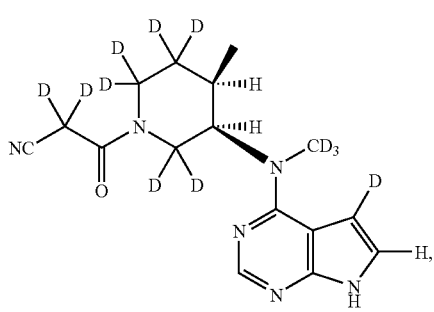
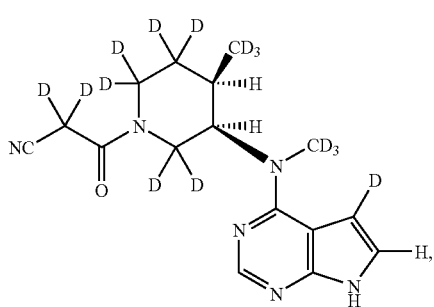
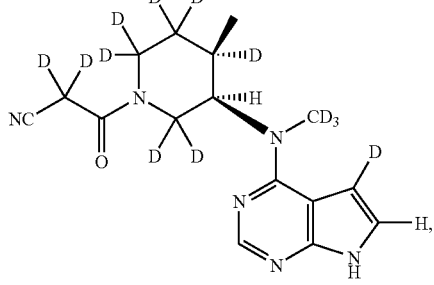
124
-continued
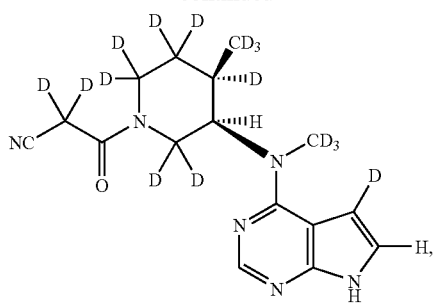
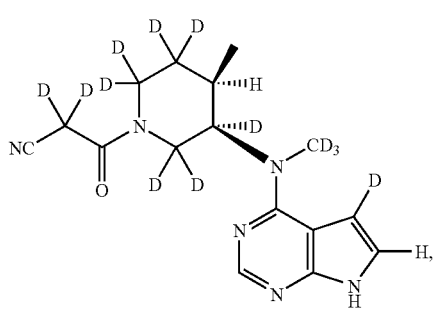
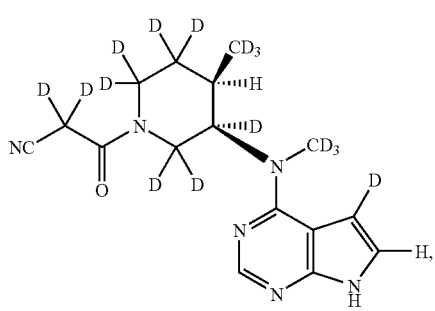
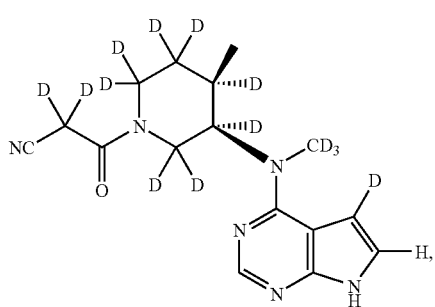
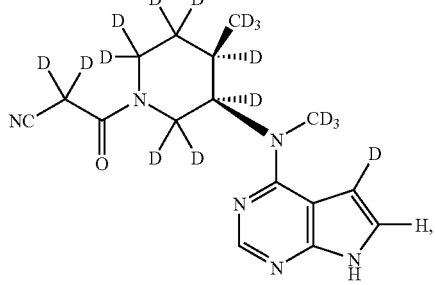

125
-continued
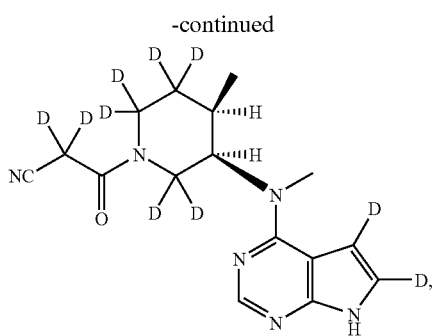
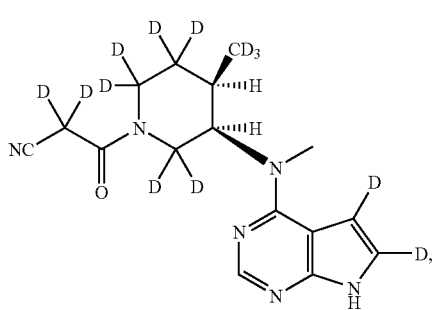
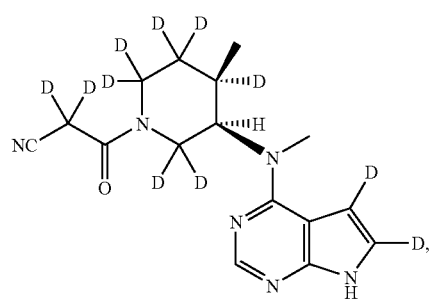
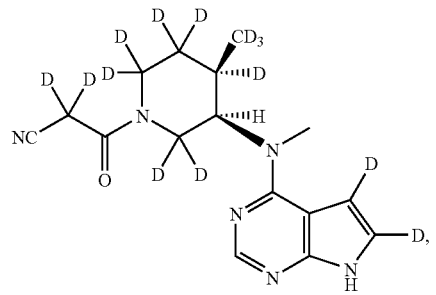
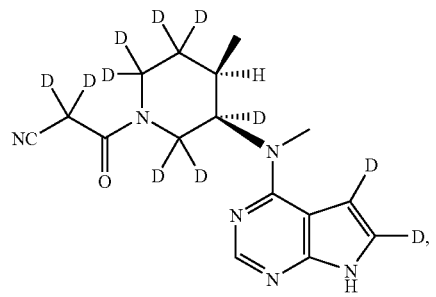
126
-continued
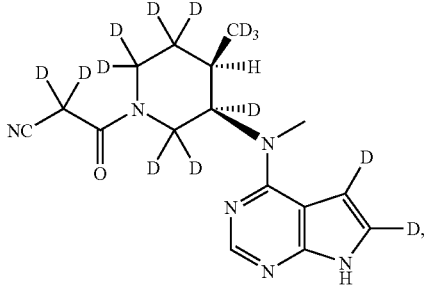
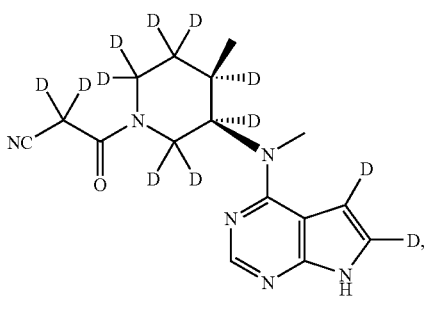
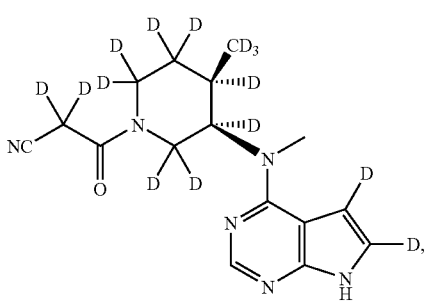
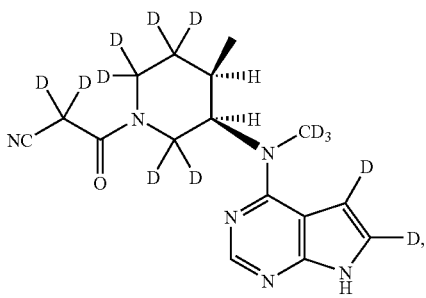
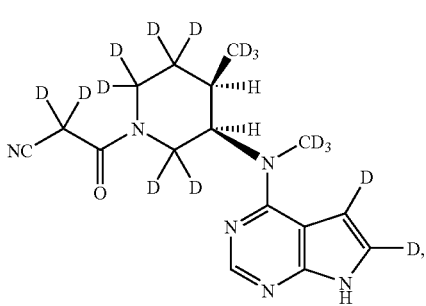

127
-continued
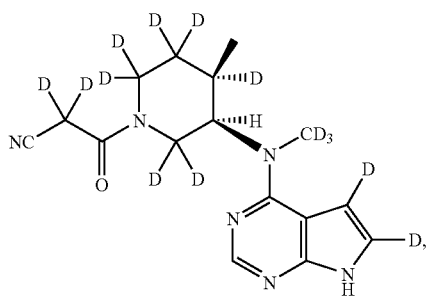
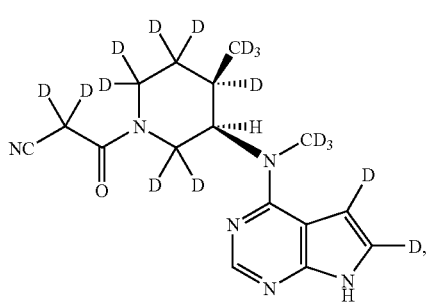
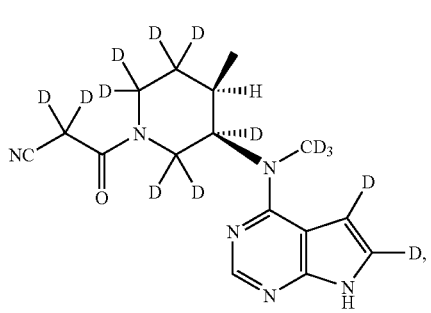
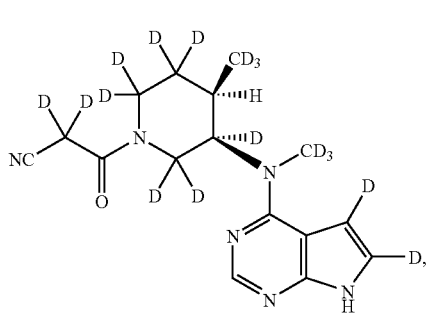
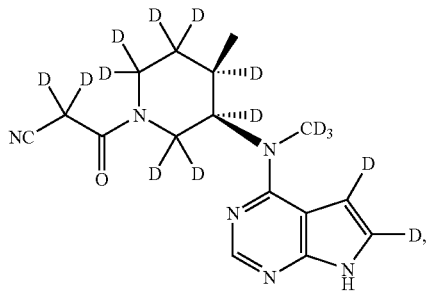
128
-continued
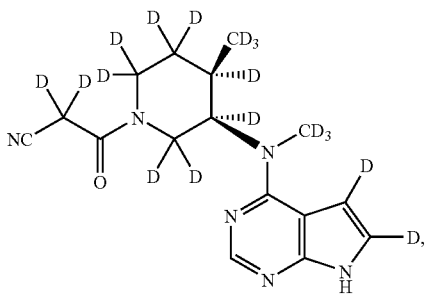
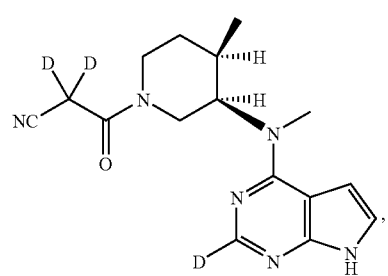
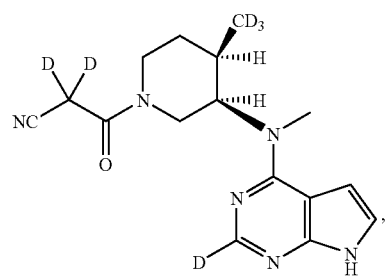
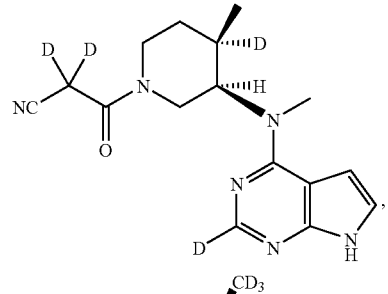
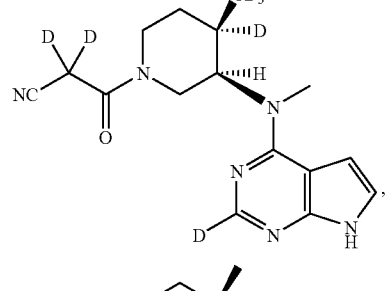
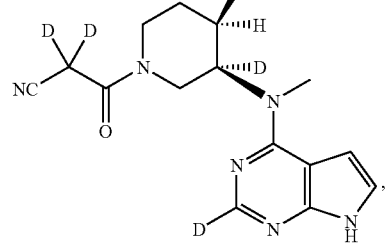

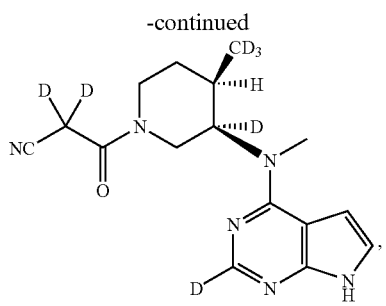
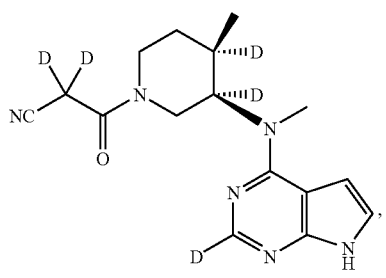
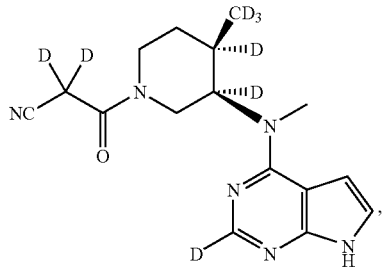
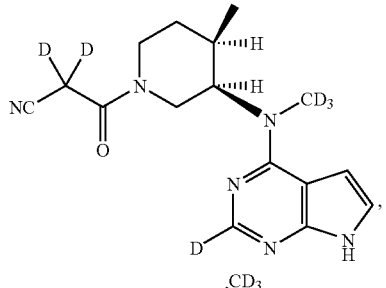
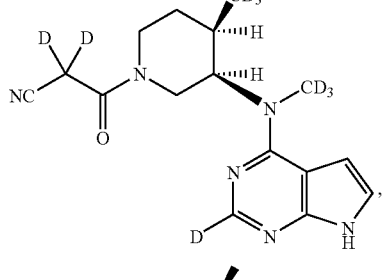
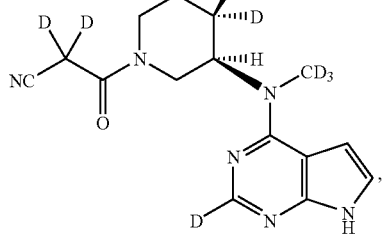
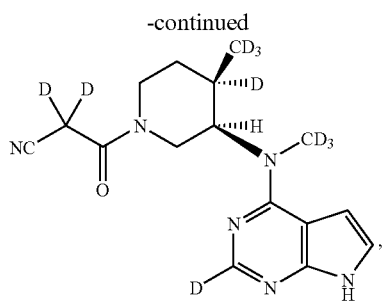

131
-continued
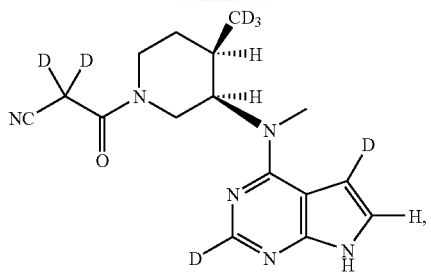
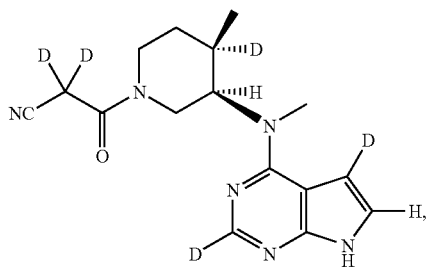
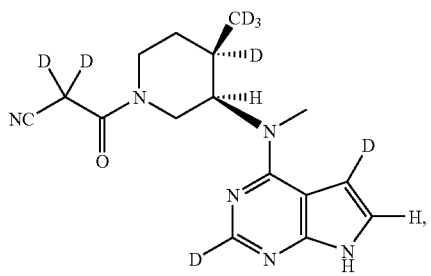
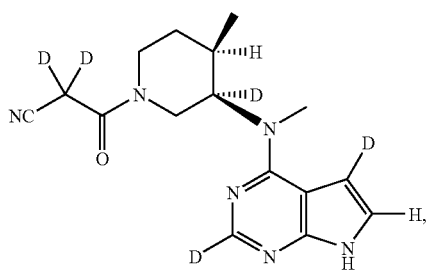
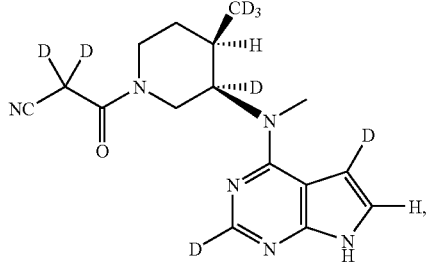
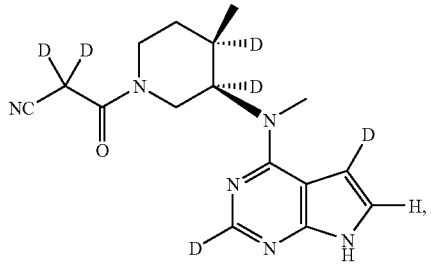
132
-continued
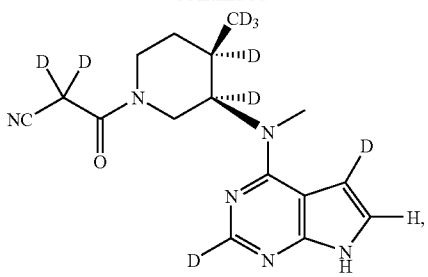
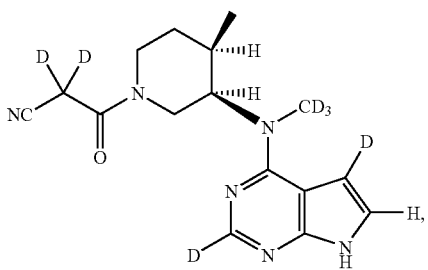
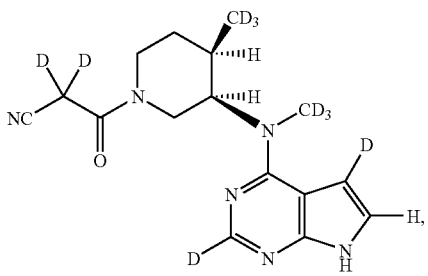
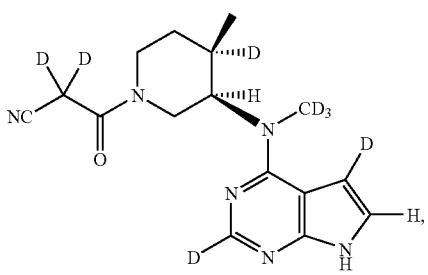
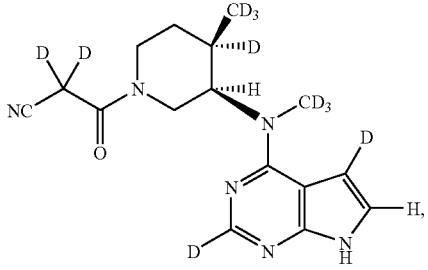
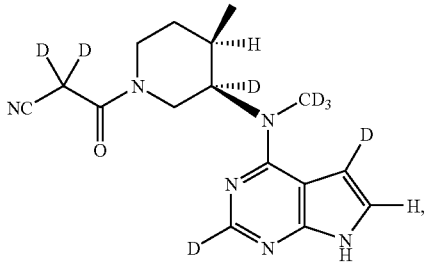

-continued
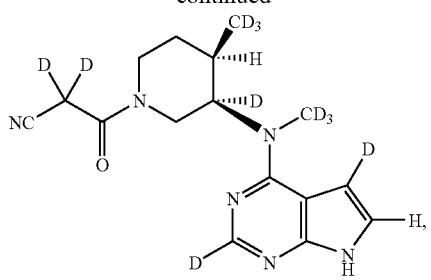
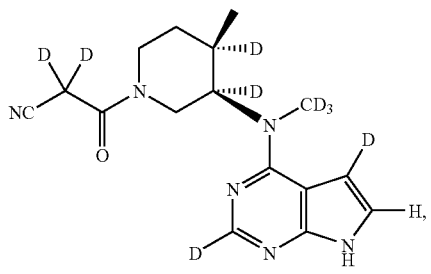
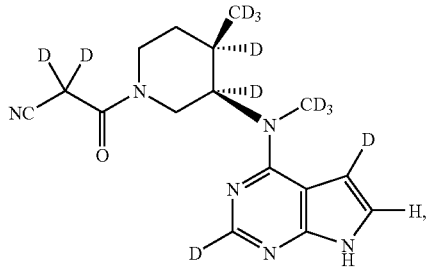
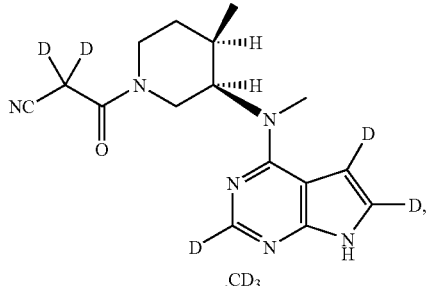
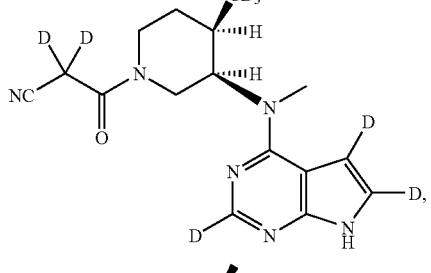
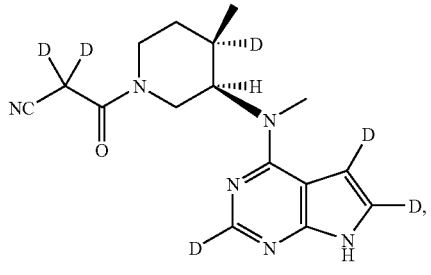
-continued
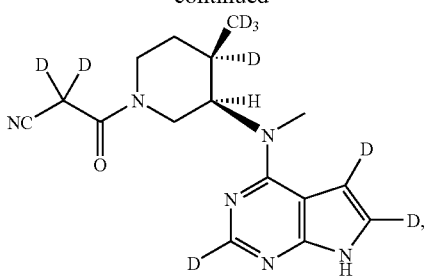
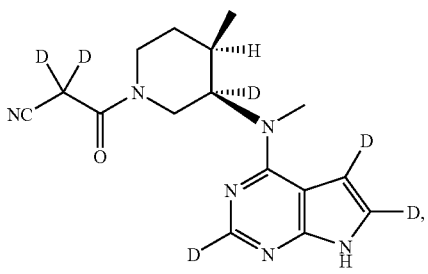
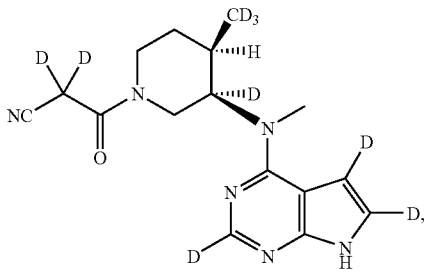
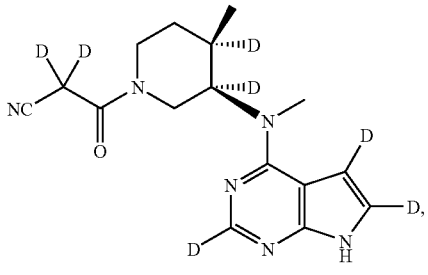
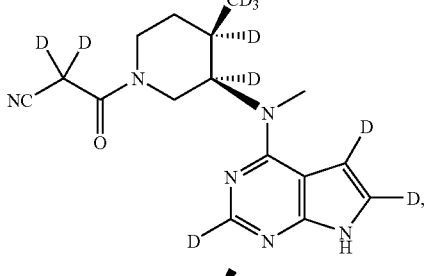
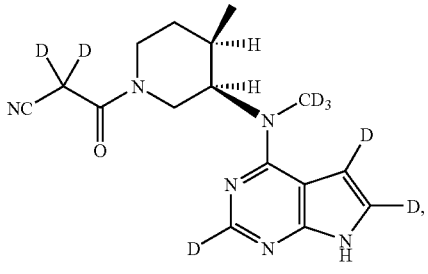

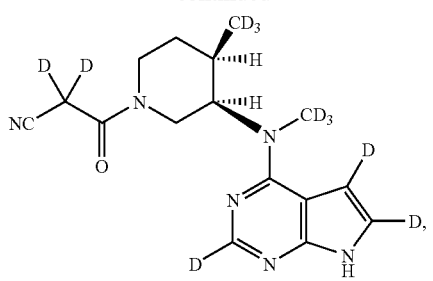
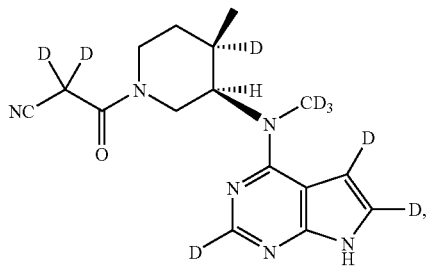
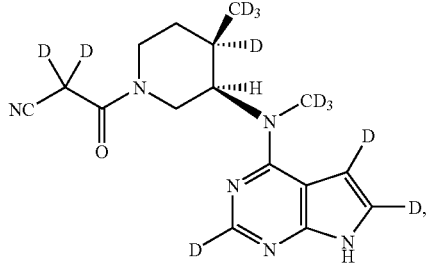
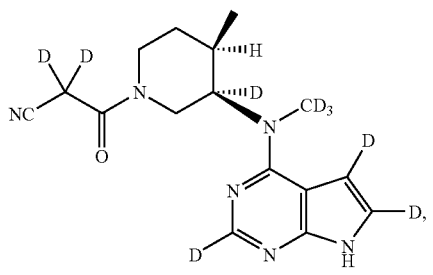
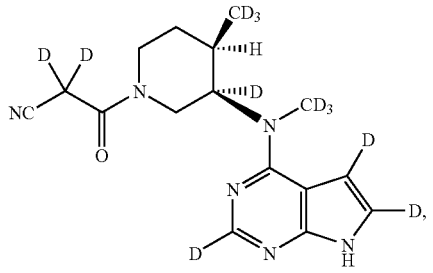
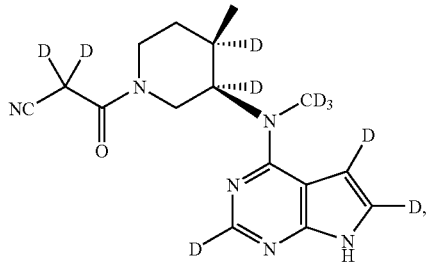
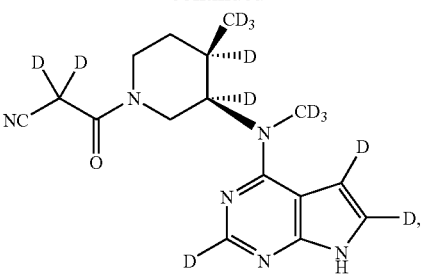
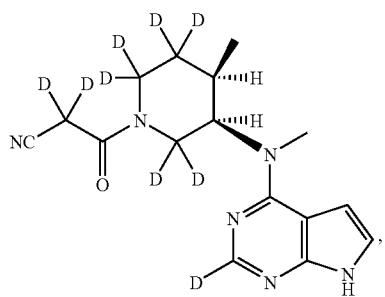
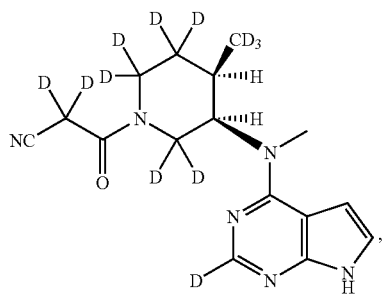
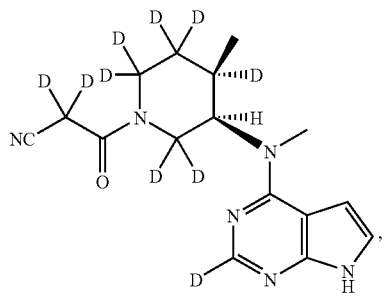
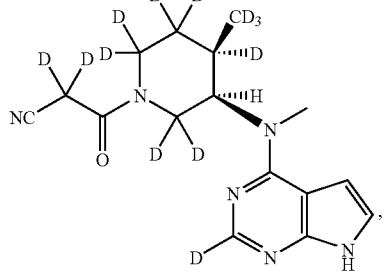

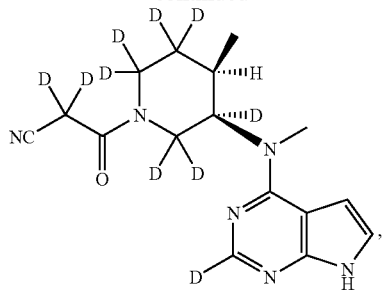
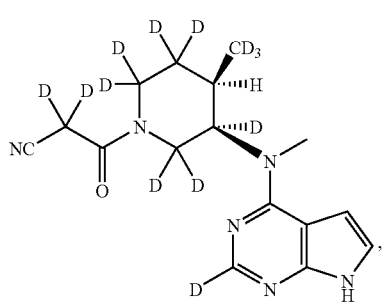
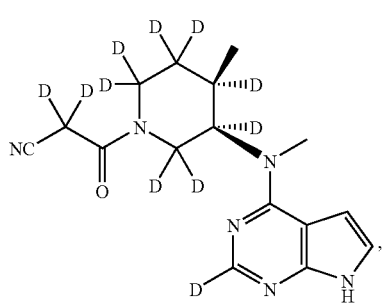
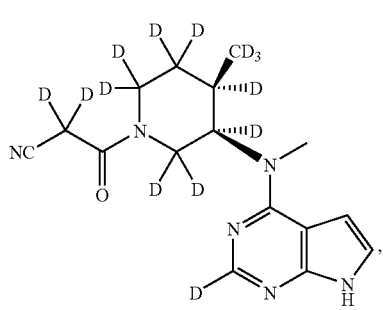
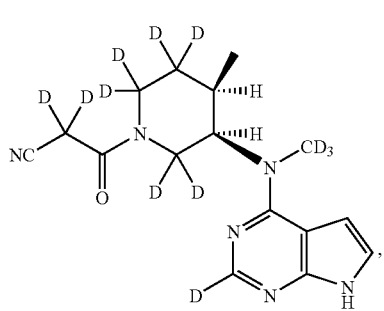
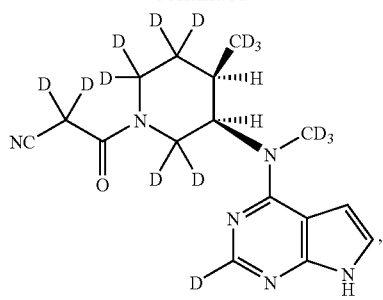
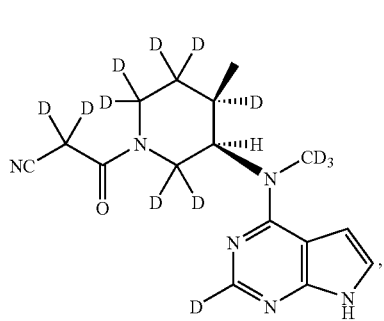
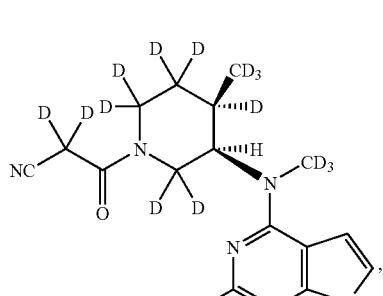
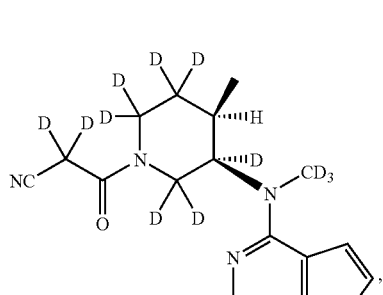
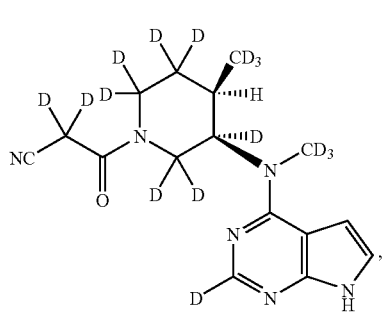

139
-continued
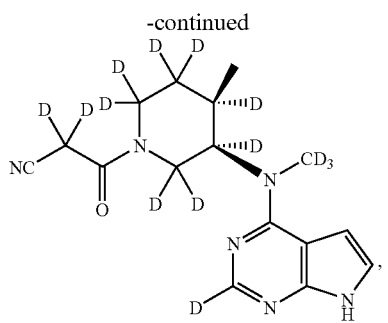
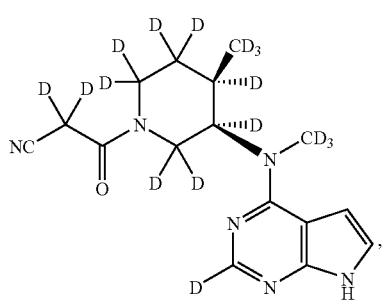
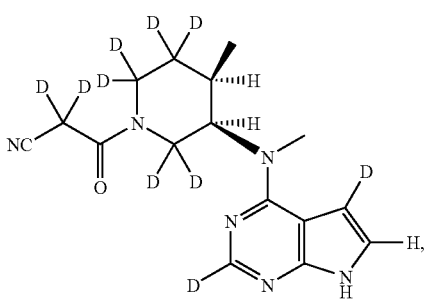
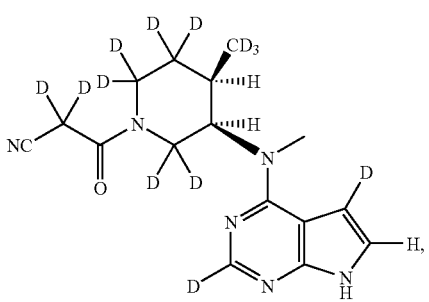
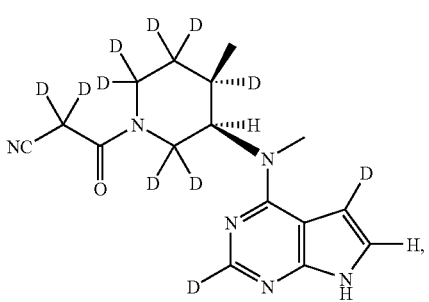
140
-continued
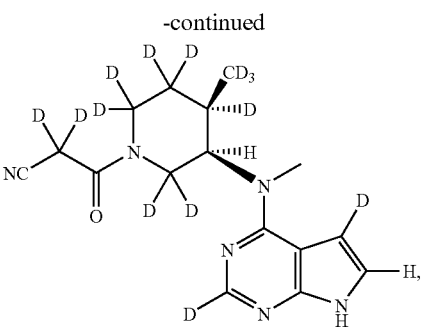
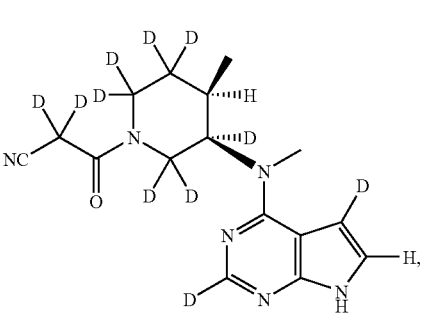
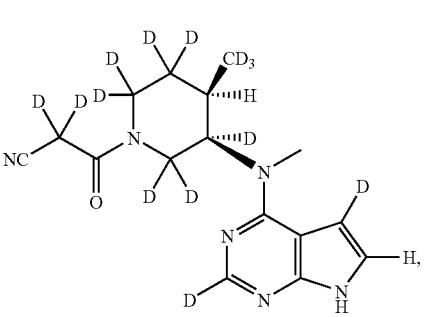
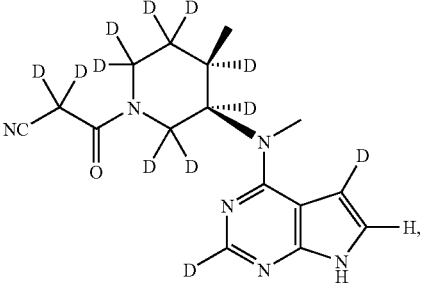
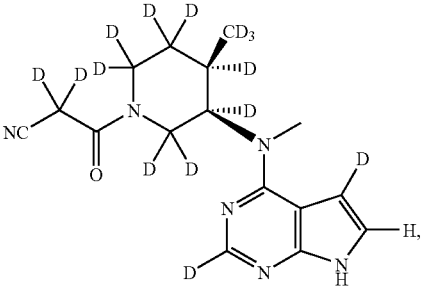

141
-continued
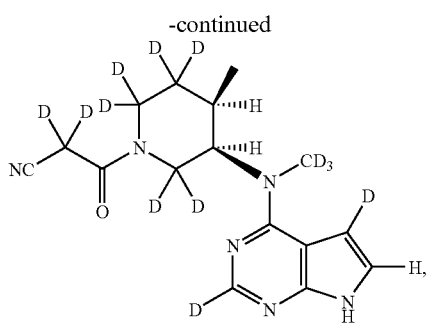
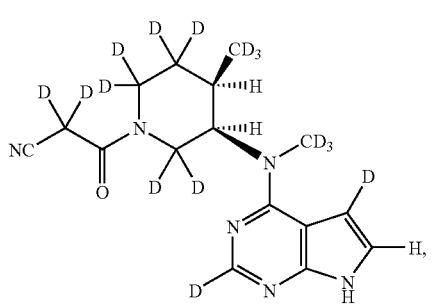
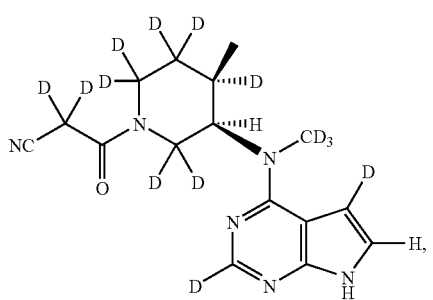
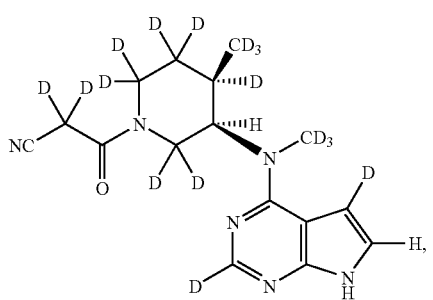
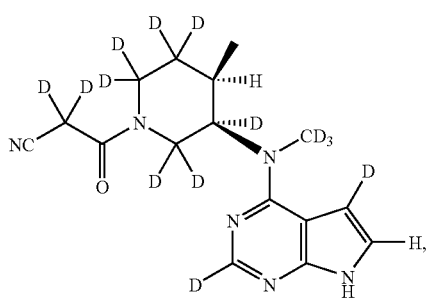
142
-continued
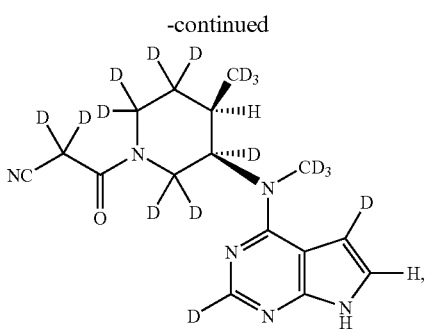
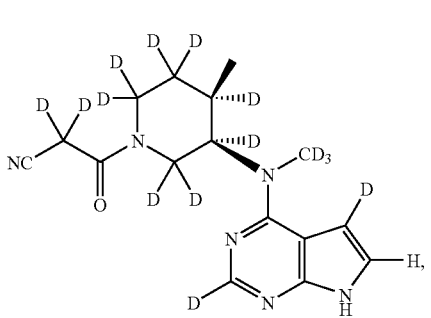
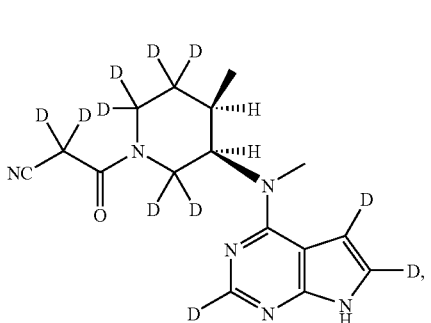
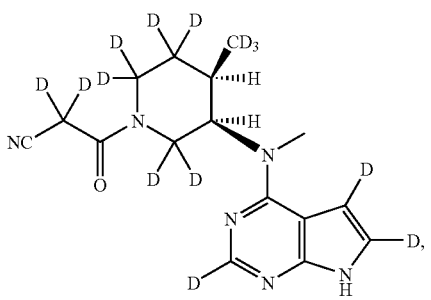

143
-continued
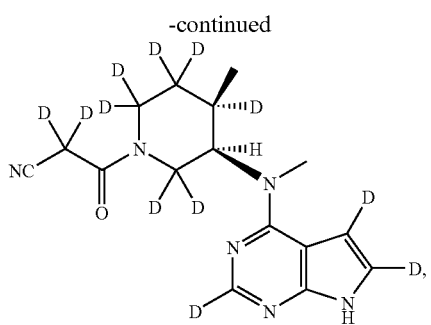
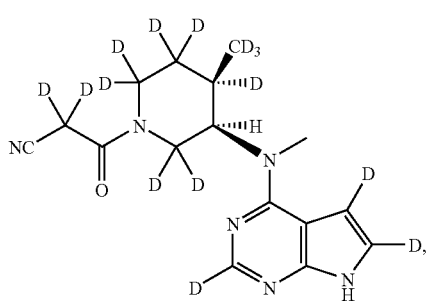
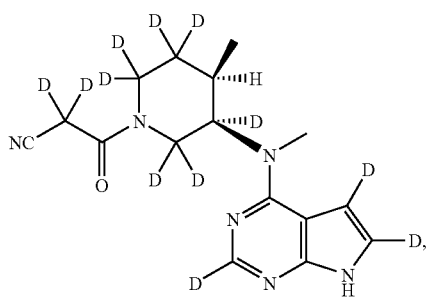
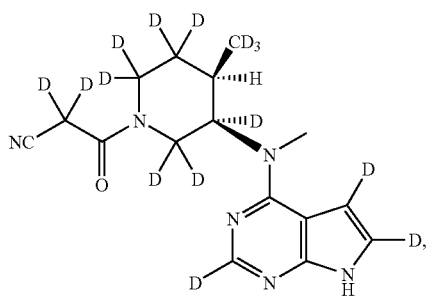
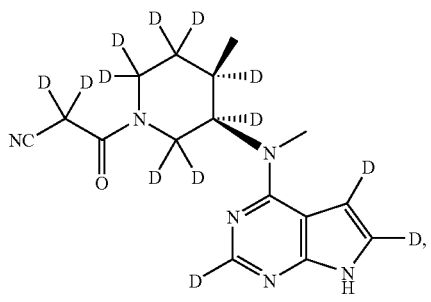
144
-continued
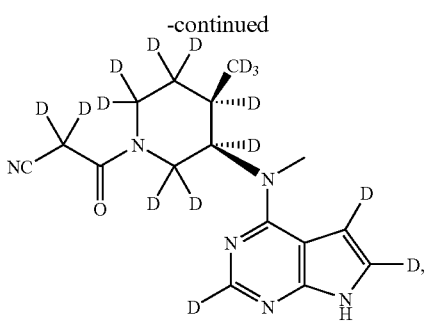
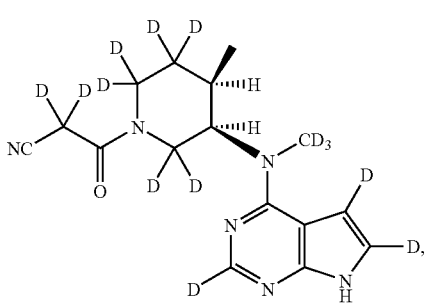
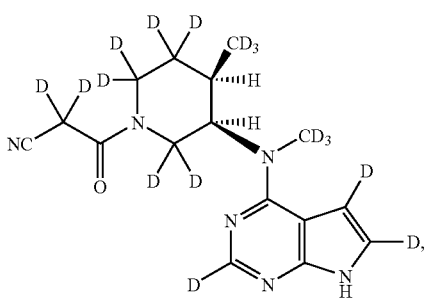
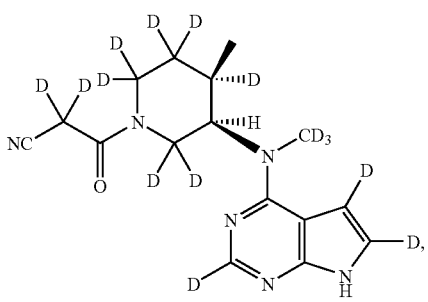
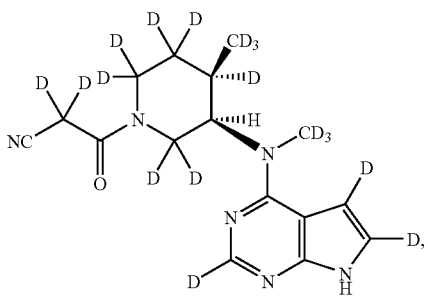

145
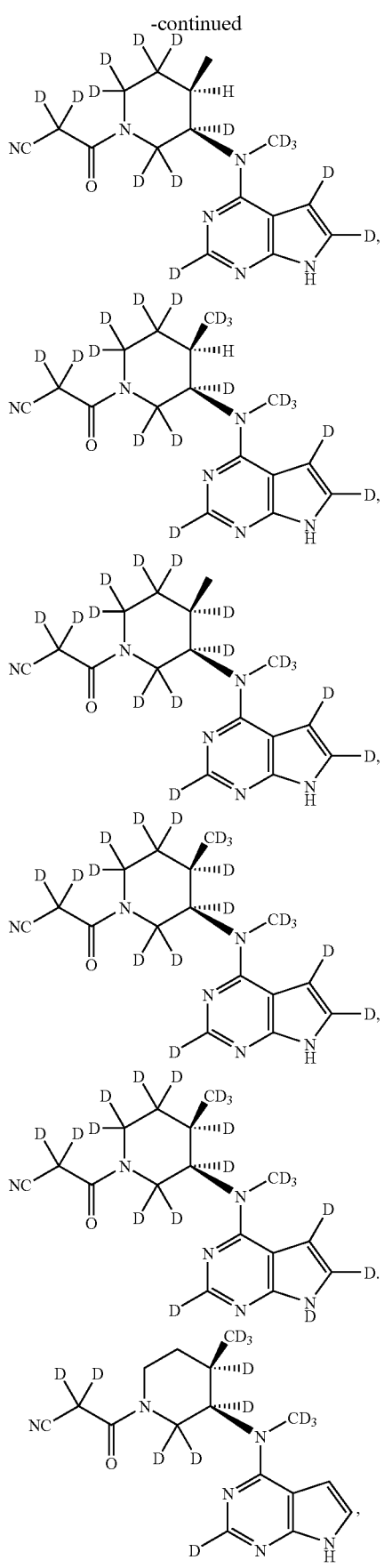
146
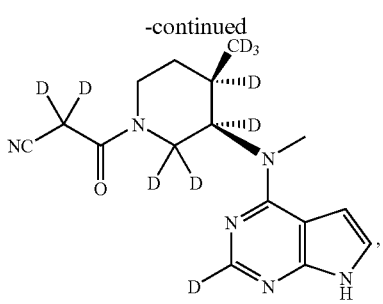
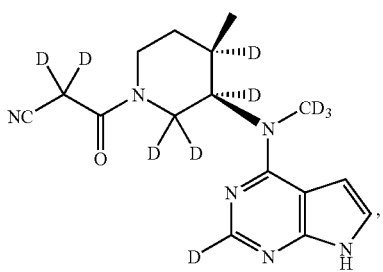
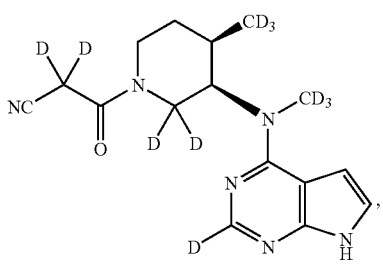
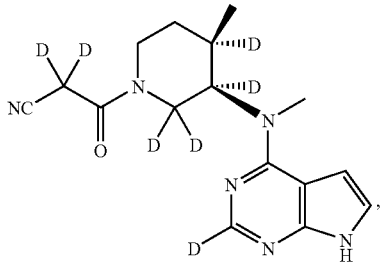
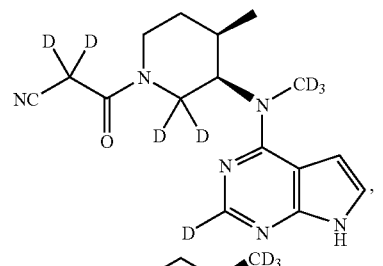
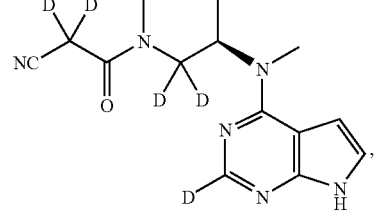

147
-continued
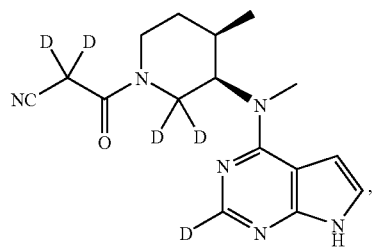
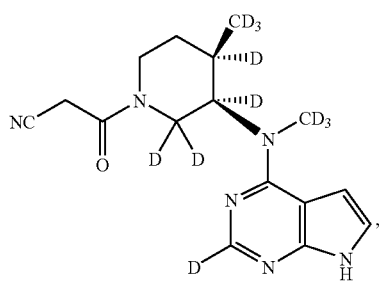
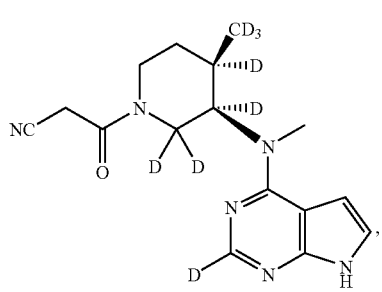
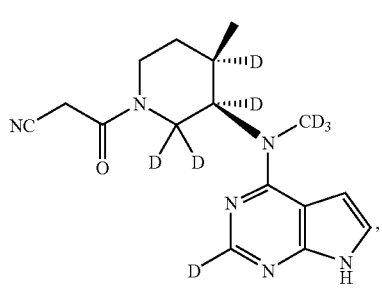
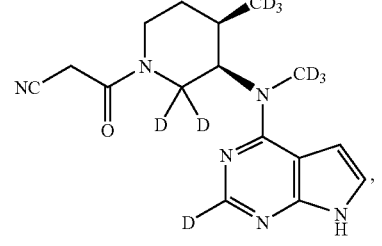
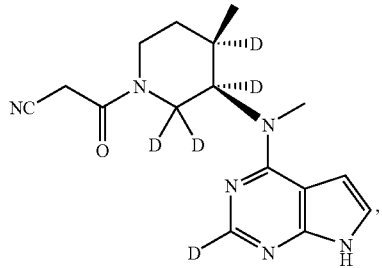
148
-continued
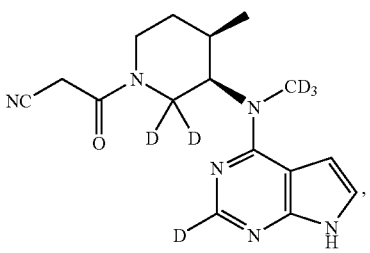
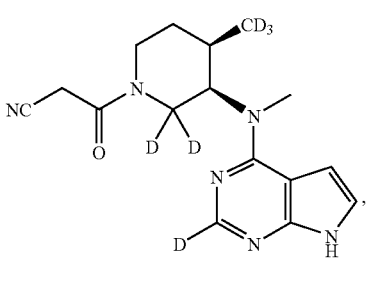
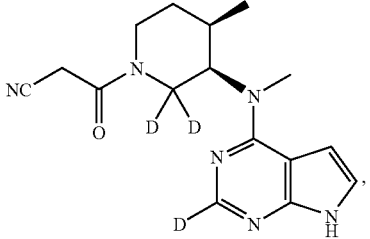
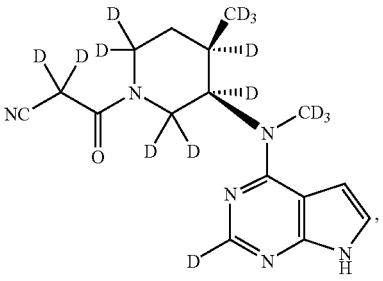
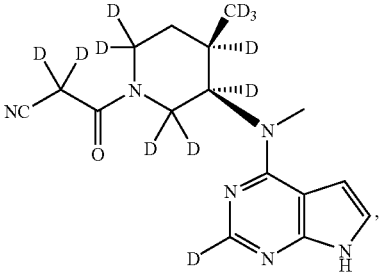
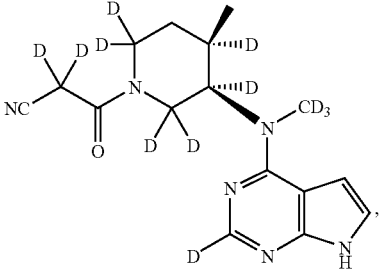

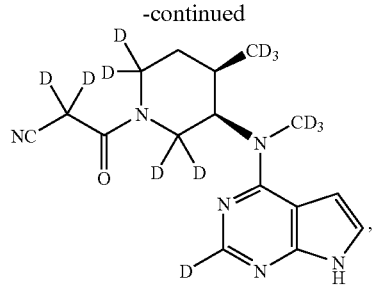
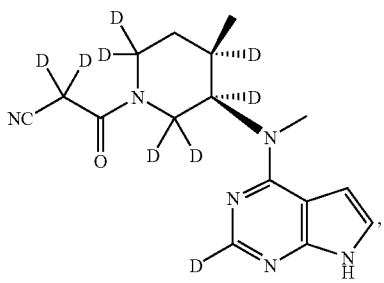
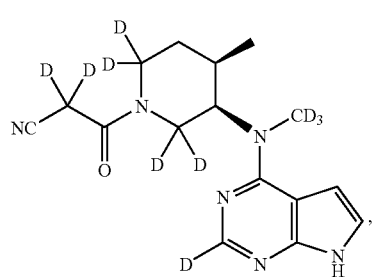
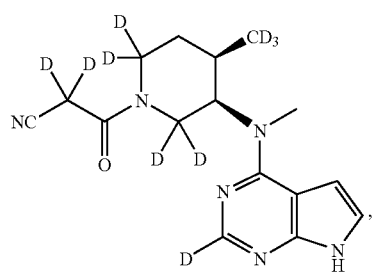
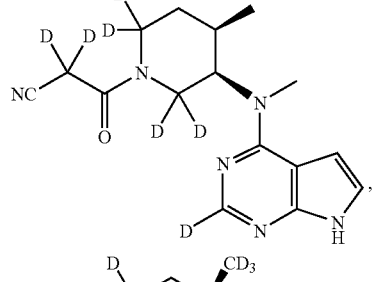
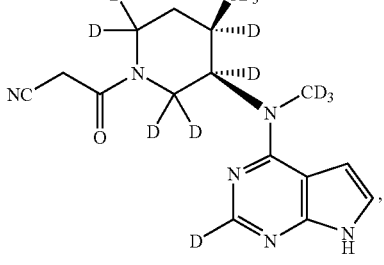
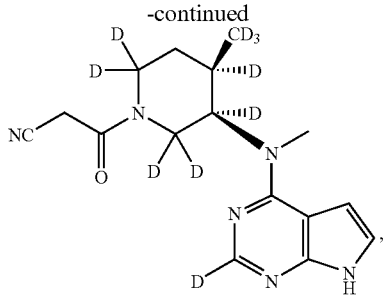
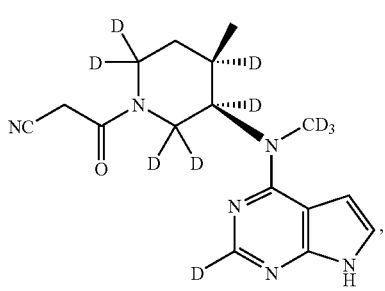
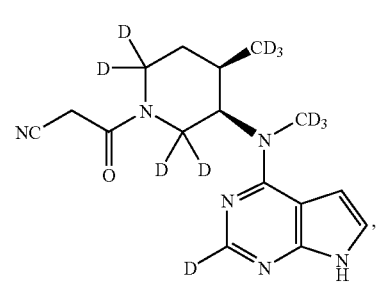
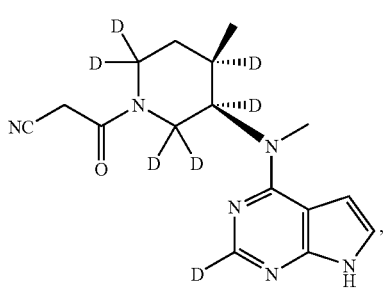
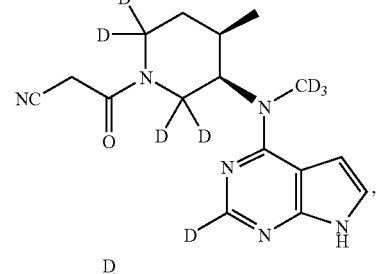
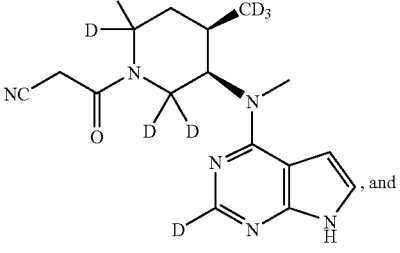

-continued

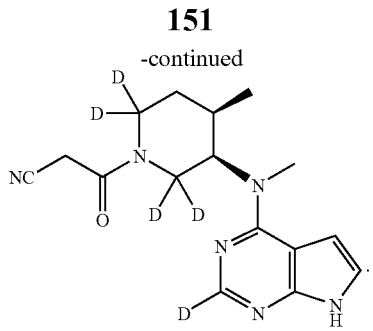

Changes in the metabolic properties of the compounds disclosed herein as compared to their non-isotopically enriched analogs can be shown using the following assays. Compounds listed above which have not yet been made and/or tested are predicted to have changed metabolic properties as shown by one or more of these assays as well.

Biological Activity Assays

In vitro Human Liver Microsomal Stability (HLM) Assay

Liver microsomal stability assays were conducted with 4 mg per mL liver microsome protein with an NADPH-generating system (8.8 mM NADPH, 102.4 mM glucose 6-phosphate, 24 units per mL glucose 6-phosphate dehydrogenase and 13.2 mM magnesium chloride) in 2% sodium bicarbonate. Test compounds were prepared as solutions in 20% acetonitrile-water and added to the assay mixture (final assay concentration 5 microgram per mL) and incubated at 37° C. Final concentration of acetonitrile in the assay should be <1%. Aliquots (50 µL) were taken out at times 0, 30, 60, 90, and 120 minutes, and diluted with ice cold acetonitrile (200 µL) to stop the reactions. Samples were centrifuged at 12,000 RPM for 10 minutes to precipitate proteins. Supernatants were transferred to microcentrifuge tubes and stored for LC/MS/MS analysis of the degradation half-life of the test compounds. It has thus been found that certain isotopically enriched compounds disclosed herein that have been tested in this assay showed an increased degradation half-life as compared to the non-isotopically enriched drug. In certain embodiments, the increase in degradation half-life is at least 5%; at least 10%; at least 15%; at least 20%; at least 30%; at least 40%; at least 50%; at least 60%; at least 70%; at least 80%; at least 90%; or at least 100%.

In Vitro Metabolism Using Human Cytochrome $P_{450}$ Enzymes

The cytochrome $P_{450}$ enzymes are expressed from the corresponding human cDNA using a baculovirus expression system (BD Biosciences, San Jose, Calif.). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound as disclosed herein, the corresponding non-isotopically enriched compound or standard or control in 100 millimolar potassium phosphate (pH 7.4) is incubated at 37° C. for 20 minutes. After incubation, the reaction is stopped by the addition of an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 minutes. The supernatant is analyzed by HPLC/MS/MS.

| Cytochrome $P_{450}$ | Standard |
| --- | --- |
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Monoamine Oxidase A Inhibition and Oxidative Turnover

The procedure is carried out using the methods described by Weyler et al., *Journal of Biological Chemistry* 1985, 260, 13199-13207, which is hereby incorporated by reference in its entirety. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM sodium phosphate buffer, pH 7.2, containing 0.2% Triton X-100 (monoamine oxidase assay buffer), plus 1 mM kynuramine, and the desired amount of enzyme in 1 mL total volume.

Monoamine Oxidase B Inhibition and Oxidative Turnover

The procedure is carried out as described in Uebelhack, *Pharmacopsychiatry* 1998, 31(5), 187-192, which is hereby incorporated by reference in its entirety.

Detecting CP-690550 and its Metabolites by LC-MS

The procedure is carried out as described in Lawendy et al., *J Clin Pharmacol* 2009, 49, 423-429, which is hereby incorporated by reference in its entirety.

Quantifying CP-690550 in Whole Blood by LC-MS

The procedure is carried out as described in Paniagua et al., *Therapeutic Drug Monitoring* 2005, 27(5), 608-616, which is hereby incorporated by reference in its entirety.

Janus Kinase 3 Enzymatic Assay

The procedure is carried out as described in U.S. Pat. No. 6,627,754, which is hereby incorporated by reference in its entirety.

Janus Kinase 3 Enzymatic Assay

The procedure is carried out as described in WO 2003/048162, which is hereby incorporated by reference in its entirety.

Inhibition of Human IL-2 Dependent T-Cell Blast Proliferation

The procedure is carried out as described in WO 2003/048162, which is hereby incorporated by reference in its entirety.

From the foregoing description, one skilled in the art can ascertain the essential characteristics of this invention, and without departing from the spirit and scope thereof, can make various changes and modifications of the invention to adapt it to various usages and conditions.

What is claimed is:

1. A compound having the structural formula:

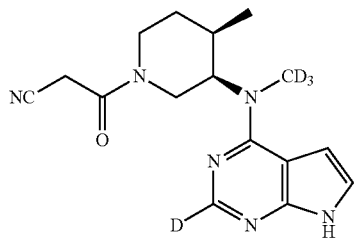

or a pharmaceutically acceptable salt thereof, wherein each position represented as D has deuterium enrichment of no less than about 10%.

2. The compound as recited in claim 1 wherein each position represented as D has deuterium enrichment of no less than about 50%.

3. The compound as recited in claim 1 wherein each position represented as D has deuterium enrichment of no less than about 90%.

4. The compound as recited in claim 1 wherein each position represented as D has deuterium enrichment of no less than about 98%.

5. A pharmaceutical composition comprising a compound as recited in claim 1 together with a pharmaceutically acceptable carrier.

* * * * *